United States Patent
Conn et al.

(10) Patent No.: US 8,969,389 B2
(45) Date of Patent: Mar. 3, 2015

(54) SUBSTITUTED 6-METHYLNICOTINAMIDES AS MGLUR5 POSITIVE ALLOSTERIC MODULATORS

(75) Inventors: P. Jeffrey Conn, Brentwood, TN (US); Craig W. Lindsley, Brentwood, TN (US); Shaun R. Stauffer, Brentwood, TN (US); Ya Zhou, Nashville, TN (US); Jason Manka, Nashville, TN (US); Gregor McDonald, Beerse (BE); José Manuel Bartolome-Nebreda, Toledo (ES)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 13/114,958

(22) Filed: May 24, 2011

(65) Prior Publication Data

US 2011/0294858 A1    Dec. 1, 2011

Related U.S. Application Data

(60) Provisional application No. 61/347,795, filed on May 24, 2010.

(51) Int. Cl.
*A61K 31/44* (2006.01)

(52) U.S. Cl.
CPC ..................................... *A61K 31/44* (2013.01)
USPC .......................................... 514/342; 514/343

(58) Field of Classification Search
USPC ................................................ 514/342, 343
See application file for complete search history.

(56) References Cited

U.S. PATENT DOCUMENTS

| | | | |
|---|---|---|---|
| 6,608,058 B2 | 8/2003 | Yoon et al. | 514/243.5 |
| 7,932,272 B2 | 4/2011 | Nakamoto et al. | 514/336 |
| 8,034,806 B2 | 10/2011 | Conn et al. | 514/212.08 |
| 2003/0092709 A1 | 5/2003 | Yoon et al. | |
| 2007/0105943 A1 | 5/2007 | Nakamoto et al. | |
| 2009/0270362 A1 | 10/2009 | Conn et al. | |
| 2010/0029710 A1 | 2/2010 | Bigge et al. | 514/303 |

FOREIGN PATENT DOCUMENTS

| | | | |
|---|---|---|---|
| AU | 2011258389 | | 11/2012 |
| CA | 2078590 | * | 3/1993 |

(Continued)

OTHER PUBLICATIONS

Caroll F I. (2008) Antagonists at metabotropic glutamate receptor subtype 5: structure activity relationships and therapeutic potential for addiction. Annals of the New York Academy of Sciences, 1141: 221-232.

(Continued)

*Primary Examiner* — San-Ming Hui
(74) *Attorney, Agent, or Firm* — Ballard Spahr LLP

(57) ABSTRACT

In one aspect, the invention relates to substituted 6-methylnicotinamide analogs, derivatives thereof, and related compounds, which are useful as positive allosteric modulators of the metabotropic glutamate receptor subtype 5 (mGluR5); synthetic methods for making the compounds; pharmaceutical compositions comprising the compounds; and methods of treating neurological and psychiatric disorders associated with glutamate dysfunction using the compounds and compositions. This abstract is intended as a scanning tool for purposes of searching in the particular art and is not intended to be limiting of the present invention.

4 Claims, 2 Drawing Sheets

(56) References Cited

FOREIGN PATENT DOCUMENTS

| | | |
|---|---|---|
| CA | 2799966 | 11/2012 |
| CN | 201180033538.7 | 1/2013 |
| EA | 201291327 | 12/2012 |
| EP | 0533130 A1 | 3/1993 |
| EP | 11787265.5 | 12/2012 |
| JP | 2013-512170 | 11/2012 |
| KR | 1020127033660 | 12/2012 |
| MX | MX/a/2012/013560 | 11/2012 |
| WO | WO-92/22203 A1 | 12/1992 |
| WO | WO-96/06822 A1 | 3/1996 |
| WO | WO-2008/151184 A1 | 12/2008 |
| WO | WO-2011/035324 A1 | 3/2011 |
| WO | PCT/US2011/037775 | 5/2011 |

OTHER PUBLICATIONS

Kulkarni SS, et al. (2009) Structure-activity relationships comparing N-(6-methylpyridin-yl)-substituted aryl amides to 2-methyl-6-(substituted-arylethynyl)pyridines or 2-methyl-4-(substituted-arylethynyl)thiazoles as novel metabotropic glutamate receptor subtype 5 antagonists. Journal of Medicinal chemistry, 52(11): 3563-3575.

Rosenbrock H, et al. (2010) Functional interaction of metabotropic glutamate receptor 5 and NMDA-receptor 5 positive allosteric modulator. European Journal of Pharmacology, 639(1-3): 40-46.

Extended European Search Report issued on Nov. 15, 2013 for European Patent Application No. 11787265.5 filed May 24, 2011. (Applicant—Vanderbilt University; Inventors—Conn, et al.) (7 pages).

Official Action issued on Dec. 19, 2013 for EA 201291327 filed Dec. 21, 2012 (Applicant—Vanderbilt University; Inventors—Conn, et al.) (4 pages).

International Search Report issued Sep. 14, 2011 by the International Searching Authority for Application PCT/US2011/037775 filed May 24, 2011 and later published as WO 2011/149963 on Dec. 1, 2011 (Applicant—Vanderbilt University // Inventor—P. Jeffrey Conn, et al.) (2 pages).

Written Opinion issued Sep. 14, 2011 by the International Searching Authority for Application PCT/US2011/037775 filed May 24, 2011 and later published as WO 2011/149963 on Dec. 1, 2011(Applicant—Vanderbilt University // Inventor—P. Jeffrey Conn, et al.) (5 pages).

International Preliminary Report on Patentability issued Nov. 27, 2012 by the International Searching Authority for Application PCT/US2011/037775 filed May 24, 2011 and later published as WO 2011/149963 on Dec. 1, 2011 (Applicant—Vanderbilt University // Inventor—P. Jeffrey Conn, et al.) (6 pages).

Awad, et al., "Activation of Metabotropic Glutamate Receptor 5 has Direct Excitatory Effects and Potentiates NMDA Receptor Currents in Neurons of the Subthalamic Nucleus," Journal of Neuroscience, 2000. 20(21): pp. 7871-7879.

Chavez-Noriega, et al., "Metabotropic Glutamate Receptor: Potential Drug Targets for the Treatment of Schizophrenia," Current Drug Targets: CNS & Neurological Disorder, 2002. 1(3): pp. 261-281.

Chiamulera, et al., "Reinforcing and Locomotor Stimulant Effects of Cocaine Are Absent in mGluR5 Null Mutant Mice," Nature Neuroscience, 2001. 4: pp. 873-874.

Kinney, et al., "A Novel Selective Positive Allosteric Modulator of Metabotropic Glutamate Receptor Subtype 5 Has In Vivo Activity and Antipsychotic-like Effects in Rat Behavioral Models," The Journal of Pharmacology and Experimental Therapeutics, 2005. 313(1): pp. 199-206.

Li, et al., "Synthesis of new β-hydroxy amide ligands and their Ti(IV) complex-catalyzed enantioselective alkynylation of aliphatic and vinyl aldehydes," *Tetrahedron*, 2009. 65: pp. 3611-3614.

Mannaioni, et al., "Metabolic Glutamate Receptors 1 and 5 Differentially Regulate CA1 Pyramidal Cell Function," Journal of Neuroscience, 2001. 21(16): pp. 5925-5934.

Ossowska, et al., "Blockade of the Metabotropic Glutamate Receptor Subtype 5 (mGluR5) Produces Antiparkinsonian-like Effects in Rats," Neuropharmacology, 2001. 41: pp. 413-420.

Salt, et al., "Contributions of mGlu1 and mGlu5 Receptors to Interactions with N-Methyl-D-Aspartate Receptor-mediated Responses and Nociceptive Sensory," Neuroscience, 2001. 100(2): pp. 375-380.

Spooren, et al., "Anxiolytic-like Effects of the Prototypical Metabotropic Glutamate Receptor 5 Antagonist 2-Methyl-5(phenylethynl)pyridine in Rodents," The Journal of Pharmacology and Experimental Therapeutics, 2000. 295(3): pp. 1267-1275.

Tatarczynska, et al., "Potential anxiolytic and Antidepressant-like Effects of MPEP, a Potent, Selective and Systemically Active mGlu5 Receptor Antagonist," British Journal of Pharmacology, 2001. 132(7): pp. 1423-1430.

\* cited by examiner

SUBSTITUTED 6-METHYLNICOTINAMIDES AS MGLUR5 POSITIVE ALLOSTERIC MODULATORS

CROSS-REFERENCE TO RELATED APPLICATIONS

This application claims benefit of U.S. Application Ser. No. 61/347,795, filed May 24, 2010, which is hereby incorporated herein by reference in its entirety.

STATEMENT REGARDING FEDERALLY SPONSORED RESEARCH

This invention was made with government support under Grant no. 5R01 NS031373-15 awarded by the National Institute of Neurological Disorders and Stroke (NINDS) and Grant no. 5R01MH073676-04 awarded by the National Institute of Mental Health (NIMH). The United States government has certain rights in the invention.

BACKGROUND

L-glutamic acid, the most commonly occurring neurotransmitter in the central nervous system, plays a role in a large number of physiological processes. The glutamate-dependent stimulus receptors are divided into two main groups. The first main group forms ligand-controlled ion channels. The second main group is metabotropic glutamate receptors (mGluRs), which belong to the family of G-protein-coupled receptors. Metabotropic glutamate receptors, including mGluR5, have been implicated in a wide range of biological functions, indicating a potential role for the mGluR5 receptor in a variety of disease processes in mammals. Ligands of metabotropic glutamate receptors can be used for the treatment or prevention of acute and/or chronic neurological and/or psychiatric disorders associated with glutamate dysfunction, such as psychosis, schizophrenia, age-related cognitive decline, and the like.

Selective positive allosteric modulators are compounds that do not directly activate receptors by themselves, but binding of these compounds increase the affinity of a glutamate-site agonist at its extracellular N-terminal binding site. Positive allosteric modulation (potentiation) is thus an attractive mechanism for enhancing appropriate physiological receptor activation.

Unfortunately, there is a scarcity of selective positive allosteric modulators for the mGluR5 receptor. Further, conventional mGluR5 receptor modulators typically lack satisfactory aqueous solubility and exhibit poor oral bioavailability. Therefore, there remains a need for methods and compositions that overcome these deficiencies and that effectively provide selective positive allosteric modulators for the mGluR5 receptor.

SUMMARY

In accordance with the purpose(s) of the invention, as embodied and broadly described herein, the invention, in one aspect, relates to compounds useful as positive allosteric modulators (i.e., potentiators) of the metabotropic glutamate receptor subtype 5 (mGluR5), methods of making same, pharmaceutical compositions comprising same, and methods of treating neurological and psychiatric disorders associated with glutamate dysfunction using same.

Disclosed are compounds having a structure represented by a formula:

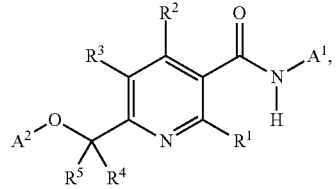

wherein $A^1$ is an organic residue having 2-10 carbons and selected from optionally substituted alkyl, optionally substituted cycloalkyl, optionally substituted heterocycloalkyl, optionally substituted cycloalkenyl, optionally substituted heterocycloalkenyl; optionally substituted aryl, and heteroaryl optionally substituted with one or more of halogen, methyl, trifluoromethyl, ethyl, propyl, or butyl; wherein $A^2$ is an optionally substituted organic residue selected from aryl and heteroaryl having 4-10 carbons; wherein $R^1$ and $R^2$ are independently selected from hydrogen, halogen, C1 to C6 alkyl, aryl, heteroaryl, cycloalkyl, heterocycloalkyl, cycloalkenyl, heterocycloalkenyl, OH, CN, $CO_2H$, $CF_3$, $OCF_3$, $OCH_3$, and —$CHRNH_2(OH)$, wherein is R is $CF_3$; wherein $R^3$ is selected from hydrogen, hydroxyl, halogen, C1 to C6 alkyl, OH, CN, $CO_2H$, $CF_3$, $OCF_3$, $OCH_3$, and —$CHRNH_2(OH)$, wherein is R is $CF_3$; wherein $R^4$ and $R^5$ are independently selected from hydrogen, C1 to C6 alkyl, aryl, heteroaryl, cycloalkyl, heterocycloalkyl, cycloalkenyl, and heterocycloalkenyl, or wherein $R^4$ and $R^5$, together with the intermediate carbon, form a cyclic or heterocyclic ring having from 3 to 6 carbons; or a pharmaceutically acceptable salt or N-oxide thereof, wherein the compound exhibits potentiation of mGluR5 response to glutamate as an increase in response to non-maximal concentrations of glutamate in human embryonic kidney cells transfected with rat mGluR5 in the presence of the compound, compared to the response to glutamate in the absence of the compound.

Also disclosed are pharmaceutical compositions comprising a therapeutically effective amount of a disclosed compound and a pharmaceutically acceptable carrier.

Also disclosed are methods of making a substituted 6-methylnicotinamide comprising the steps of substituting a leaving group with $A^2OH$, wherein $A^2$ is an optionally substituted organic residue selected from aryl and heteroaryl having 4-10 carbons; and forming an amide with $A^1NH_2$, wherein $A^1$ is an organic residue having 2-10 carbons and selected from optionally substituted alkyl, optionally substituted cycloalkyl, optionally substituted heterocycloalkyl, optionally substituted cycloalkenyl, optionally substituted heterocycloalkenyl; optionally substituted aryl, and heteroaryl optionally substituted with one or more of halogen, methyl, trifluoromethyl, ethyl, propyl, or butyl.

Also disclosed are the products of the disclosed methods.

Also disclosed are methods for the treatment of a neurological and/or psychiatric disorder associated with glutamate dysfunction in a mammal comprising the step of administering to the mammal a therapeutically effective amount of least one compound having a structure represented by a formula:

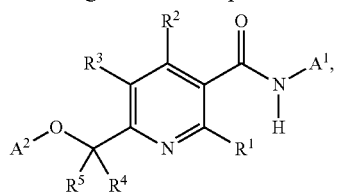

wherein $A^1$ is an organic residue having 2-10 carbons and selected from optionally substituted alkyl, optionally substituted cycloalkyl, optionally substituted heterocycloalkyl, optionally substituted cycloalkenyl, optionally substituted heterocycloalkenyl; optionally substituted aryl, and heteroaryl optionally substituted with one or more of halogen, methyl, trifluoromethyl, ethyl, propyl, or butyl; wherein $A^2$ is an optionally substituted organic residue selected from aryl and heteroaryl having 4-10 carbons; wherein $R^1$ and $R^2$ are independently selected from hydrogen, halogen, C1 to C6 alkyl, aryl, heteroaryl, cycloalkyl, heterocycloalkyl, cycloalkenyl, heterocycloalkenyl, OH, CN, $CO_2H$, $CF_3$, $OCF_3$, $OCH_3$, and —$CHRNH_2(OH)$, wherein $R^3$ is selected from hydrogen, hydroxyl, halogen, C1 to C6 alkyl, OH, CN, $CO_2H$, $CF_3$, $OCF_3$, $OCH_3$, and —$CHRNH_2(OH)$, wherein is R is $CF_3$; wherein $R^4$ and $R^5$ are independently selected from hydrogen, C1 to C6 alkyl, aryl, heteroaryl, cycloalkyl, heterocycloalkyl, cycloalkenyl, and heterocycloalkenyl, or wherein $R^4$ and $R^5$, together with the intermediate carbon, form a cyclic or heterocyclic ring having from 3 to 6 carbons; or a pharmaceutically acceptable salt or N-oxide thereof.

Also disclosed are methods for potentiation of metabotropic glutamate receptor activity in a mammal comprising the step of administering to the mammal a therapeutically effective amount of least one compound having a structure represented by a formula:

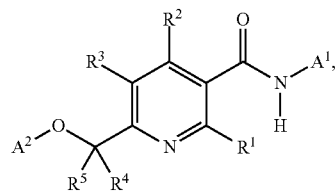

wherein $A^1$ is an organic residue having 2-10 carbons and selected from optionally substituted alkyl, optionally substituted cycloalkyl, optionally substituted heterocycloalkyl, optionally substituted cycloalkenyl, optionally substituted heterocycloalkenyl; optionally substituted aryl, and heteroaryl optionally substituted with one or more of halogen, methyl, trifluoromethyl, ethyl, propyl, or butyl; wherein $A^2$ is an optionally substituted organic residue selected from aryl and heteroaryl having 4-10 carbons; wherein $R^1$ and $R^2$ are independently selected from hydrogen, halogen, C1 to C6 alkyl, aryl, heteroaryl, cycloalkyl, heterocycloalkyl, cycloalkenyl, heterocycloalkenyl, OH, CN, $CO_2H$, $CF_3$, $OCF_3$, $OCH_3$, and —$CHRNH_2(OH)$, wherein is R is $CF_3$; wherein $R^3$ is selected from hydrogen, hydroxyl, halogen, C1 to C6 alkyl, OH, CN, $CO_2H$, $CF_3$, $OCF_3$, $OCH_3$, and —$CHRNH_2(OH)$, wherein is R is $CF_3$; wherein $R^4$ and $R^5$ are independently selected from hydrogen, C1 to C6 alkyl, aryl, heteroaryl, cycloalkyl, heterocycloalkyl, cycloalkenyl, and heterocycloalkenyl, or wherein $R^4$ and $R^5$, together with the intermediate carbon, form a cyclic or heterocyclic ring having from 3 to 6 carbons; or a pharmaceutically acceptable salt or N-oxide thereof.

Also disclosed are methods for partial agonism of metabotropic glutamate receptor activity in a mammal comprising the step of administering to the mammal a therapeutically effective amount of least one compound having a structure represented by a formula:

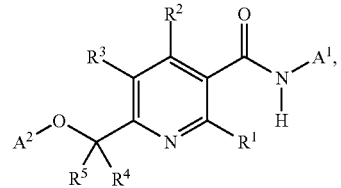

wherein $A^1$ is an organic residue having 2-10 carbons and selected from optionally substituted alkyl, optionally substituted cycloalkyl, optionally substituted heterocycloalkyl, optionally substituted cycloalkenyl, optionally substituted heterocycloalkenyl; optionally substituted aryl, and heteroaryl optionally substituted with one or more of halogen, methyl, trifluoromethyl, ethyl, propyl, or butyl; wherein $A^2$ is an optionally substituted organic residue selected from aryl and heteroaryl having 4-10 carbons; wherein $R^1$ and $R^2$ are independently selected from hydrogen, halogen, C1 to C6 alkyl, aryl, heteroaryl, cycloalkyl, heterocycloalkyl, cycloalkenyl, heterocycloalkenyl, OH, CN, $CO_2H$, $CF_3$, $OCF_3$, $OCH_3$, and —$CHRNH_2(OH)$, wherein is R is $CF_3$; wherein $R^3$ is selected from hydrogen, hydroxyl, halogen, C1 to C6 alkyl, OH, CN, $CO_2H$, $CF_3$, $OCF_3$, $OCH_3$, and —$CHRNH_2(OH)$, wherein is R is $CF_3$; wherein $R^4$ and $R^5$ are independently selected from hydrogen, C1 to C6 alkyl, aryl, heteroaryl, cycloalkyl, heterocycloalkyl, cycloalkenyl, and heterocycloalkenyl, or wherein $R^4$ and $R^5$, together with the intermediate carbon, form a cyclic or heterocyclic ring having from 3 to 6 carbons; or a pharmaceutically acceptable salt or N-oxide thereof.

Also disclosed are methods for enhancing cognition in a mammal comprising the step of administering to the mammal an effective amount of least one compound having a structure represented by a formula:

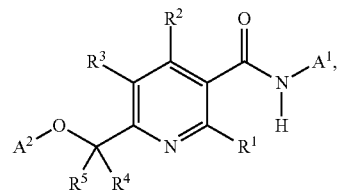

wherein $A^1$ is an organic residue having 2-10 carbons and selected from optionally substituted alkyl, optionally substituted cycloalkyl, optionally substituted heterocycloalkyl, optionally substituted cycloalkenyl, optionally substituted heterocycloalkenyl; optionally substituted aryl, and heteroaryl optionally substituted with one or more of halogen, methyl, trifluoromethyl, ethyl, propyl, or butyl; wherein $A^2$ is an optionally substituted organic residue selected from aryl and heteroaryl having 4-10 carbons; wherein $R^1$ and $R^2$ are independently selected from hydrogen, halogen, C1 to C6 alkyl, aryl, heteroaryl, cycloalkyl, heterocycloalkyl, cycloalkenyl, heterocycloalkenyl, OH, CN, $CO_2H$, $CF_3$, $OCF_3$, $OCH_3$, and —$CHRNH_2(OH)$, wherein is R is $CF_3$; wherein $R^3$ is selected from hydrogen, hydroxyl, halogen, C1 to C6 alkyl, OH, CN, $CO_2H$, $CF_3$, $OCF_3$, $OCH_3$, and —$CHRNH_2(OH)$, wherein is R is $CF_3$; wherein $R^4$ and $R^5$ are independently selected from hydrogen, C1 to C6 alkyl, aryl, heteroaryl, cycloalkyl, heterocycloalkyl, cycloalkenyl, and heterocycloalkenyl, or wherein $R^4$ and $R^5$, together with the intermediate carbon, form a cyclic or heterocyclic ring having from 3 to 6 carbons; or a pharmaceutically acceptable salt or N-oxide thereof.

Also disclosed are methods for modulating mGluR5 activity in a mammal comprising the step of administering to the mammal an effective amount of least one compound having a structure represented by a formula:

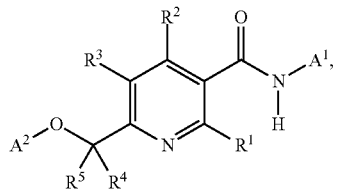

wherein $A^1$ is an organic residue having 2-10 carbons and selected from optionally substituted alkyl, optionally substituted cycloalkyl, optionally substituted heterocycloalkyl, optionally substituted cycloalkenyl, optionally substituted heterocycloalkenyl; optionally substituted aryl, and heteroaryl optionally substituted with one or more of halogen, methyl, trifluoromethyl, ethyl, propyl, or butyl; wherein $A^2$ is an optionally substituted organic residue selected from aryl and heteroaryl having 4-10 carbons; wherein $R^1$ and $R^2$ are independently selected from hydrogen, halogen, C1 to C6 alkyl, aryl, heteroaryl, cycloalkyl, heterocycloalkyl, cycloalkenyl, heterocycloalkenyl, OH, CN, $CO_2H$, $CF_3$, $OCF_3$, $OCH_3$, and —$CHRNH_2(OH)$, wherein is R is $CF_3$; wherein $R^3$ is selected from hydrogen, hydroxyl, halogen, C1 to C6 alkyl, OH, CN, $CO_2H$, $CF_3$, $OCF_3$, $OCH_3$, and —$CHRNH_2(OH)$, wherein is R is $CF_3$; wherein $R^4$ and $R^5$ are independently selected from hydrogen, C1 to C6 alkyl, aryl, heteroaryl, cycloalkyl, heterocycloalkyl, cycloalkenyl, and heterocycloalkenyl, or wherein $R^4$ and $R^5$, together with the intermediate carbon, form a cyclic or heterocyclic ring having from 3 to 6 carbons; or a pharmaceutically acceptable salt or N-oxide thereof.

Also disclosed are methods for modulating mGluR5 activity in at least one cell, comprising the step of contacting the at least one cell with an effective amount of least one compound having a structure represented by a formula:

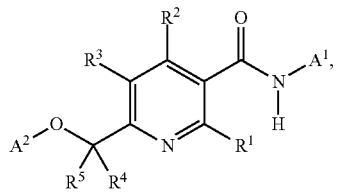

wherein $A^1$ is an organic residue having 2-10 carbons and selected from optionally substituted alkyl, optionally substituted cycloalkyl, optionally substituted heterocycloalkyl, optionally substituted cycloalkenyl, optionally substituted heterocycloalkenyl; optionally substituted aryl, and heteroaryl optionally substituted with one or more of halogen, methyl, trifluoromethyl, ethyl, propyl, or butyl; wherein $A^2$ is an optionally substituted organic residue selected from aryl and heteroaryl having 4-10 carbons; wherein $R^1$ and $R^2$ are independently selected from hydrogen, halogen, C1 to C6 alkyl, aryl, heteroaryl, cycloalkyl, heterocycloalkyl, cycloalkenyl, heterocycloalkenyl, OH, CN, $CO_2H$, $CF_3$, $OCF_3$, $OCH_3$, and —$CHRNH_2(OH)$, wherein is R is $CF_3$; wherein $R^3$ is selected from hydrogen, hydroxyl, halogen, C1 to C6 alkyl, OH, CN, $CO_2H$, $CF_3$, $OCF_3$, $OCH_3$, and —$CHRNH_2(OH)$, wherein is R is $CF_3$; wherein $R^4$ and $R^5$ are independently selected from hydrogen, C1 to C6 alkyl, aryl, heteroaryl, cycloalkyl, heterocycloalkyl, cycloalkenyl, and heterocycloalkenyl, or wherein $R^4$ and $R^5$, together with the intermediate carbon, form a cyclic or heterocyclic ring having from 3 to 6 carbons; or a pharmaceutically acceptable salt or N-oxide thereof.

Also disclosed are kits comprising at least one disclosed compound or at least one disclosed product and one or more of at least one agent known to increase mGluR5 activity; at least one agent known to decrease mGluR5 activity; at least one agent known to treat a neurological and/or psychiatric disorder; at least one agent known to treat a disease of uncontrolled cellular proliferation; or instructions for treating a disorder associated with glutamate dysfunction.

Also disclosed are methods for manufacturing a medicament comprising combining at least one disclosed compound or at least one disclosed product with a pharmaceutically acceptable carrier or diluent.

Also disclosed are uses of a disclosed compound or a disclosed product in the manufacture of a medicament for the treatment of a disorder associated with glutamate dysfunction in a mammal.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
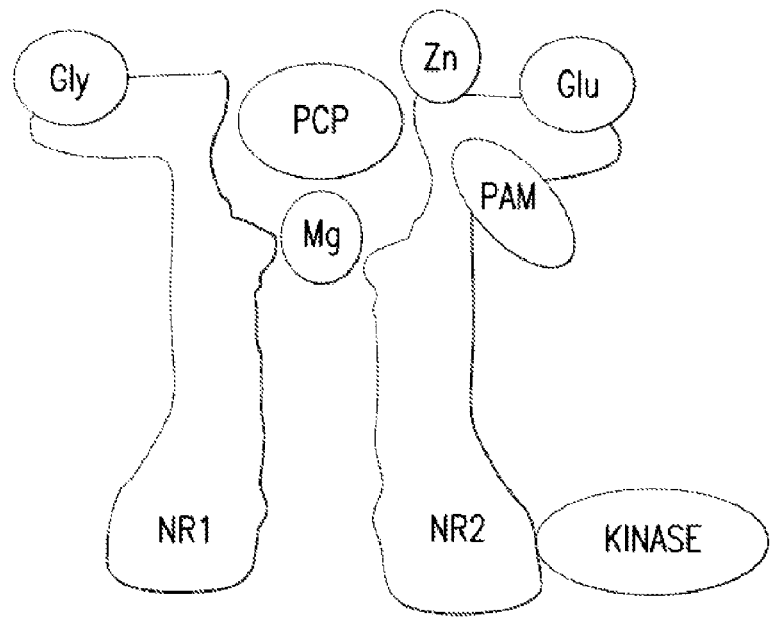
FIG. 1 shows a schematic of the NMDA receptor.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

As used herein, the term "mGluR5 receptor positive allosteric modulator" refers to any exogenously administered compound or agent that directly or indirectly augments the activity of the mGluR5 receptor in the presence or in the absence of the endogenous ligand (such as glutamate) in an animal, in particular a mammal, for example a human. The term "mGluR5 receptor positive allosteric modulator5 includes a compound that is an "mGluR5 receptor allosteric potentiator" or an "mGluR5 receptor allosteric agonist," as well as a compound that has mixed activity as both an "mGluR5 receptor allosteric potentiator" and an "mGluR5 receptor allosteric agonist."

As used herein, the term "mGluR5 receptor allosteric potentiator" refers to any exogenously administered compound or agent that directly or indirectly augments the response produced by the endogenous ligand (such as glutamate) when it binds to the orthosteric site of the mGluR5 receptor in an animal, in particular a mammal, for example a human. The mGluR5 receptor allosteric potentiator binds to a site other than the orthosteric site (an allosteric site) and positively augments the response of the receptor to an agonist. Because it does not induce desensitization of the receptor, activity of a compound as an mGluR5 receptor allosteric potentiator provides advantages over the use of a pure mGluR5 receptor allosteric agonist. Such advantages can include, for example, increased safety margin, higher tolerability, diminished potential for abuse, and reduced toxicity.

As used herein, the term "mGluR5 receptor allosteric agonist" refers to any exogenously administered compound or agent that directly augments the activity of the mGluR5 receptor in the absence of the endogenous ligand (such as glutamate) in an animal, in particular a mammal, for example a human. The mGluR5 receptor allosteric agonist binds to the orthosteric glutamate site of the mGluR5 receptor and directly influences the orthosteric site of the mGluR5 receptor. Because it does not require the presence of the endogenous ligand, activity of a compound as an mGluR5 receptor allosteric agonist provides advantages over the use of a pure mGluR5 receptor allosteric potentiator, such as more rapid onset of action.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more neurological and/or psychiatric disorder associated with glutamate dysfunction prior to the administering step. In some aspects of the disclosed method, the subject has been diagnosed with a need for positive allosteric modulation of metabotropic glutamate receptor activity prior to the administering step. In some aspects of the disclosed method, the subject has been diagnosed with a need for partial agonism of metabotropic glutamate receptor activity prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

In some aspects of the disclosed methods, the subject has been diagnosed with a need for treatment of one or more neurological and/or psychiatric disorder associated with glutamate dysfunction prior to the administering step. In some aspects of the disclosed method, the subject has been diagnosed with a need for potentiation of metabotropic glutamate receptor activity prior to the administering step. In some aspects of the disclosed method, the subject has been diagnosed with a need for partial agonism of metabotropic glutamate receptor activity prior to the administering step.

As used herein, the term "diagnosed with a need for potentiation of metabotropic glutamate receptor activity" refers to having been subjected to a physical examination by a person of skill, for example, a physician, and found to have a condition that can be diagnosed or treated by potentiation of metabotropic glutamate receptor activity. As used herein, "diagnosed with a need for partial agonism of metabotropic glutamate receptor activity" means having been subjected to a physical examination by a person of skill, for example, a physician, and found to have a condition that can be diagnosed or treated by partial agonism of metabotropic glutamate receptor activity. As used herein, "diagnosed with a need for treatment of one or more neurological and/or psychiatric disorder associated with glutamate dysfunction" means having been subjected to a physical examination by a person of skill, for example, a physician, and found to have one or more neurological and/or psychiatric disorder associated with glutamate dysfunction.

As used herein, the phrase "identified to be in need of treatment for a disorder," or the like, refers to selection of a subject based upon need for treatment of the disorder. For example, a subject can be identified as having a need for treatment of a disorder (e.g., a disorder related to mGluR5 activity) based upon diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target histamine receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{50}$," is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_{50}$ refers to the concentration of agonist that provokes a response halfway between the baseline and maximum response.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The term "hydrolysable residue" is meant to refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "leaving group" refers to an atom (or a group of atoms) with electron withdrawing ability that can be displaced as a stable species, taking with it the bonding electrons. Examples of suitable leaving groups include sulfonate esters, including triflate, mesylate, tosylate, brosylate, and halides.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^•$, -(haloR$^•$), —$(CH_2)_{0-2}OH$, —$(CH_2)_{0-2}R^•$, —$(CH_2)_{0-2}CH(OR^•)_2$; —O(haloR$^•$), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —C(O)SR$^•$, —($C_{1-4}$ straight or branched alkylene)C(O)OR$^•$, or —SSR$^•$ wherein each R$^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O$—, or —$S(C(R^*_2))_{2-3}S$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^•$, -(haloR$^•$), —OH, —OR$^•$, —O(haloR$^•$), —CN, —C(O)OH, —C(O)OR$^•$, —$NH_2$, —NHR$^•$, —$NR^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —$NR^†_2$, —C(O)R$^†$, —C(O)OR$^†$, —C(O)C(O)R$^†$, —$C(O)CH_2C(O)R^†$, —$S(O)_2R^†$, —$S(O)_2NR^†_2$, —$C(S)NR^†_2$, —$C(NH)NR^†_2$, or —$N(R^†)S(O)_2R^†$; wherein each R$^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —$NH_2$, —NHR$^•$, —$NR^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$—$OA^2$ or $OA^1$—$(OA^2)_a$—$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropentyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "carboxylic acid" as used herein is represented by the formula —C(O)OH.

The term "ester" as used herein is represented by the formula —$OC(O)A^1$ or —$C(O)OA^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula —$(A^1O(O)C-A^2-C(O)O)_a$— or —$(A^1O(O)C-A^2-OC(O))_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula —$(A^1O-A^2O)_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula $A^1C(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by the formula —SH.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

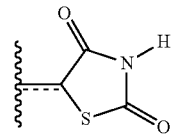

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable minor images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (ee). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are minor image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

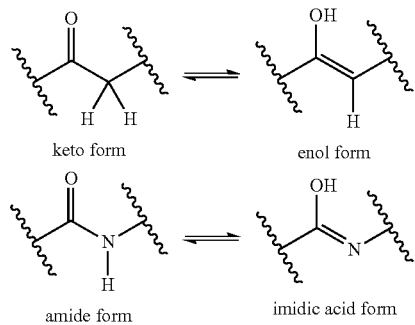

keto form     enol form amide form    imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

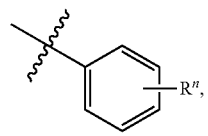

which is understood to be equivalent to a formula:

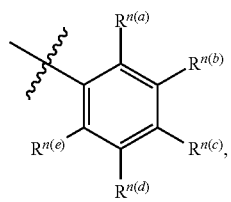

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

The following abbreviations are used herein. DMF: dimethyl formamide. EtOAc: ethyl acetate. THF: tetrahydrofuran. DIPEA or DIEA: diisopropylethylamine. HOBt: 1-hydroxybenzotriazole. EDC: 1-ethyl-3-[3-dimethylaminopropyl]carbodiimide hydrochloride. DMSO: dimethylsulfoxide. DMAP: 4-Dimethylaminopyridine. RT: Room temperature. h: Hours. Min: Minutes. DCM: Dichloromethane. MeCN: Acetonitrile. MeOH: methanol. iPrOH: 2-Propanol. n-BuOH: 1-Butanol.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Development of Novel Allosteric Potentiators of mGluR5

Figure 2:
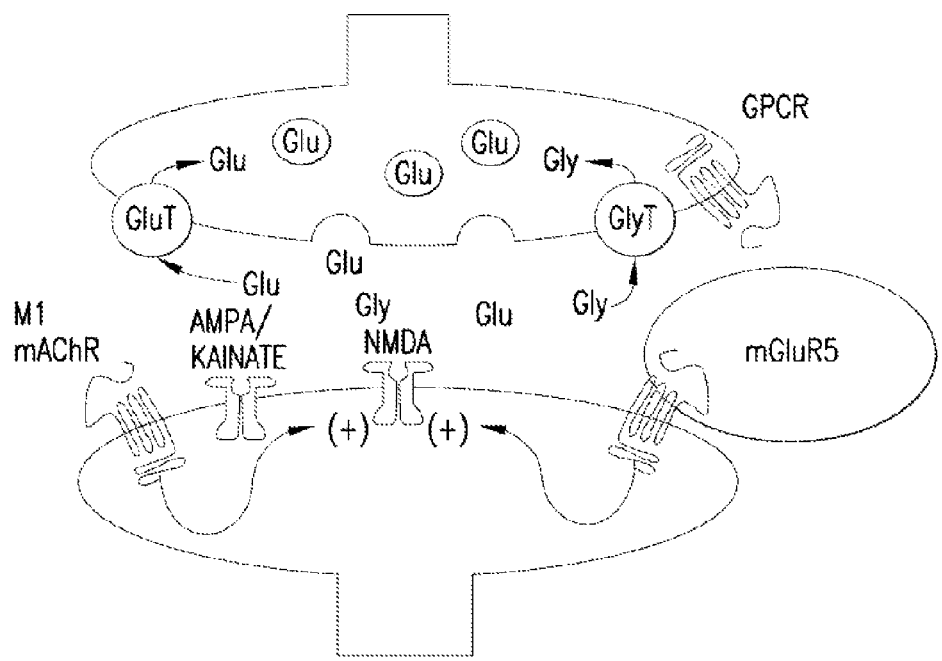
FIG. 2 shows a schematic illustrating that activation of mGluR5 potentiates NMDA receptor function.
Figure 3:
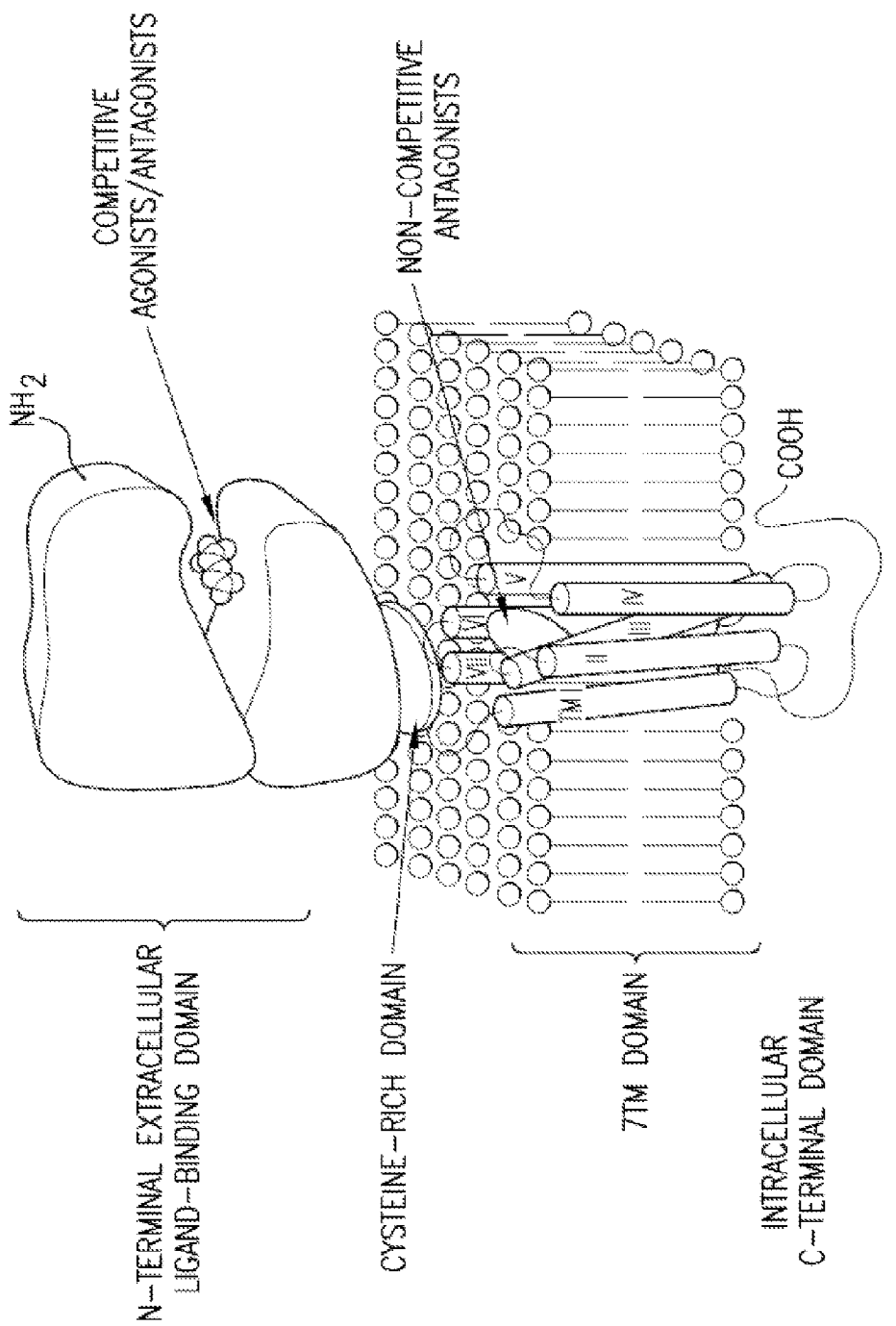
FIG. 3 illustrates allosteric modulation of mGluR5.

Phencyclidine (PCP) and other NMDA receptor antagonists induce a psychotic state in humans similar to schizophrenia. In schizophrenia patients, PCP and ketamine exacerbate/precipitate preexisting positive and negative symptoms in stable patients. Treatment with NMDA receptor co-agonists can improve positive and negative symptoms. A schematic of the NMDA receptor is shown in FIG. 1. Activation of mGluR5 potentiates NMDA receptor function. See FIG. 2. Orthosteric ligands lack subtype selectivity and can cause unwanted side effects. Allosteric modulators (see FIG. 3) targeting transmembrane domain offer alternative: TMD is significantly less conserved.

C. Compounds

In one aspect, the invention relates to compounds useful as positive allosteric modulators (potentiators) of the metabotropic glutamate receptor subtype 5 (mGluR5). More specifically, in one aspect, the present invention relates to compounds that allosterically modulate mGluR5 receptor activity, affecting the sensitivity of mGluR5 receptors to agonists without acting as orthosteric agonists themselves. The compounds of the invention are useful in the treatment neurological and psychiatric disorders associated with glutamate dysfunction and other diseases in which metabotropic glutamate receptors are involved, as further described herein.

1. Structure

In one aspect, the invention relates to a compound having a structure represented by a formula:

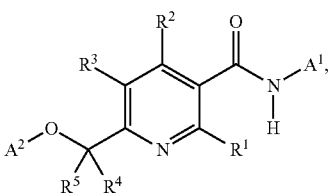

wherein $A^1$ is an organic residue having 2-10 carbons and selected from optionally substituted alkyl, optionally substituted cycloalkyl, optionally substituted heterocycloalkyl, optionally substituted cycloalkenyl, optionally substituted heterocycloalkenyl; optionally substituted aryl, and heteroaryl optionally substituted with one or more of halogen, methyl, trifluoromethyl, ethyl, propyl, or butyl; wherein $A^2$ is an optionally substituted organic residue selected from aryl and heteroaryl having 4-10 carbons; wherein $R^1$ and $R^2$ are independently selected from hydrogen, halogen, C1 to C6 alkyl, aryl, heteroaryl, cycloalkyl, heterocycloalkyl, cycloalkenyl, heterocycloalkenyl, OH, CN, $CO_2H$, $CF_3$, $OCF_3$, $OCH_3$, and $—CHRNH_2(OH)$, wherein is R is $CF_3$; wherein $R^3$ is selected from hydrogen, hydroxyl, halogen, C1 to C6 alkyl, OH, CN, $CO_2H$, $CF_3$, $OCF_3$, $OCH_3$, and $—CHRNH_2(OH)$, wherein is R is $CF_3$; wherein $R^4$ and $R^5$ are independently selected from hydrogen, C1 to C6 alkyl, aryl, heteroaryl, cycloalkyl, heterocycloalkyl, cycloalkenyl, and heterocycloalkenyl, or wherein $R^4$ and $R^5$, together with the intermediate carbon, form a cyclic or heterocyclic ring having from 3 to 6 carbons; or a pharmaceutically acceptable salt or N-oxide thereof, wherein the compound exhibits potentiation of mGluR5 response to glutamate as an increase in response to non-maximal concentrations of glutamate in human embryonic kidney cells transfected with rat mGluR5 in the presence of the compound, compared to the response to glutamate in the absence of the compound.

In a further aspect, the compound has a structure represented by a formula:

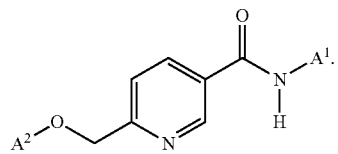

In a further aspect, the compound has a structure represented by a formula:

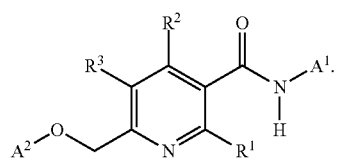

In a further aspect, the compound has a structure represented by a formula:

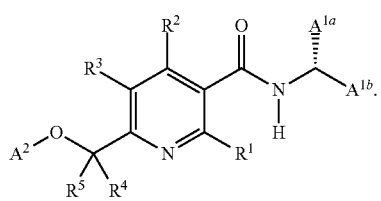

a. $A^1$ Groups

In one aspect, $A^1$ is an organic residue having 2-10 carbons and selected from optionally substituted alkyl, optionally substituted cycloalkyl, optionally substituted heterocycloalkyl, optionally substituted cycloalkenyl, optionally substituted heterocycloalkenyl; optionally substituted aryl, and heteroaryl optionally substituted with one or more of halogen, methyl, trifluoromethyl, ethyl, propyl, or butyl.

In one aspect, $A^1$ is optionally substituted alkyl. In a further aspect, $A^1$ is optionally substituted alkyl selected from ethyl, propyl, butyl, pentyl, hexyl, heptyl, octyl, nonyl, or decyl. In a further aspect, $A^1$ is ethyl, propyl, butyl, pentyl, hexyl, heptyl, octyl, nonyl, or decyl.

In one aspect, $A^1$ is optionally substituted cycloalkyl. In a further aspect, $A^1$ is optionally substituted cycloalkyl selected from cyclopropyl, cyclobutyl, cyclopentyl, cyclohexyl, cycloheptyl, cyclooctyl, cyclononyl, bicyclo[3.1.0]hexyl, bicyclo[4.1.0]heptyl, bicyclo[5.1.0]octyl, bicyclo[6.1.0]nonyl, bicyclo[3.2.0]heptyl, bicyclo[4.2.0]octyl, bicyclo[5.2.0]nonyl, bicyclo[3.3.0]octyl, bicyclo[4.3.0]nonyl, bicyclo[2.2.1]heptyl, bicyclo[3.2.1]octyl, bicyclo[4.2.1]nonyl, bicyclo[2.2.2]octyl, bicyclo[3.2.2]nonyl, and bicyclo[3.3.1]nonyl.

In one aspect, $A^1$ is optionally substituted heterocycloalkyl. In a further aspect, $A^1$ is optionally substituted heterocycloalkyl selected from oxirane, oxetane, tetrahydrofuran, tetrahydro-2H-pyran, oxepane, oxocane, dioxirane, dioxetane, dioxolane, dioxane, dioxepane, dioxocane, thiirane, thietane, tetrahydrothiophene, tetrahydro-2H-thiopyran, thiepane, thiocane, dithiirane, dithietane, dithiolane, dithiane, dithiepane, dithiocane, oxathiirane, oxathietane, oxathiolane, oxathiane, oxathiepane, oxathiocane, aziridine, azetidine, pyrrolidone, piperidine, azepane, azocane, diaziridine, diazetidine, imidazolidine, piperazine, diazepane, diazocane, hexahydropyrimidine, triazinane, oxaziridine, oxazetidine, oxazolidine, morpholine, oxazepane, oxazocane, thiaziridine, thiazetidine, thiazolidine, thiomorpholine, thiazepane, and thiazocane.

In one aspect, $A^1$ is optionally substituted cycloalkenyl. In a further aspect, $A^1$ is optionally substituted cycloalkenyl selected from cyclobutenyl, cyclopentenyl, cyclopentadienyl, cyclohexenyl, cyclohexadienyl, cycloheptenyl, cycloheptadienyl, cyclooctenyl, cyclooctadienyl, cyclononenyl, and cyclononadienyl.

In one aspect, $A^1$ is optionally substituted heterocycloalkenyl. In a further aspect, $A^1$ is optionally substituted heterocycloalkenyl comprising pyrazolinone, imidazolinone, or a mono-, di- or tri-unsaturated analog of a heterocycloalkyl selected from oxirane, oxetane, tetrahydrofuran, tetrahydro-2H-pyran, oxepane, oxocane, dioxirane, dioxetane, dioxolane, dioxane, dioxepane, dioxocane, thiirane, thietane, tetrahydrothiophene, tetrahydro-2H-thiopyran, thiepane, thiocane, dithiirane, dithietane, dithiolane, dithiane, dithiepane, dithiocane, oxathiirane, oxathietane, oxathiolane, oxathiane, oxathiepane, oxathiocane, aziridine, azetidine, pyrrolidone, piperidine, azepane, azocane, diaziridine, diazetidine, imidazolidine, piperazine, diazepane, diazocane, hexahydropyrimidine, triazinane, oxaziridine, oxazetidine, oxazolidine, morpholine, oxazepane, oxazocane, thiaziridine, thiazetidine, thiazolidine, thiomorpholine, thiazepane, and thiazocane.

In one aspect, $A^1$ is optionally substituted aryl. In a further aspect, $A^1$ is phenyl. In a further aspect, $A^1$ is optionally substituted phenyl. In a further aspect, $A^1$ is phenyl optionally substituted with 1-2 groups selected from fluoro, chloro, methyl, ethyl, propyl, butyl, trifluoromethyl, methoxyl, ethoxyl, propoxyl, and butoxyl. In a further aspect, $A^1$ is phenyl or naphthyl.

In one aspect, $A^1$ is heteroaryl optionally substituted with one or more of halogen, methyl, trifluoromethyl, ethyl, propyl, or butyl. In a further aspect, $A^1$ is optionally substituted heteroaryl selected from oxazolyl, isoxazolyl, pyrazolyl, furanyl, pyranyl, imidazolyl, thiophenyl, pyridinyl, pyridazinyl, pyrimidinyl, pyrazinyl, triazinyl, tetrazinyl, benzofuranyl, benzothiophene, indolyl, indazolyl, quinolinyl, naphthyridinyl, benzothiazolyl, benzooxazolyl, benzoimidazolyl, and benzotriazolyl. In a further aspect, $A^1$ is optionally substituted 2-pyridinyl, 3-pyridinyl, or 4-pyridinyl.

In one aspect, $A^1$ has a structure represented by a formula:

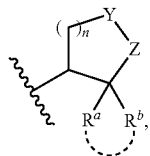

wherein n is 0, 1, or 2; wherein $R^a$ and $R^b$ are independently selected from hydrogen, halogen, cycano, hydroxyl, methoxyl, trifluoromethoxyl, methyl, trifluoromethyl, ethyl, and propyl, or $R^a$ and $R^b$, together with the intermediate carbon, form a cyclic or heterocyclic ring having from 3 to 6 carbons; and wherein both Y and Z are carbon, or wherein Y and Z are together —NHC(O)—, or wherein Y and Z are together —C(O)NH—, or wherein Y is NH, O, or $SO_2$, and Z is carbon, or wherein Y is carbon, and Z is NH, O, or $SO_2$.

In a further aspect, $A^1$ has a structure represented by a formula:

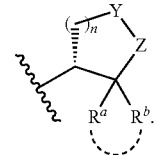

In a further aspect, $A^1$ has a structure represented by a formula:

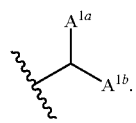

In one aspect, the compound has a structure represented by a formula:

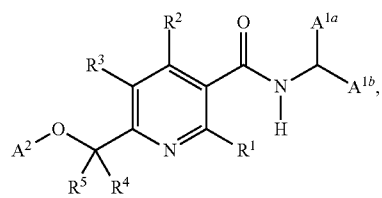

wherein $A^{1a}$ is an organic residue having up to four carbons and selected from optionally substituted alkyl, optionally substituted cycloalkyl, optionally substituted heterocycloalkyl, optionally substituted heterocycloalkenyl; and optionally substituted heteroaryl; wherein $A^{1b}$ is an organic residue having up to eight carbons and selected from optionally substituted alkyl, optionally substituted cycloalkyl, optionally substituted heterocycloalkyl, optionally substituted cycloalkenyl, optionally substituted heterocycloalkenyl; optionally substituted aryl, and heteroaryl optionally substituted with one or more of halogen, methyl, trifluoromethyl, ethyl, propyl, or butyl; and wherein $A^{1a}$ and $A^{1b}$ together have 1-9 carbons. In a further aspect, $A^{1a}$ is optionally substituted alkyl. In a further aspect, the compound has a structure represented by a formula:

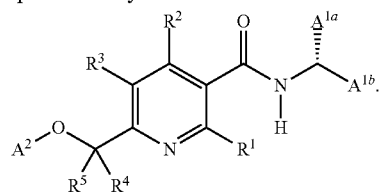

b. $A^2$ Groups

In one aspect, $A^2$ is an optionally substituted organic residue selected from aryl and heteroaryl having 4-10 carbons. In a further aspect, $A^2$ is optionally substituted aryl. In a further aspect, $A^2$ is phenyl. In a further aspect, $A^2$ is optionally substituted phenyl. In a further aspect, $A^2$ is phenyl optionally substituted with 1-2 groups selected from fluoro, chloro, cyano, hydroxyl, —OCF$_3$, —OCH$_3$, methyl, ethyl, propyl, butyl, trifluoromethyl, methoxyl, ethoxyl, propoxyl, and butoxyl. In a further aspect, A$^2$ is phenyl or naphthyl. In a further aspect, A$^2$ is optionally substituted heteroaryl. In a further aspect, A$^2$ is optionally substituted 2-pyridinyl, 3-pyridinyl, or 4-pyridinyl.

In one aspect, A$^2$ is substituted with 0-2 groups, 0-1 groups, 1-2 groups, 2 groups, 1 group, or 0 groups. In a further aspect, the group(s) are independently selected from halogen (e.g., fluoro, chloro, bromo, or iodo), C1-C4 alkyl (e.g., methyl, ethyl, propyl, cyclopropyl, or butyl), C1-C4 haloalkyl (e.g., trifluoromethyl or perfluoroethyl), C1-C4 alkoxyl (e.g., methoxyl, ethoxyl, propoxyl, cyclopropoxyl, or butoxyl), C1-C4 haloalkoxyl (e.g., trifluoromethoxyl or perfluoroethoxyl), and cyano. In a still further aspect, the group(s) are selected from C1-C4 alkyl, C1-C4 alkoxyl, and cyano. In an even further aspect, the group(s) are selected from halogen, C1-C4 haloalkyl, and C1-C4 haloalkoxyl. In a further aspect, A$^2$ is substituted with 0-2 fluoro groups.

In a further aspect, A$^2$ is phenyl, 2-pyridyl, 3-pyridyl, 4-pyridyl, or pyrimidine, and wherein A$^2$ is substituted with 0-2 groups. For example, A$^2$ can be phenyl substituted with 0-2 groups. As a further example, A$^2$ can be 2-pyridyl substituted with 0-1 groups. As a further example, A$^2$ can be 3-pyridyl substituted with 0-1 groups. As a further example, A$^2$ can be 4-pyridyl substituted with 0-1 groups. As a further example, A$^2$ can be pyrimidine substituted with 0-1 groups.

c. R$^1$ Groups

In one aspect, R$^1$ is selected from hydrogen, halogen, C1 to C6 alkyl, aryl, heteroaryl, cycloalkyl, heterocycloalkyl, cycloalkenyl, heterocycloalkenyl, OH, CN, CO$_2$H, CF$_3$, OCF$_3$, OCH$_3$, and —CHRNH$_2$(OH), wherein is R is CF$_3$. In a further aspect, R$^1$ is selected from hydrogen, halogen, C1 to C6 alkyl, aryl, heteroaryl, cycloalkyl, heterocycloalkyl, cycloalkenyl, and heterocycloalkenyl. In a further aspect, R$^1$ is hydrogen. In a further aspect, R$^1$ is halogen, C1 to C6 alkyl, aryl, heteroaryl, cycloalkyl, heterocycloalkyl, cycloalkenyl, or heterocycloalkenyl. In a further aspect, R$^1$ is fluoro or chloro. In a further aspect, R$^1$ is methyl, ethyl, propyl, butyl, pentyl, or hexyl. In a further aspect, R$^1$ is selected from OH, CN, CO$_2$H, CF$_3$, OCF$_3$, OCH$_3$, and —CHRNH$_2$(OH), wherein is R is CF$_3$.

d. R$^2$ Groups

In one aspect, R$^2$ is selected from hydrogen, halogen, C1 to C6 alkyl, aryl, heteroaryl, cycloalkyl, heterocycloalkyl, cycloalkenyl, heterocycloalkenyl, OH, CN, CO$_2$H, CF$_3$, OCF$_3$, OCH$_3$, and —CHRNH$_2$(OH), wherein is R is CF$_3$. In a further aspect, R$^2$ is selected from hydrogen, halogen, C1 to C6 alkyl, aryl, heteroaryl, cycloalkyl, heterocycloalkyl, cycloalkenyl, and heterocycloalkenyl. In a further aspect, R$^2$ is hydrogen. In a further aspect, R$^2$ is halogen, C1 to C6 alkyl, aryl, heteroaryl, cycloalkyl, heterocycloalkyl, cycloalkenyl, or heterocycloalkenyl. In a further aspect, R$^2$ is fluoro or chloro. In a further aspect, R$^2$ is methyl, ethyl, propyl, butyl, pentyl, or hexyl. In a further aspect, R$^2$ is selected from OH, CN, CO$_2$H, CF$_3$, OCF$_3$, OCH$_3$, and —CHRNH$_2$(OH), wherein is R is CF$_3$.

e. R$^3$ Groups

In one aspect, R$^3$ is selected from hydrogen, hydroxyl, halogen, C1 to C6 alkyl, OH, CN, CO$_2$H, CF$_3$, OCF$_3$, OCH$_3$, and —CHRNH$_2$(OH), wherein is R is CF$_3$. In a further aspect, R$^3$ is selected from hydrogen, hydroxyl, halogen, and C1 to C6 alkyl. In a further aspect, R$^3$ is hydrogen. In a further aspect, R$^3$ is hydroxyl, halogen, or C1 to C6 alkyl. In a further aspect, R$^3$ is fluoro or chloro. In a further aspect, R$^3$ is methyl, ethyl, propyl, butyl, pentyl, or hexyl. In a further aspect, R$^3$ is selected from OH, CN, CO$_2$H, CF$_3$, OCF$_3$, OCH$_3$, and —CHRNH$_2$(OH), wherein is R is CF$_3$.

In a further aspect, all of R$^1$, R$^2$, and R$^3$ are hydrogen.

f. R$^4$ Groups

In one aspect, R$^4$ is selected from hydrogen, C1 to C6 alkyl, aryl, heteroaryl, cycloalkyl, heterocycloalkyl, cycloalkenyl, and heterocycloalkenyl. In a further aspect, R$^4$ is hydrogen. In a further aspect, R$^4$ is C1 to C6 alkyl, aryl, heteroaryl, cycloalkyl, heterocycloalkyl, cycloalkenyl, or heterocycloalkenyl. In a further aspect, R$^4$ is methyl, ethyl, propyl, butyl, pentyl, or hexyl.

g. R$^5$ Groups

In one aspect, R$^5$ is selected from hydrogen, C1 to C6 alkyl, aryl, heteroaryl, cycloalkyl, heterocycloalkyl, cycloalkenyl, and heterocycloalkenyl. In a further aspect, R$^5$ is hydrogen. In a further aspect, R$^5$ is C1 to C6 alkyl, aryl, heteroaryl, cycloalkyl, heterocycloalkyl, cycloalkenyl, or heterocycloalkenyl. In a further aspect, R$^5$ is methyl, ethyl, propyl, butyl, pentyl, or hexyl.

In one aspect, R$^4$ and R$^5$, together with the intermediate carbon, form a cyclic or heterocyclic ring having from 3 to 6 carbons. In a further aspect, R$^4$ and R$^5$, together with the intermediate carbon, form a cyclic ring having from 3 to 6 carbons, for example, cyclopropyl, cyclobutyl, cyclopentyl, or cyclohexyl. In a yet further aspect, R$^4$ and R$^5$, together with the intermediate carbon, form a heterocyclic ring having from 3 to 6 carbons.

In a further aspect, both R$^4$ and R$^5$ are hydrogen.

2. Example Compounds

In one aspect, the invention relates to a compound having a structure represented by a structure:

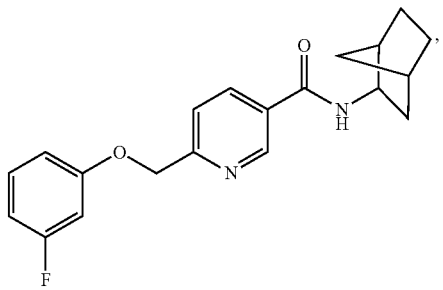

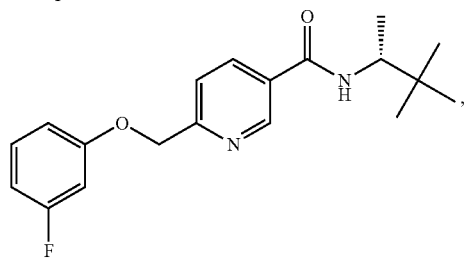

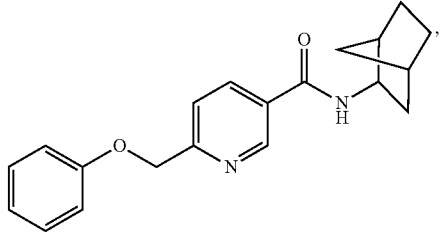

29
-continued
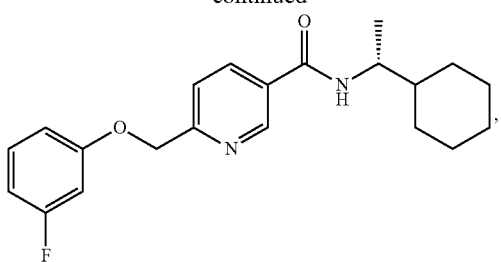
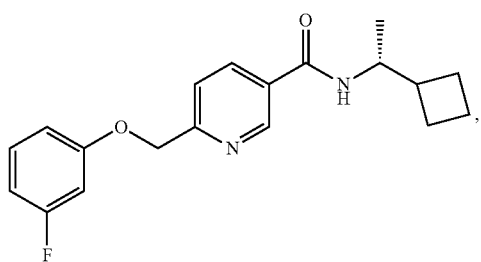
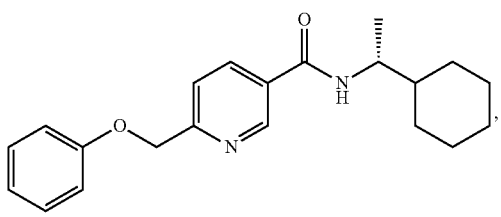
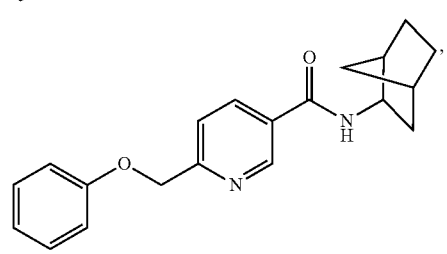
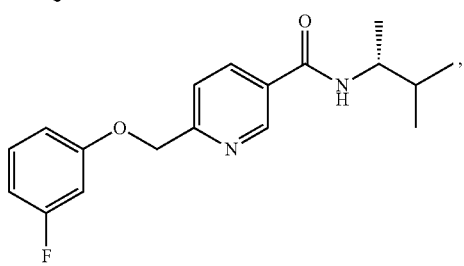
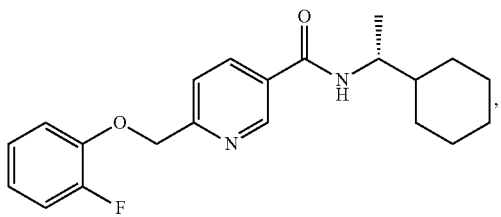
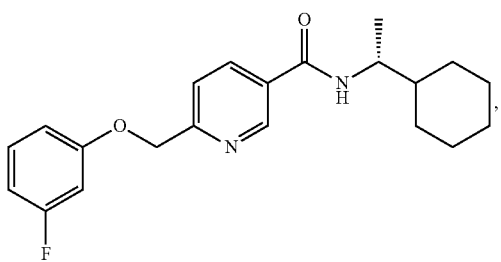
30
-continued
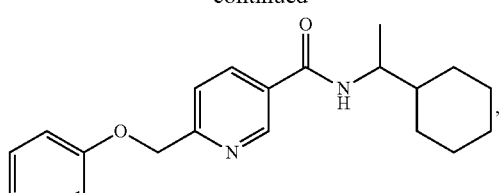
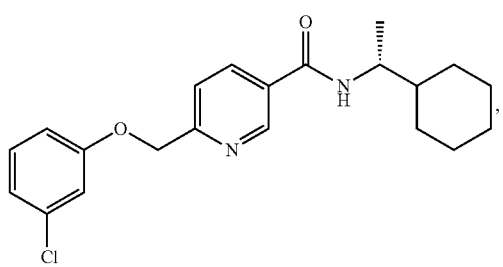
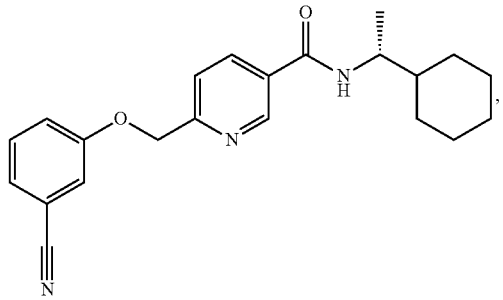
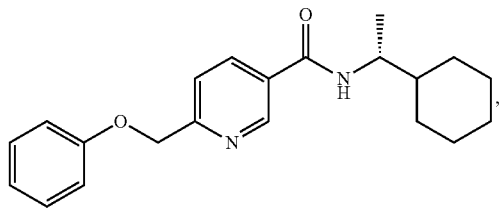
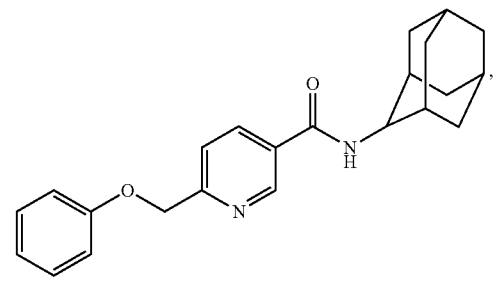
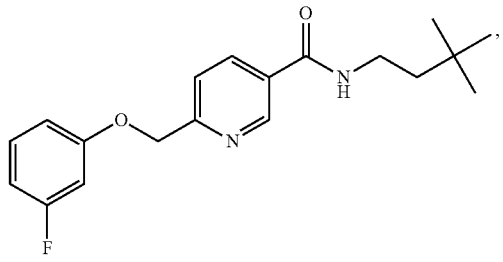

31
-continued
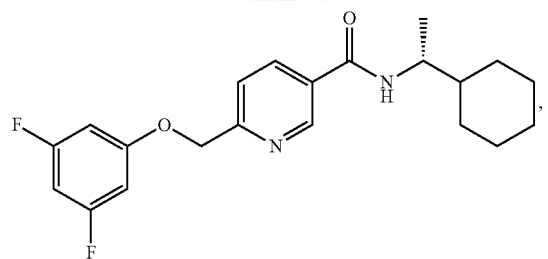
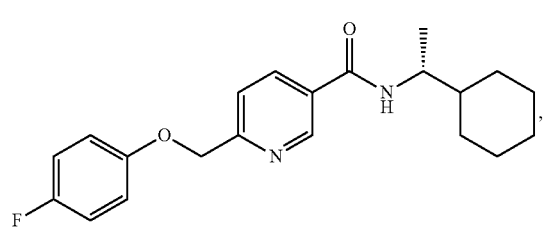
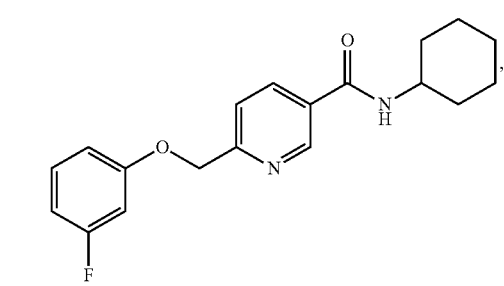
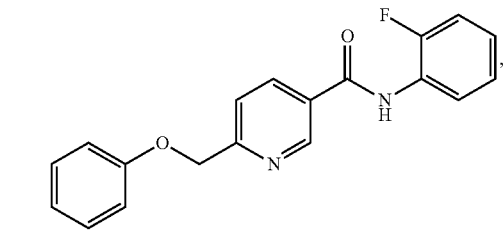
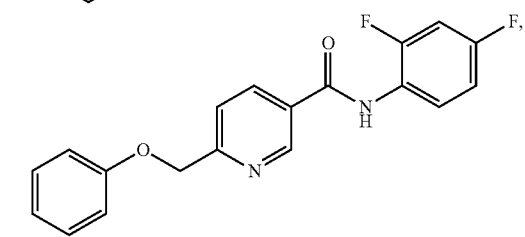
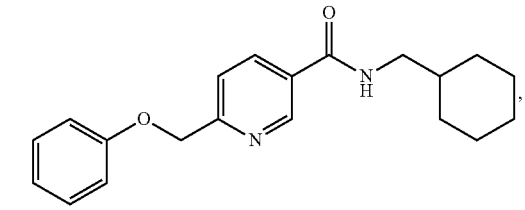
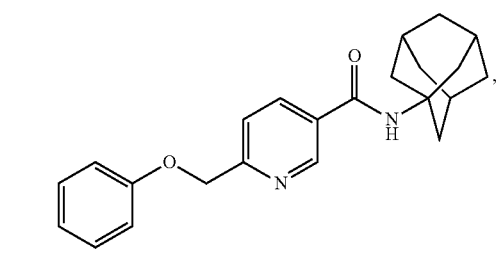
32
-continued
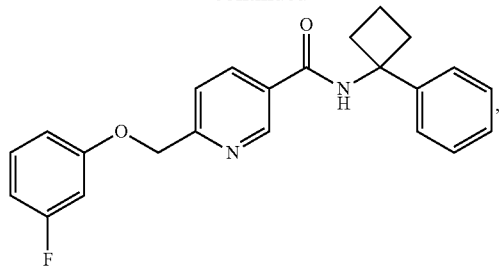
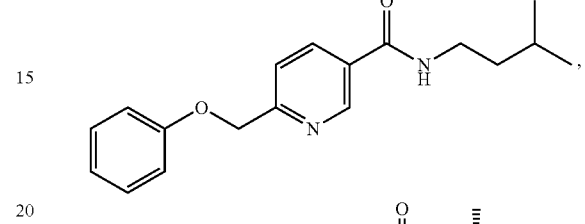
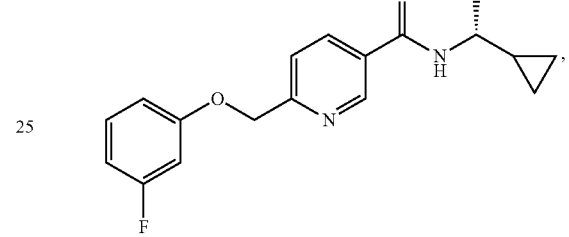
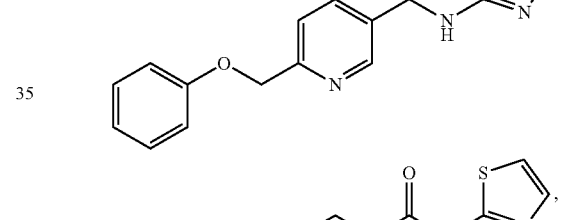
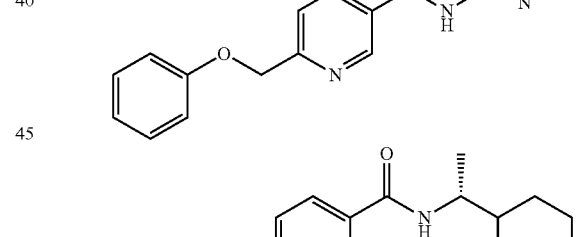
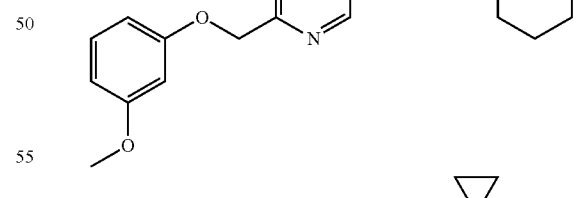
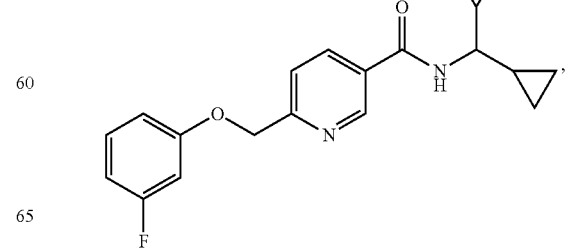

33
-continued
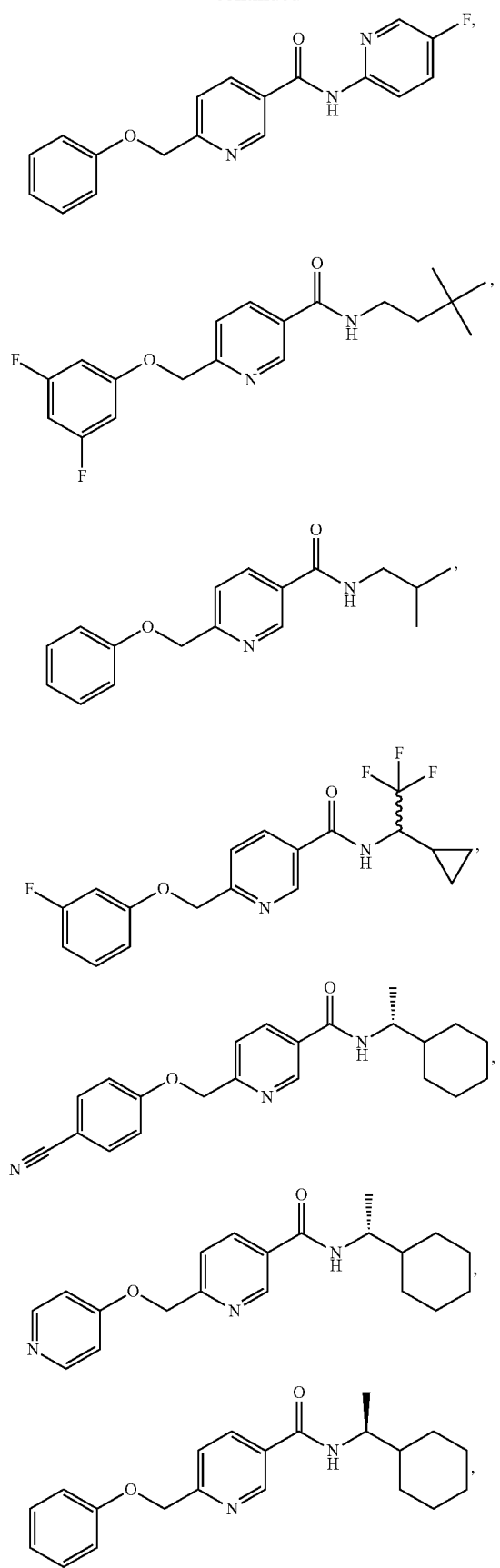
34
-continued
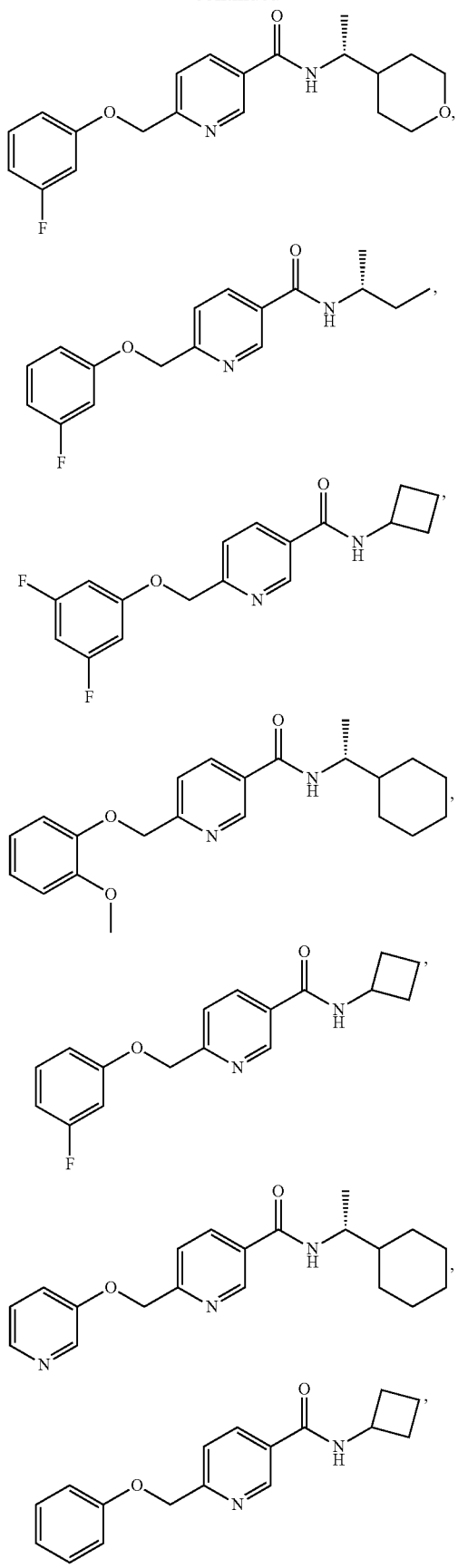

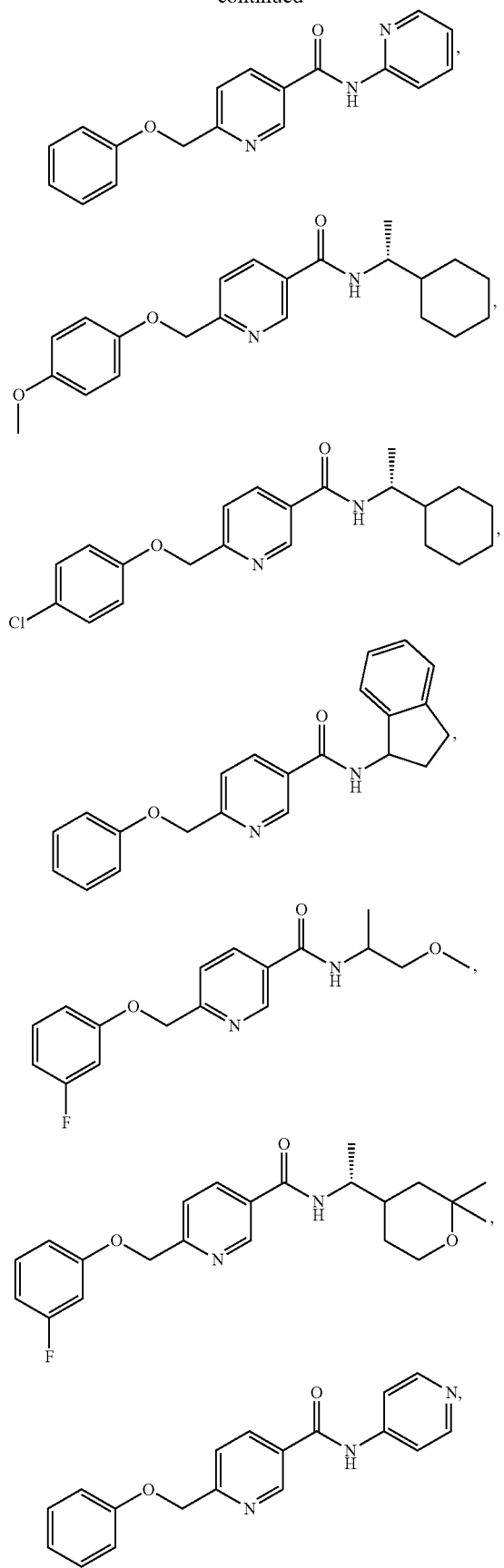
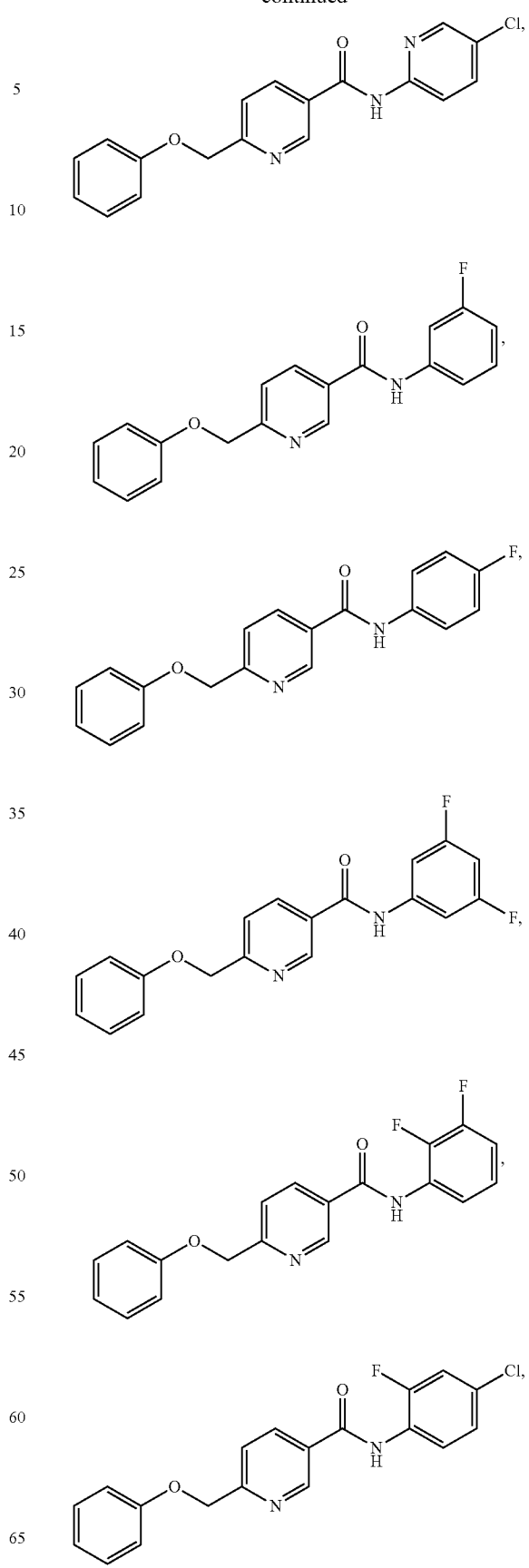

37
-continued
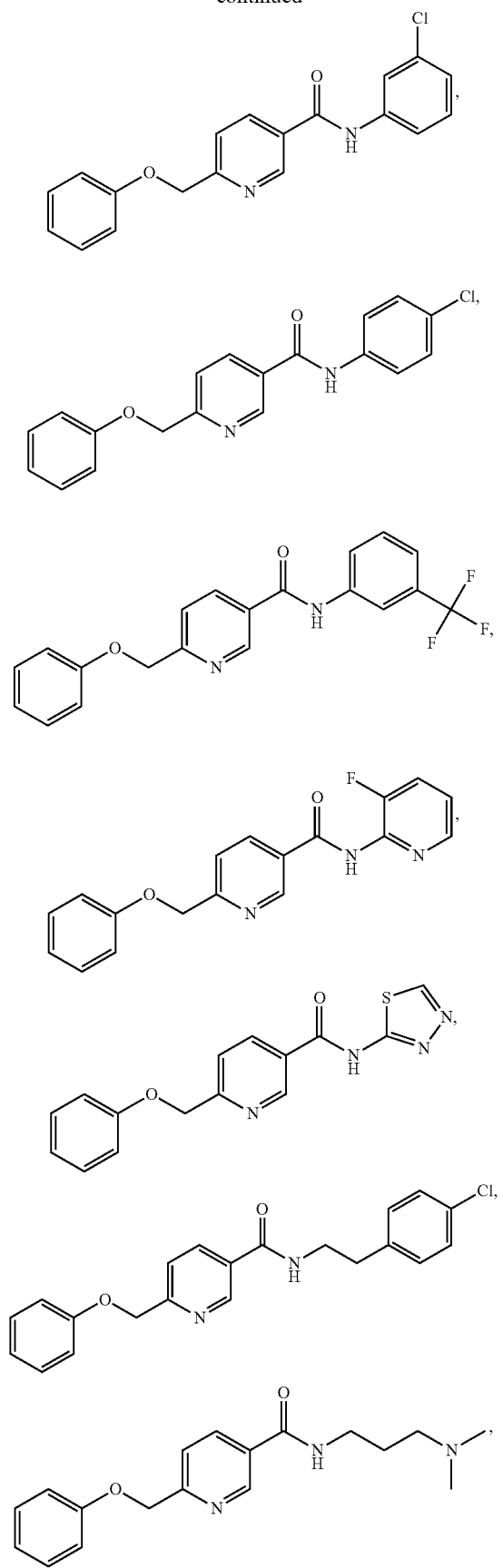
38
-continued
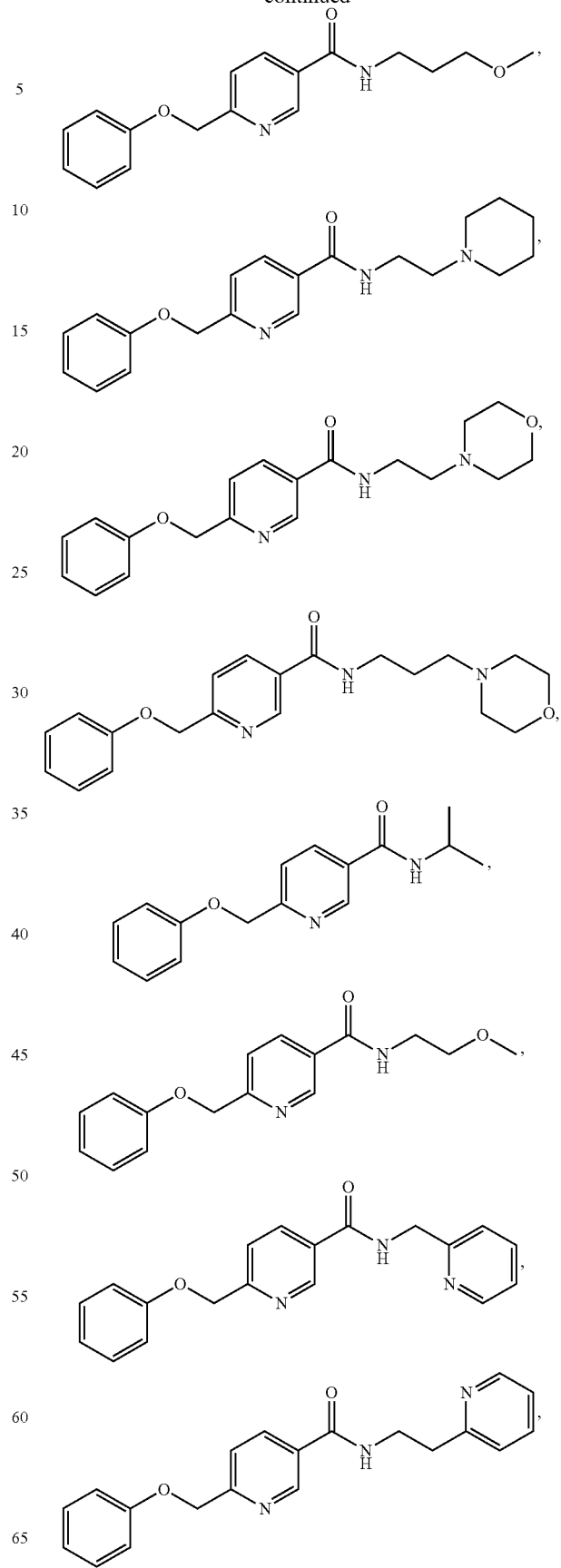

39
-continued
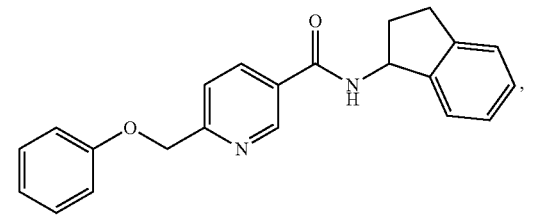
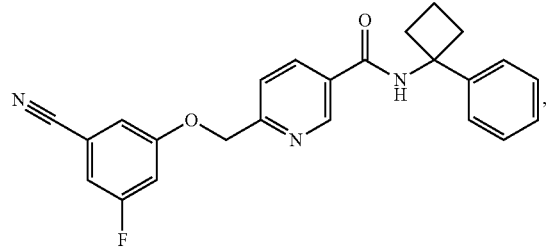
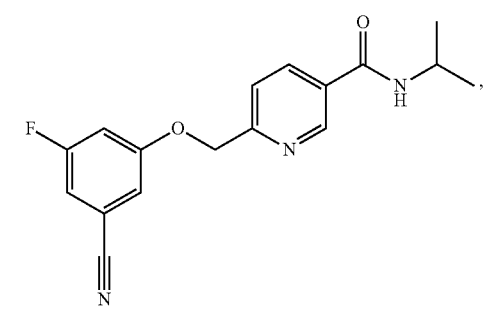
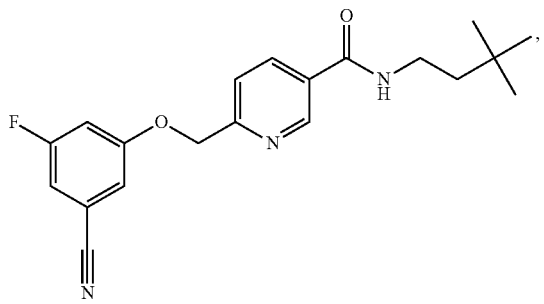
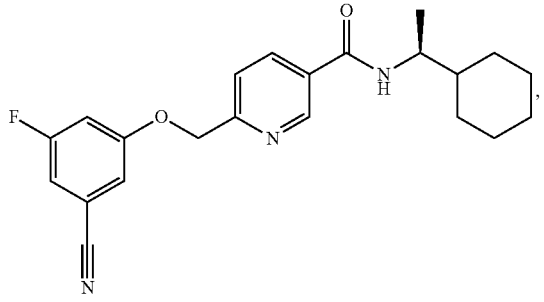
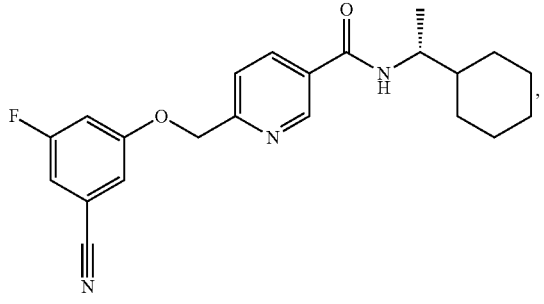
40
-continued
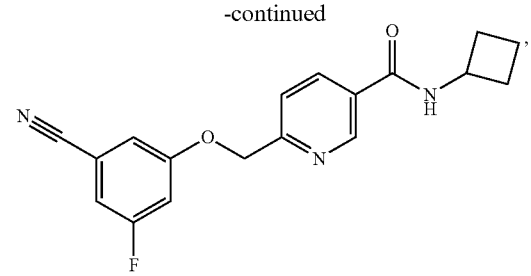
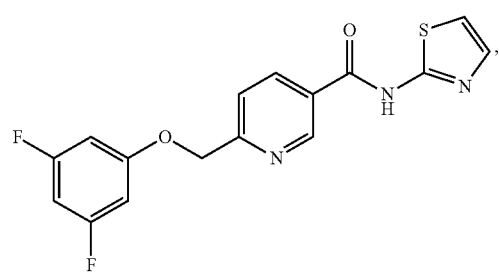
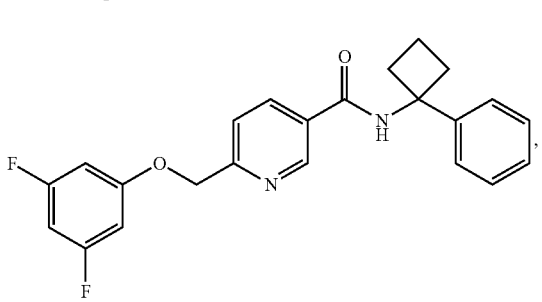
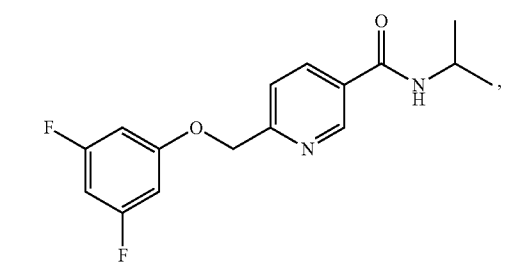
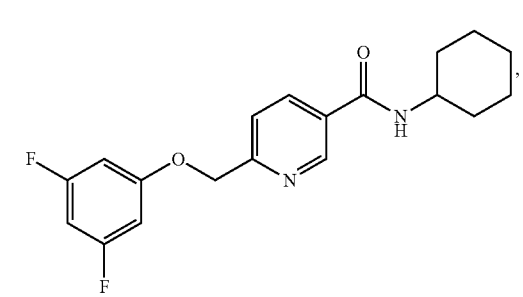
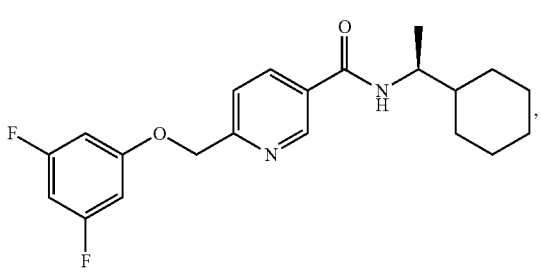

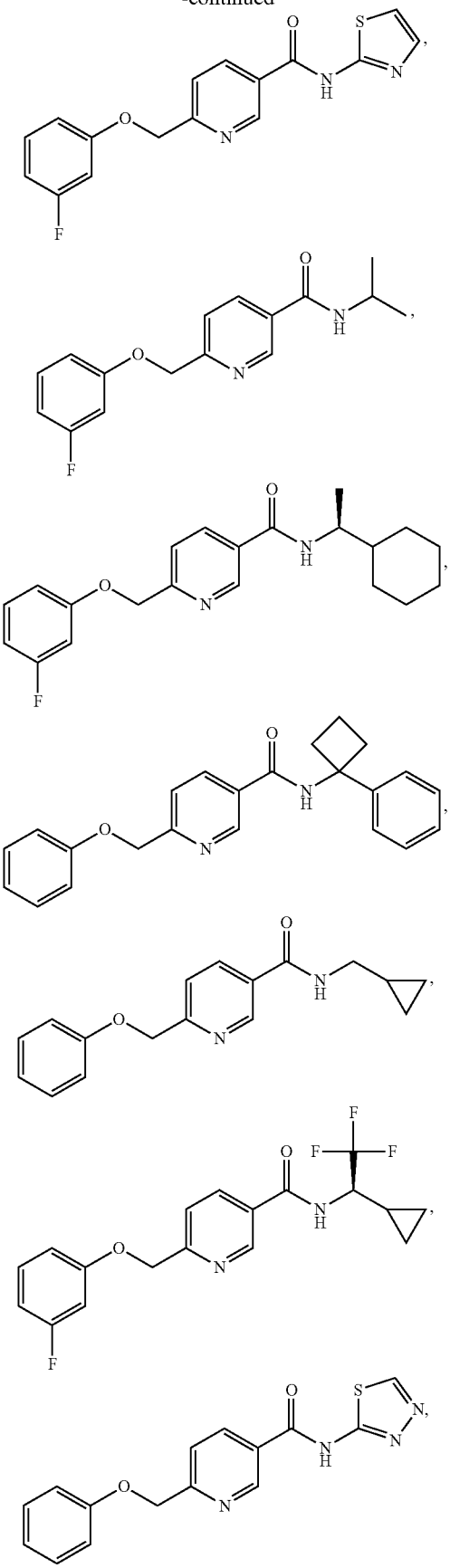
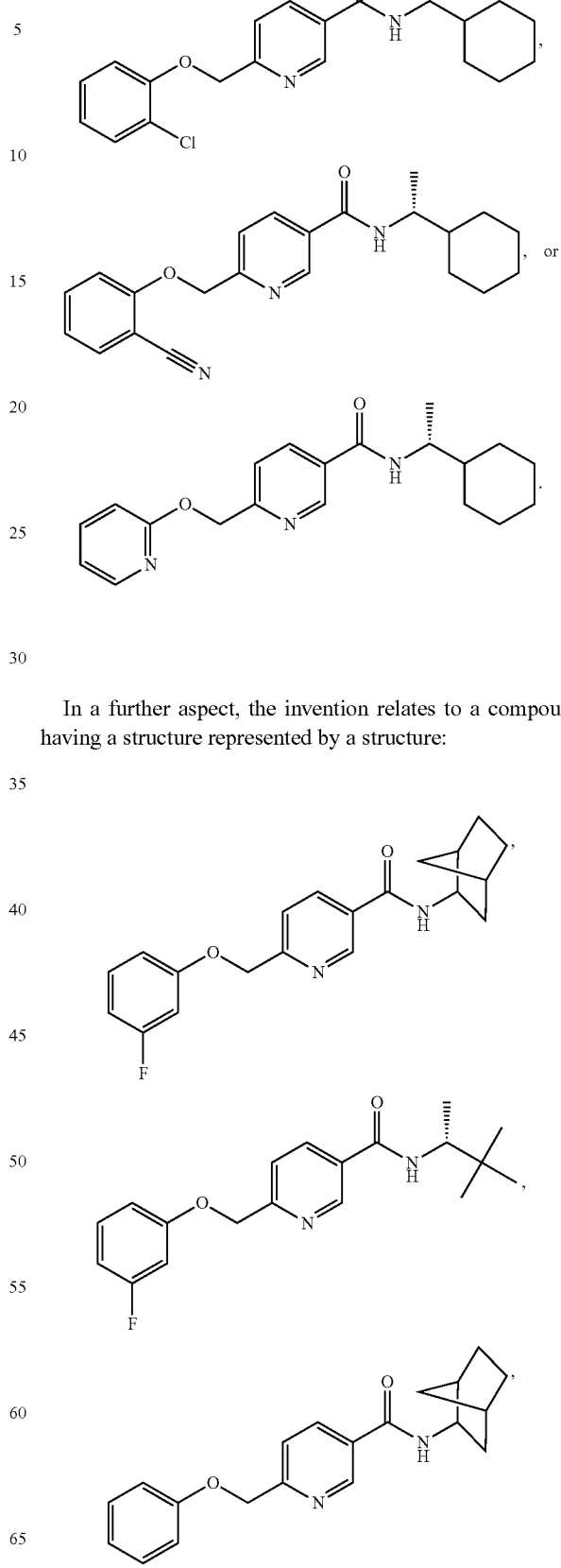
In a further aspect, the invention relates to a compound having a structure represented by a structure:

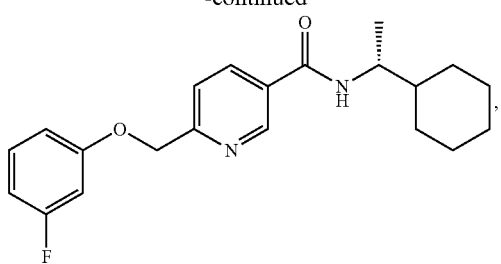
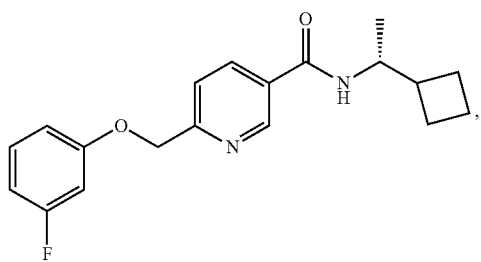
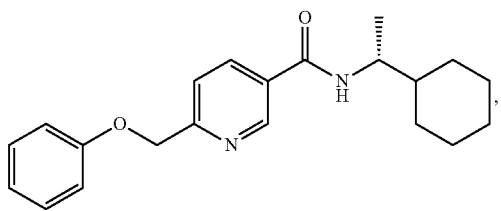
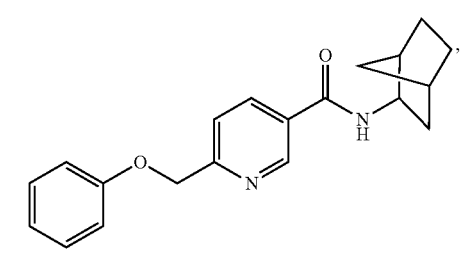
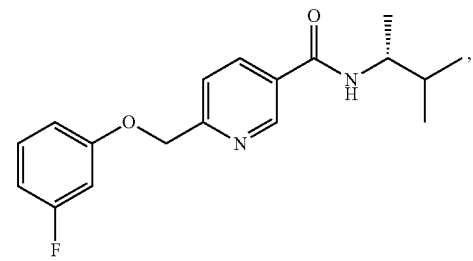
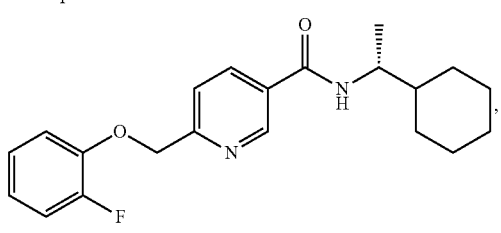
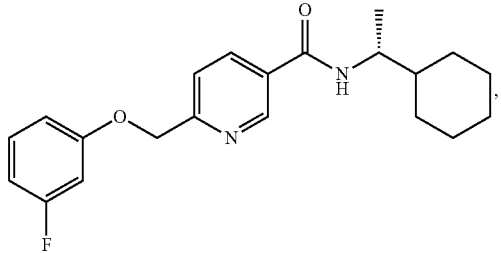
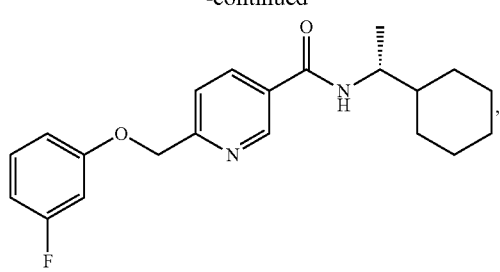
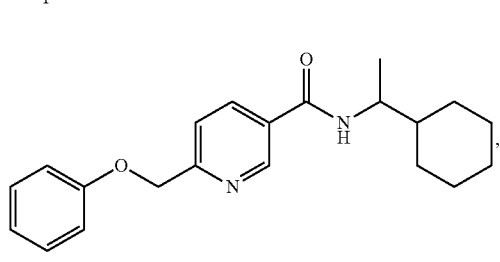
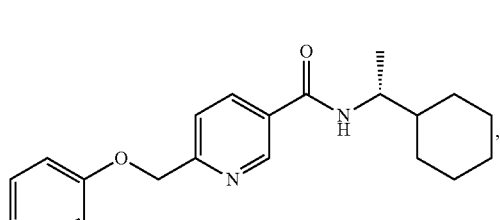
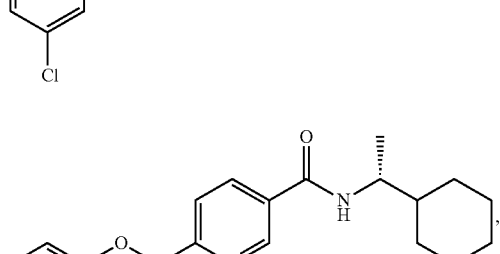
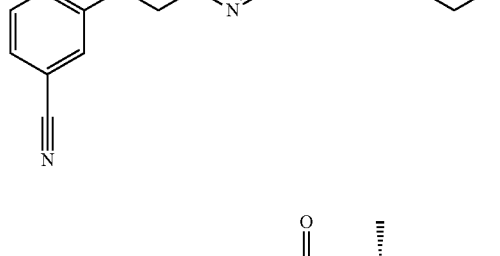
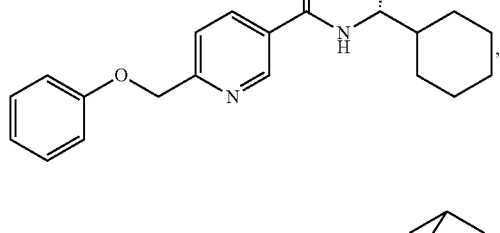
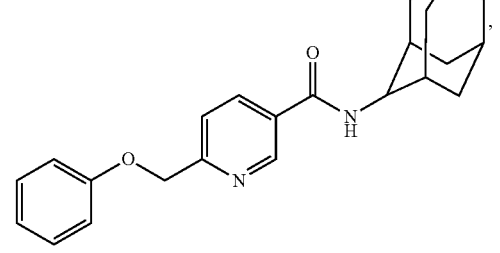

-continued

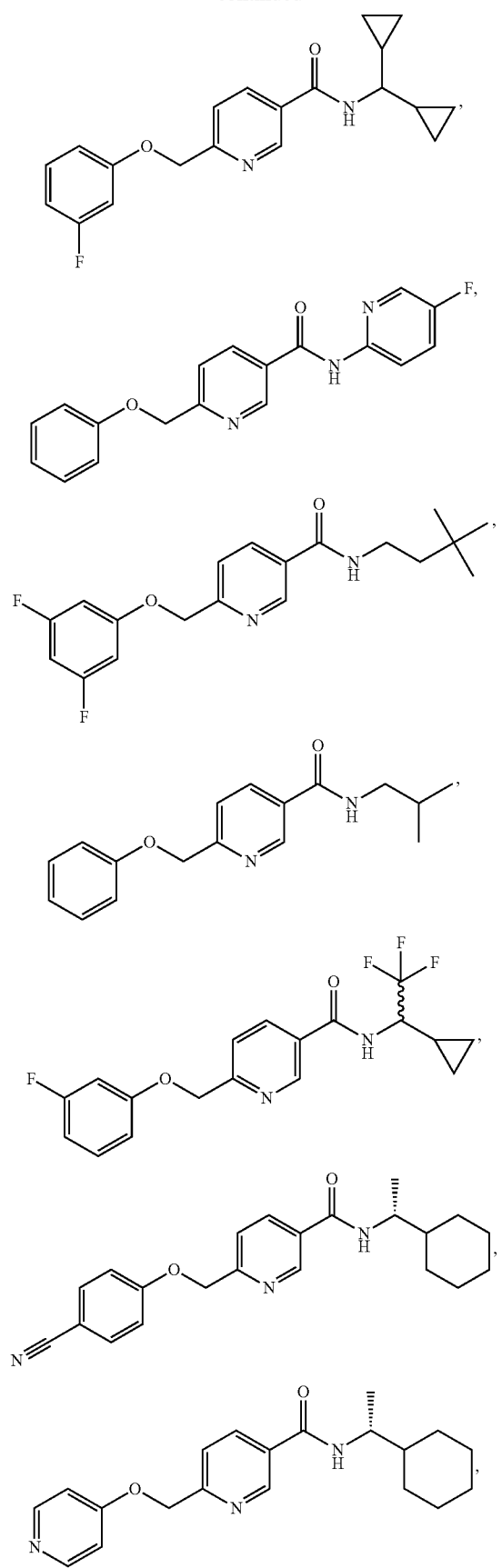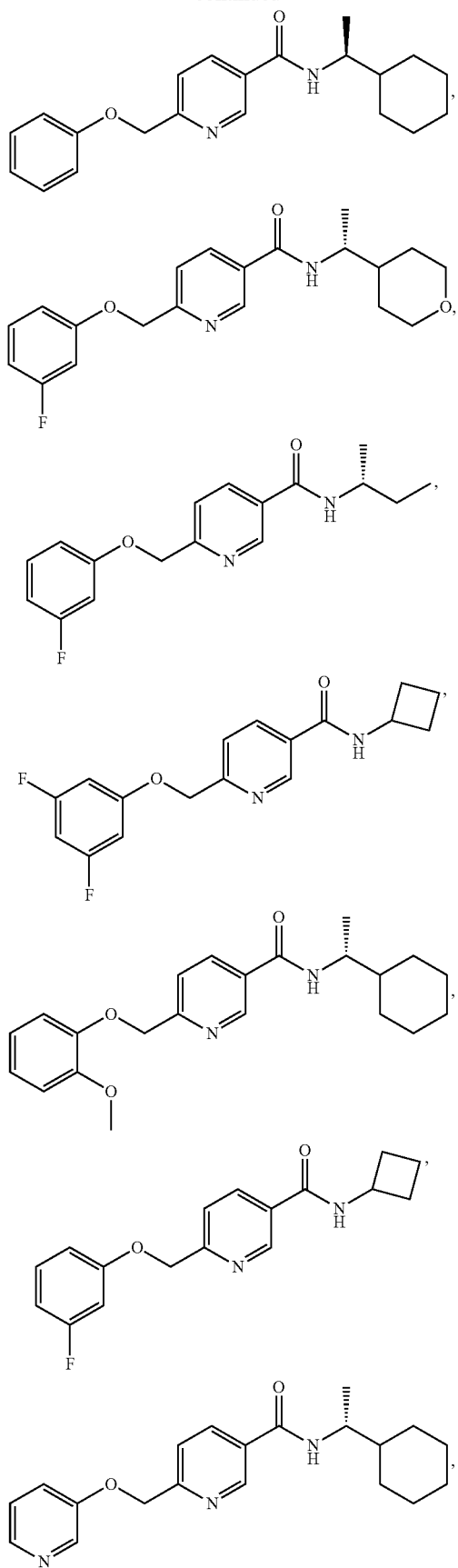

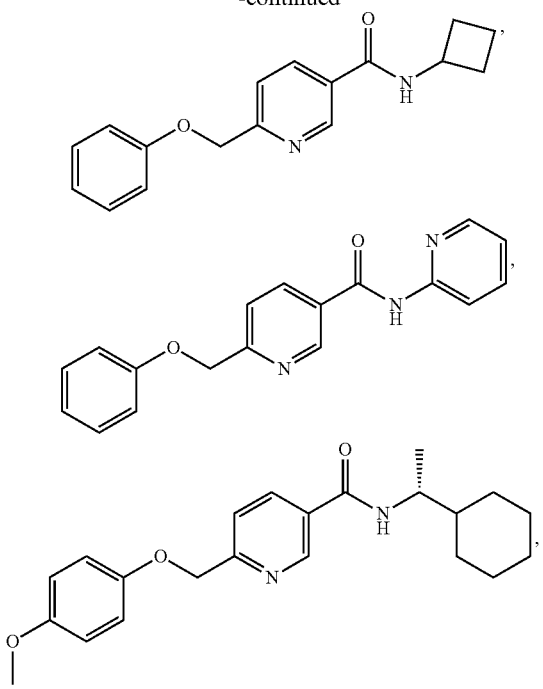
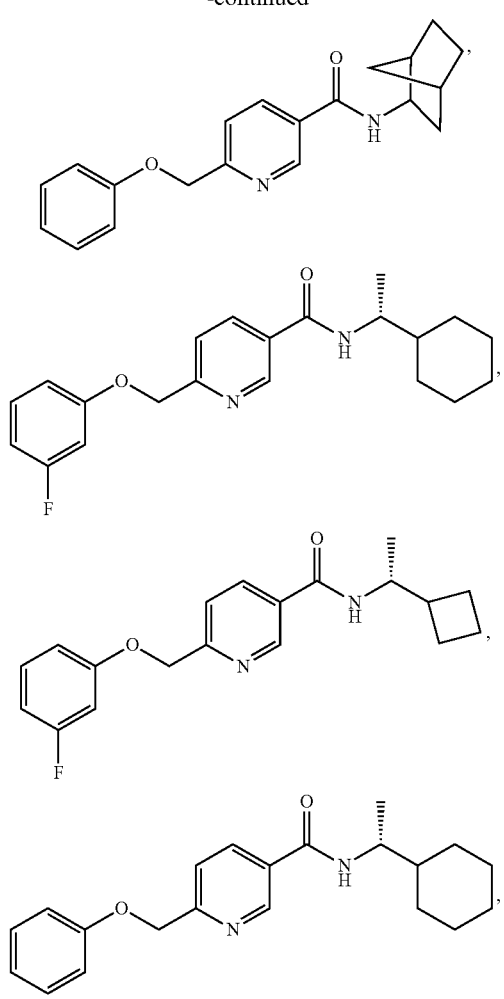
In a further aspect, the invention relates to a compound having a structure represented by a structure:
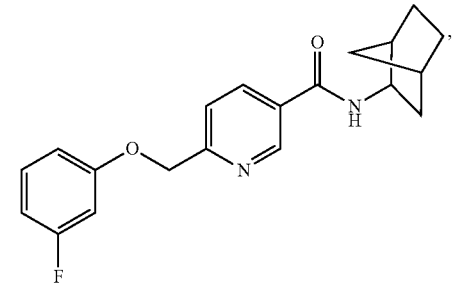
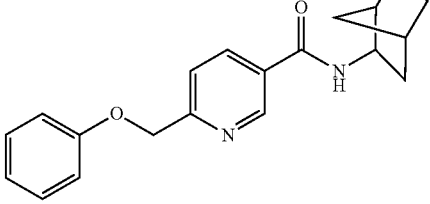
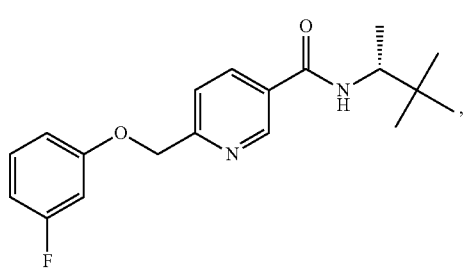
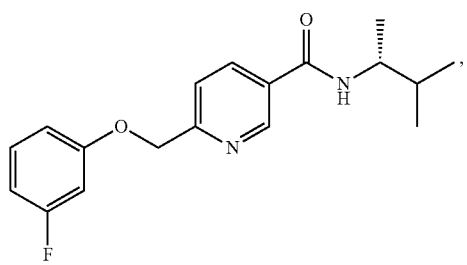
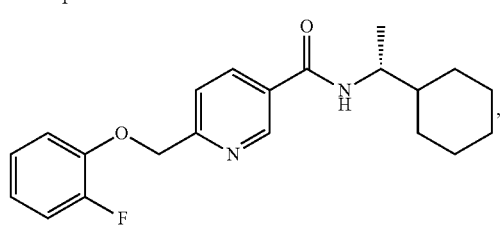

51
-continued
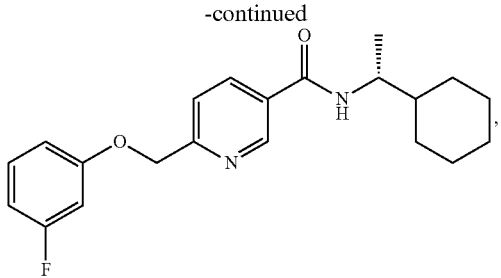
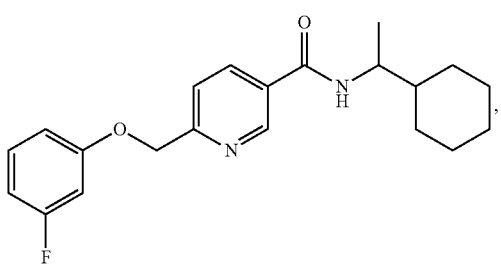
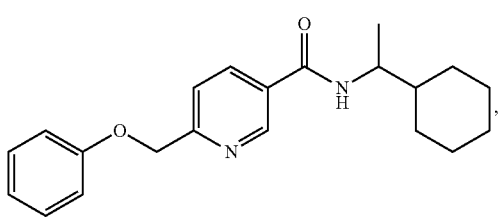
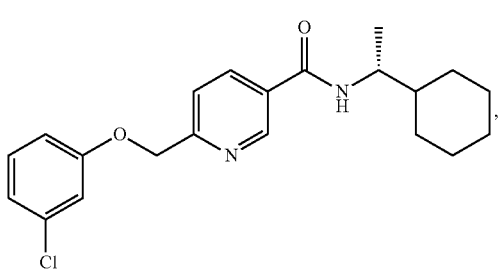
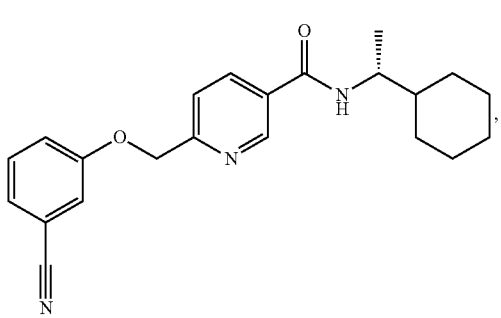
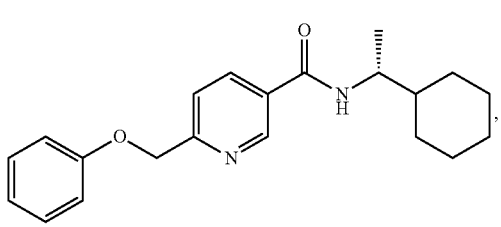
52
-continued
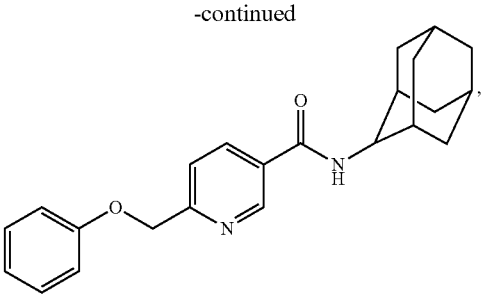
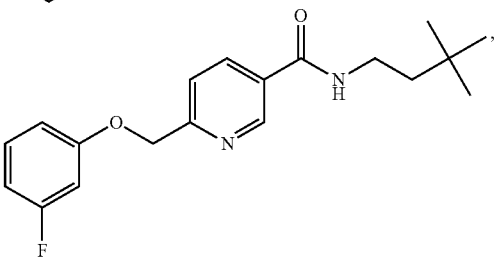
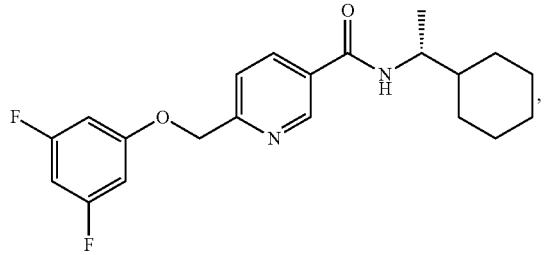
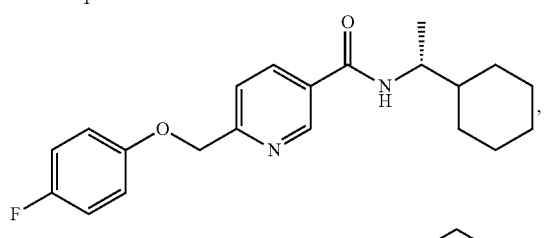
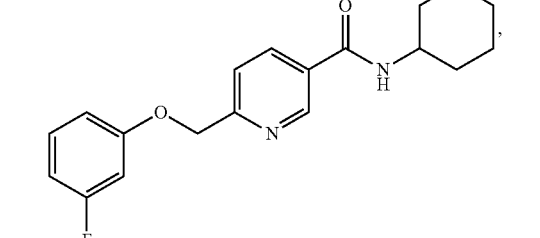
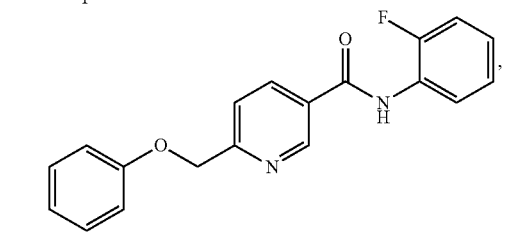
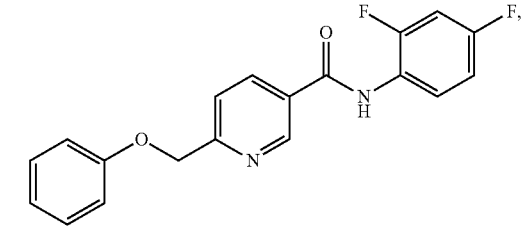

53
-continued
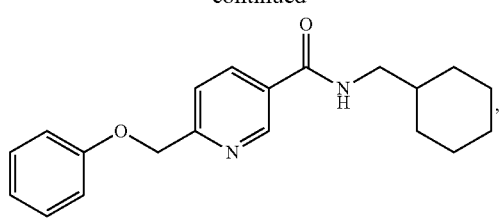
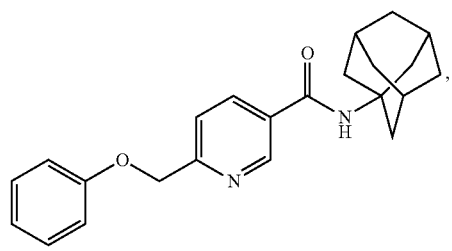
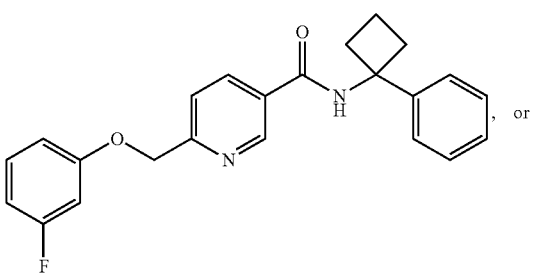, or
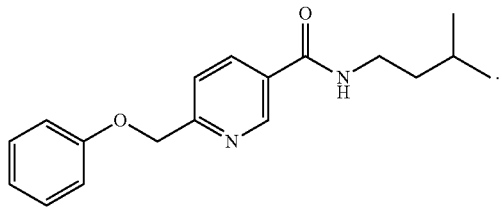
In a further aspect, the invention relates to a compound having a structure represented by a structure:
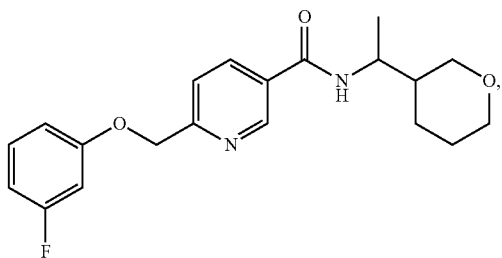
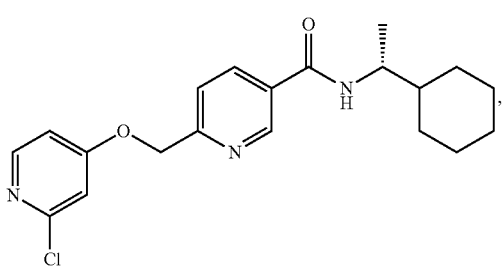
54
-continued
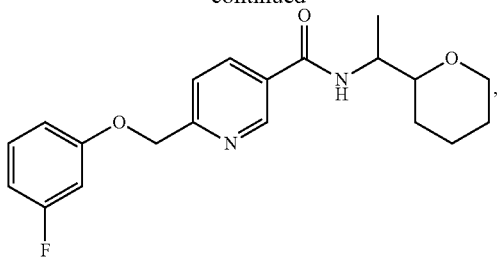
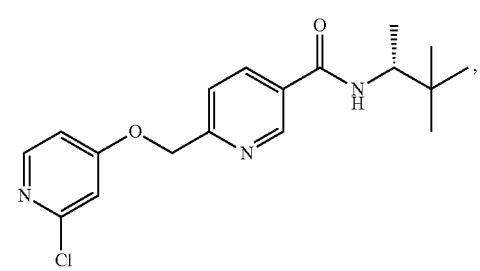
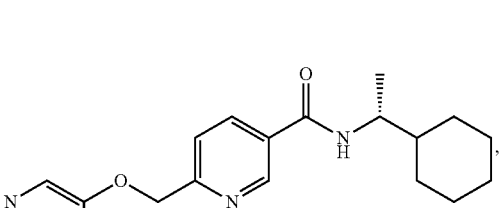
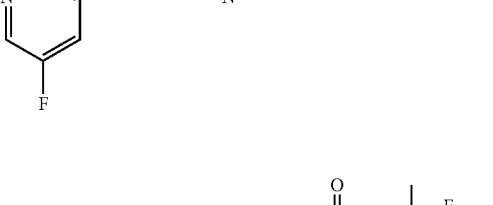
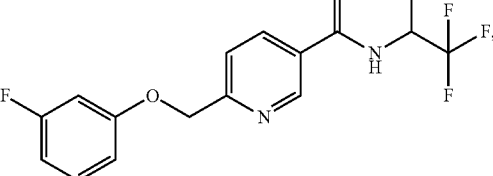
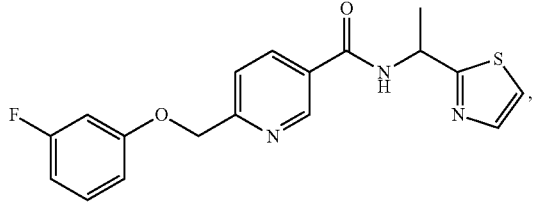
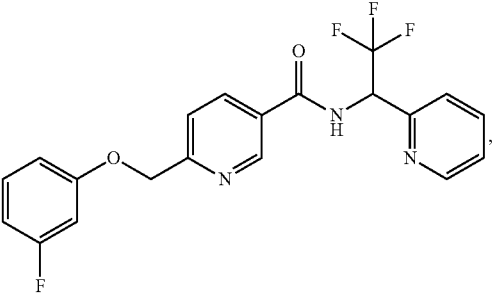

55
-continued
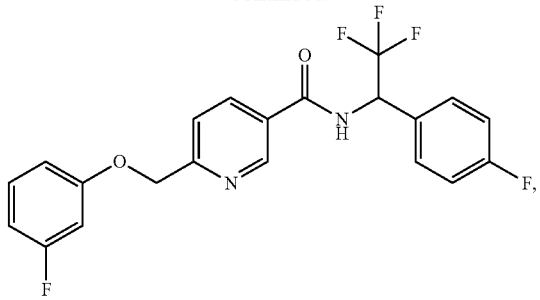
56
-continued
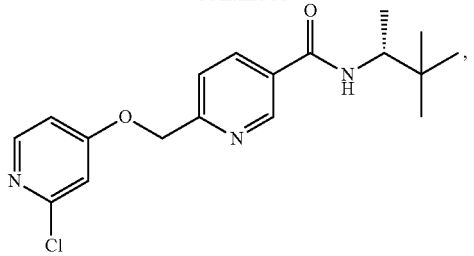
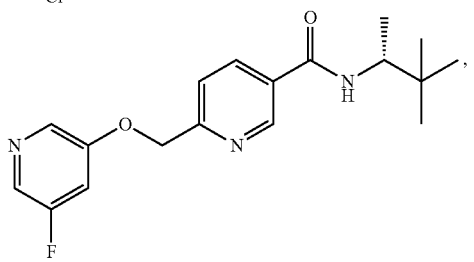
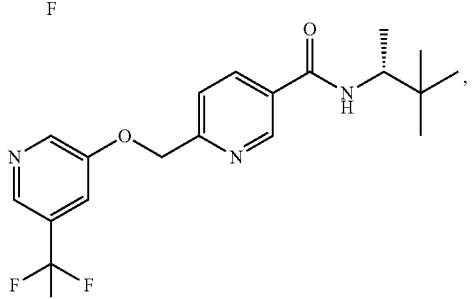
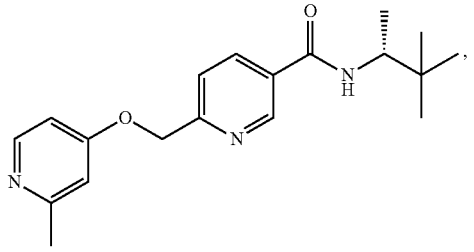
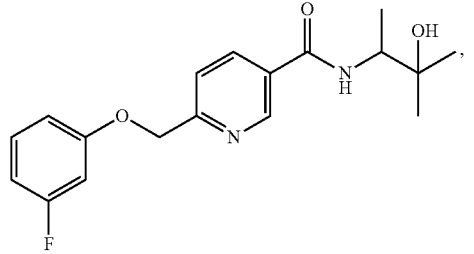
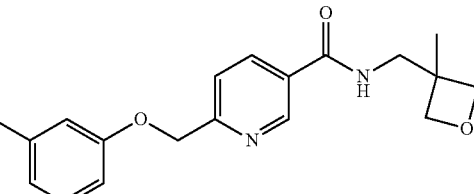
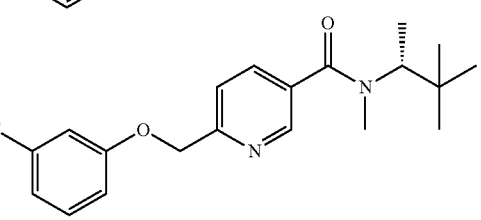

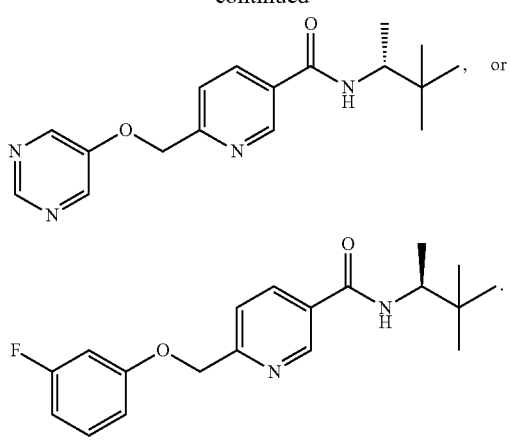
, or
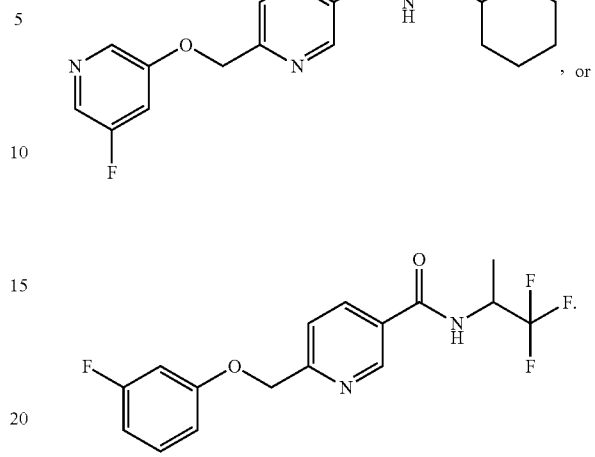
In a further aspect, the invention relates to a compound having a structure represented by a structure:
In a further aspect, the invention relates to a compound having a structure represented by a structure:
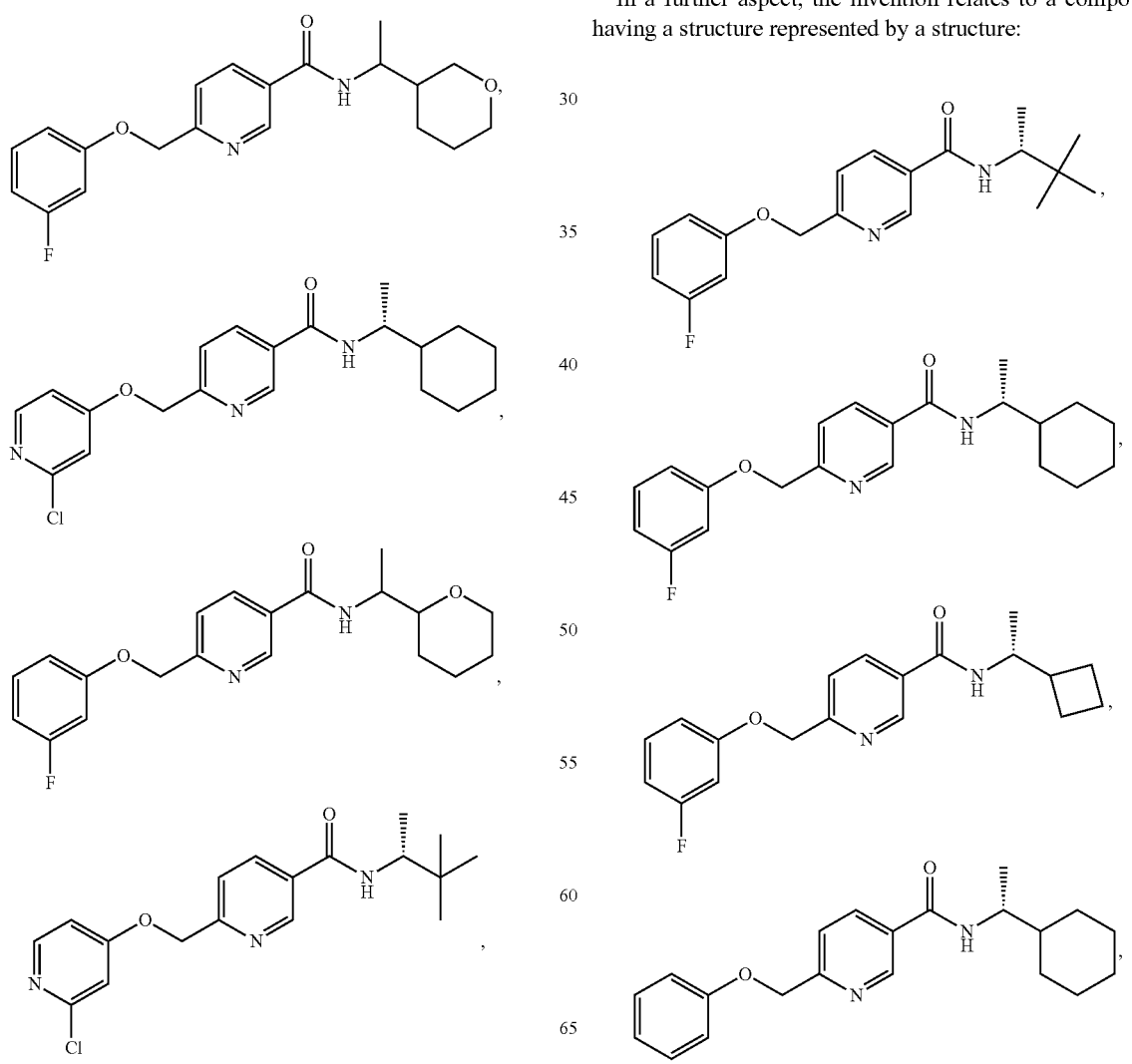

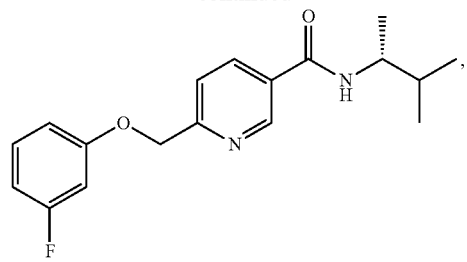
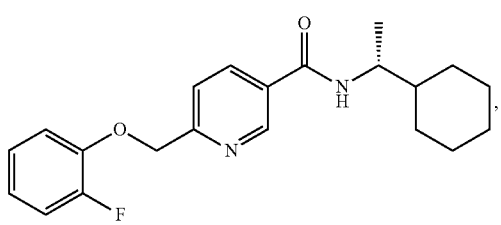
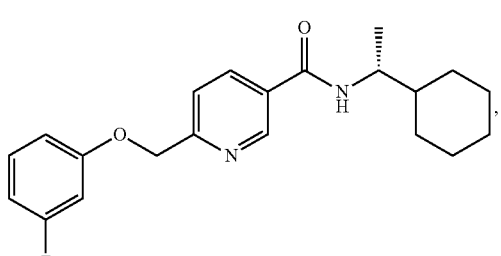
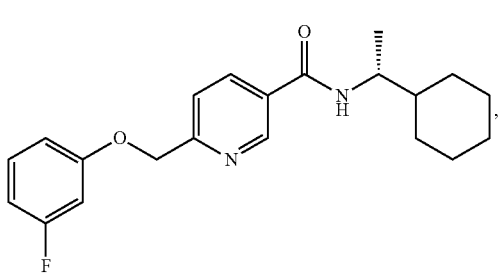
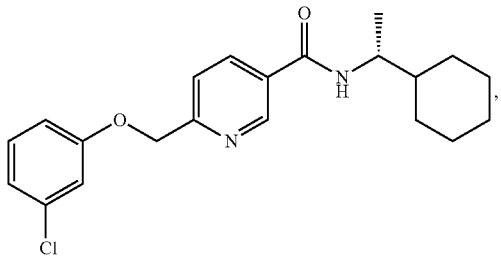
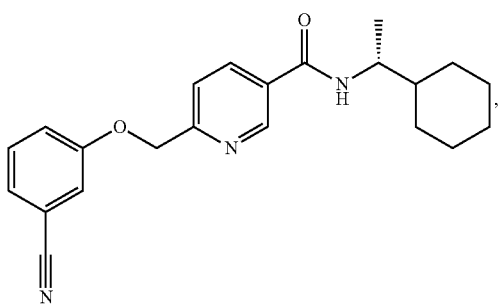
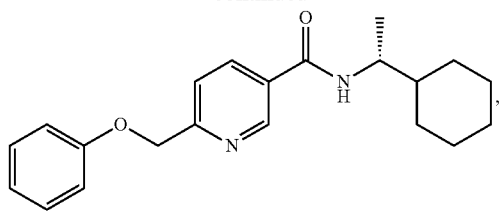
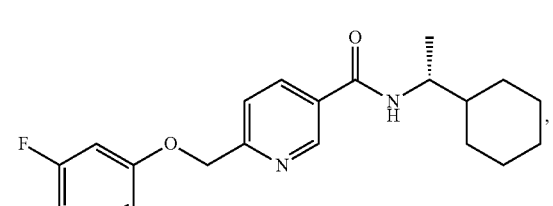
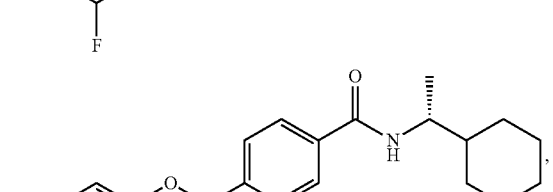
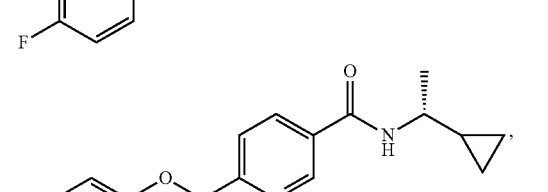
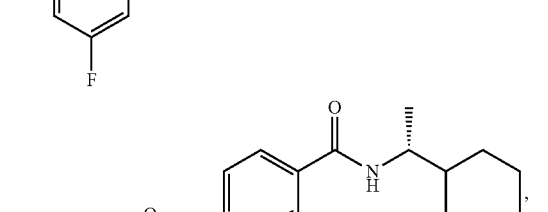
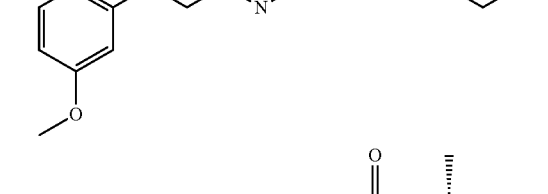
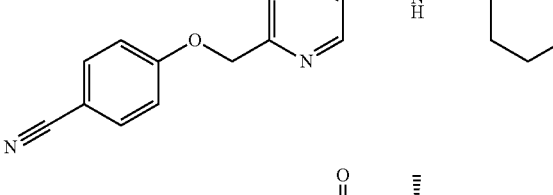
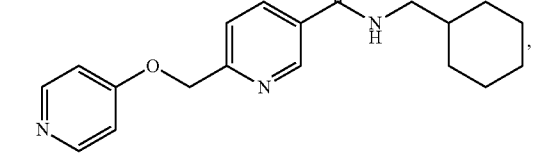

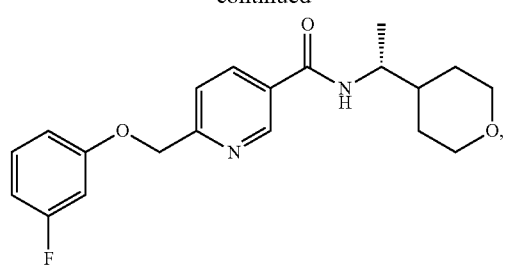
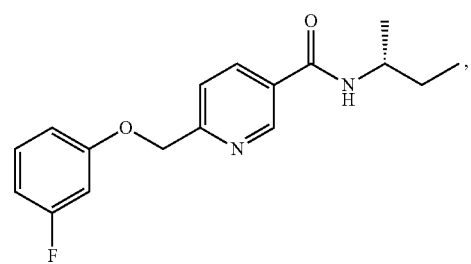
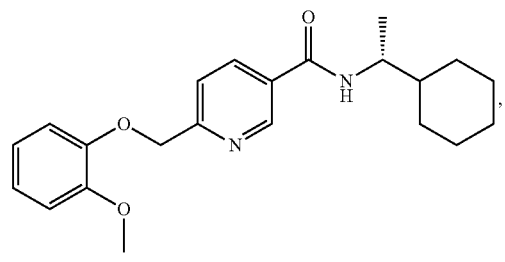
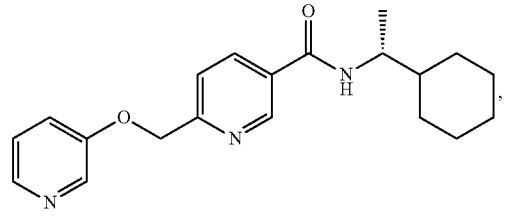
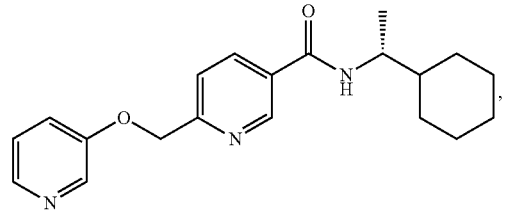
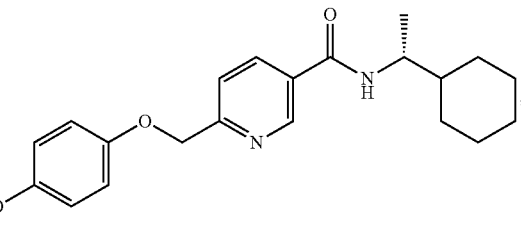
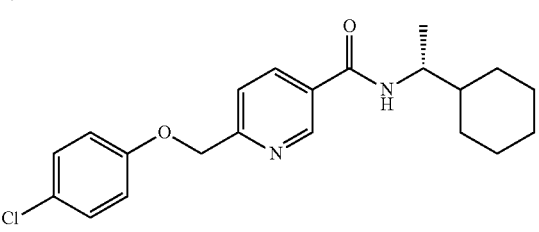
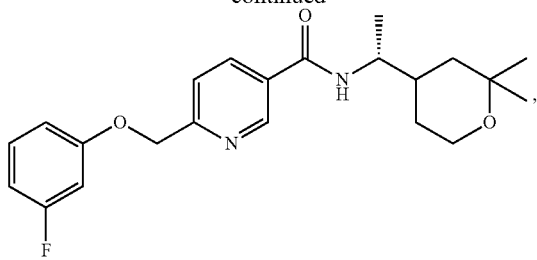
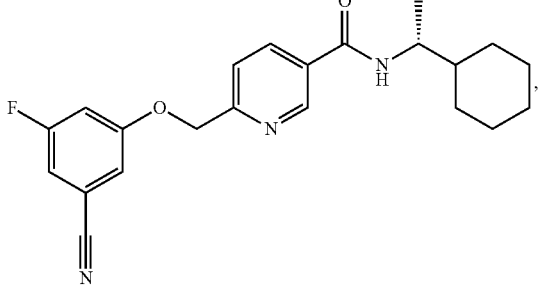
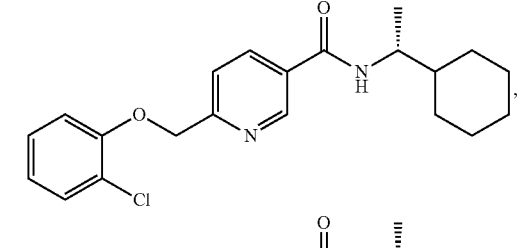
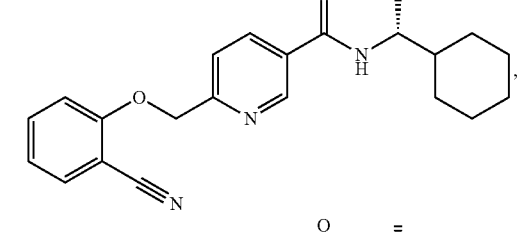
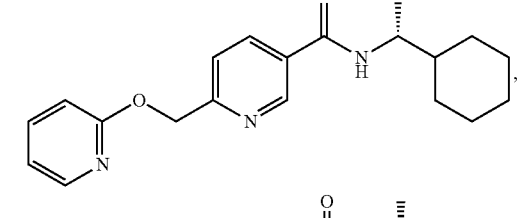
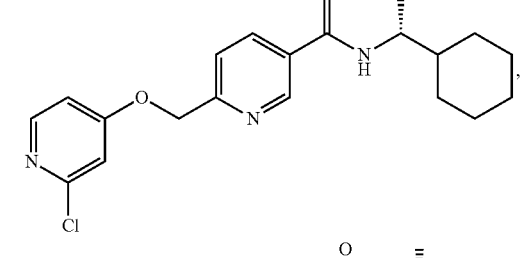
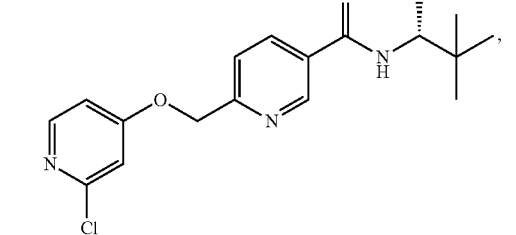

63
-continued
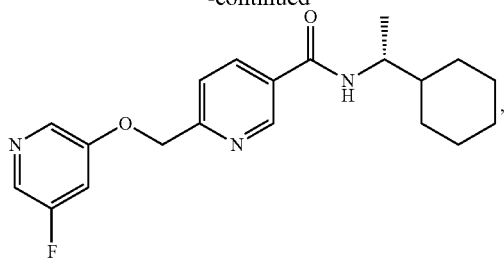
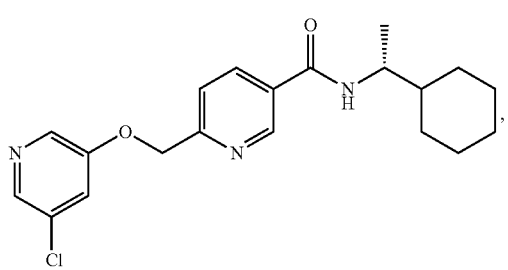
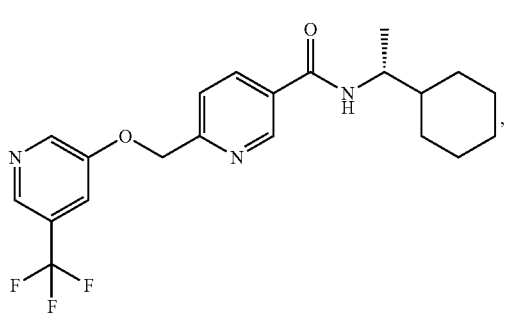
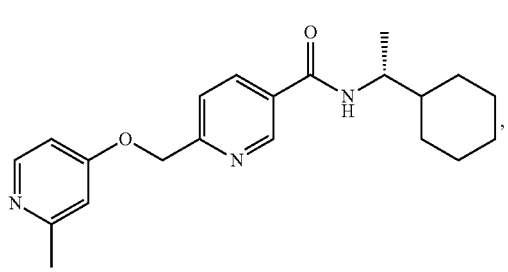
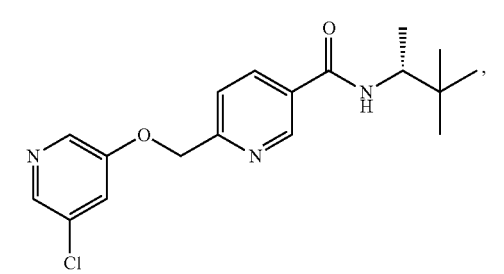
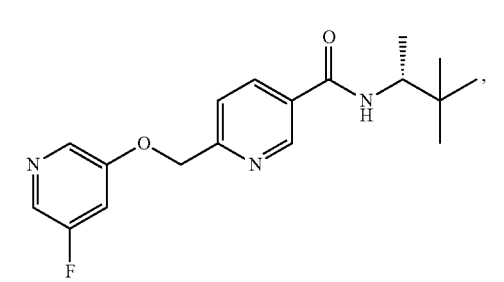
64
-continued
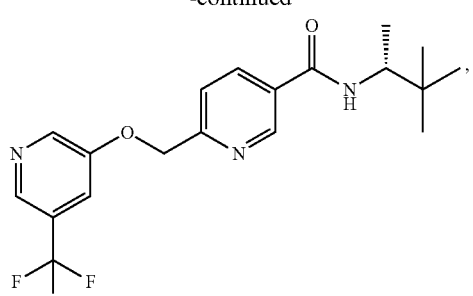
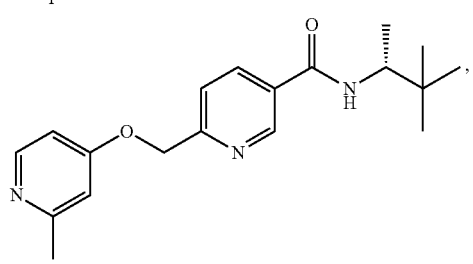
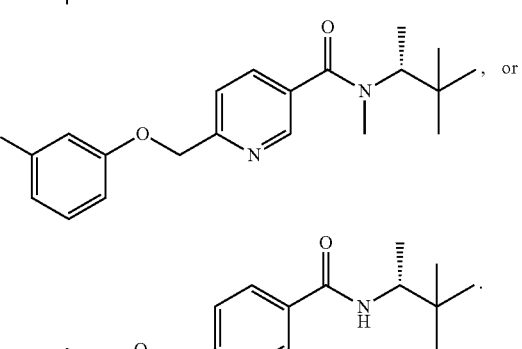, or
In a further aspect, the invention relates to a compound having a structure represented by a structure:
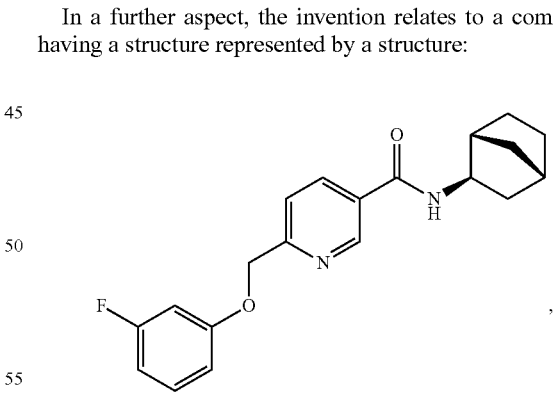
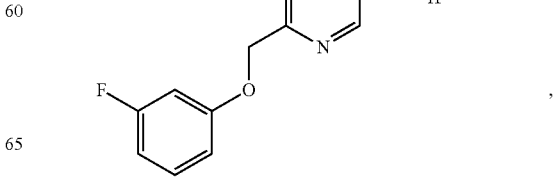

65

-continued

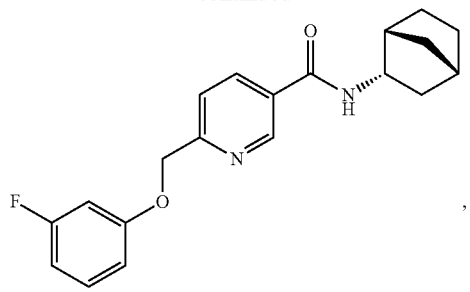
,

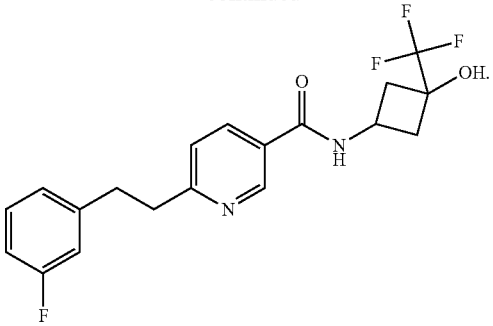 [SMILES: O=C(NC1CC(O)(C(F)(F)F)C1)c1ccc(CCc2cccc(F)c2)nc1]
,

66

-continued

[structure]
,

[structure]

[structure] OH, or

[structure]

It is contemplated that one or more compounds can optionally be omitted from the disclosed invention.

3. Activity

Generally, the disclosed compounds exhibit potentiation of mGluR5 response to glutamate as an increase in response to non-maximal concentrations of glutamate in human embryonic kidney cells transfected with rat mGluR5 in the presence of the compound, compared to the response to glutamate in the absence of the compound. For example, a compound can exhibit positive allosteric modulation of mGluR5 (e.g., rmGluR5) with an $EC_{50}$ of less than about 10,000 nM, of less than about 5,000 nM. of less than about 1,000 nM, of less than about 500 nM, or of less than about 100 nM. Alternatively, the disclosed compounds exhibit potentiation of mGluR5 response to glutamate as an increase in response to non-maximal concentrations of glutamate in human embryonic kidney cells transfected with human mGluR5 (H10H cell line) in the presence of the compound, compared to the response to glutamate in the absence of the compound. For example, a compound can exhibit positive allosteric modulation of mGluR5 (e.g., hmGluR5) with an $EC_{50}$ of less than about 10,000 nM, of less than about 5,000 nM. of less than about 1,000 nM, of less than about 500 nM, or of less than about 100 nM.

$EC_{50}$ data for certain exemplified compounds are tabulated in Table 1 and Table 2.

TABLE 1

| Structure | rmGlu5 PAM EC50 |
|---|---|
| [structure] | 7.59E-08 |

TABLE 1-continued
| Structure | rmGlu5 PAM EC50 |
|---|---|
| 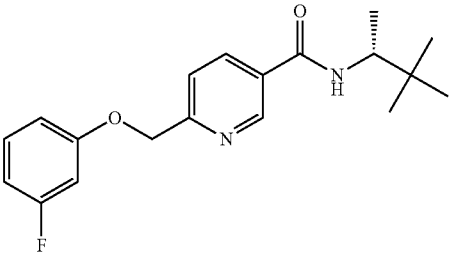 [SMILES: C[C@@H](NC(=O)c1ccc(COc2cccc(F)c2)nc1)C(C)(C)C] | 8.13E-08 |
| 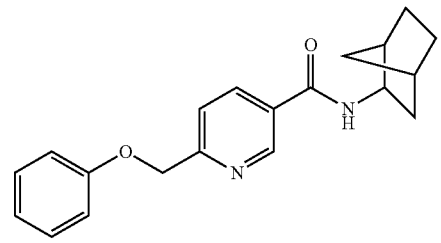 [SMILES: O=C(NC1CC2CCC1C2)c1ccc(COc2ccccc2)nc1] | 1.20E-07 |
| 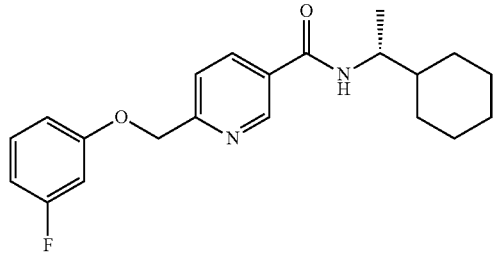 [SMILES: C[C@@H](NC(=O)c1ccc(COc2cccc(F)c2)nc1)C1CCCCC1] | 1.30E-07 |
| 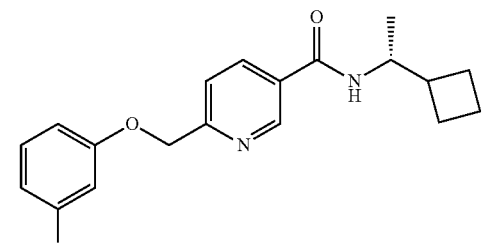 | 1.38E-07 |
| 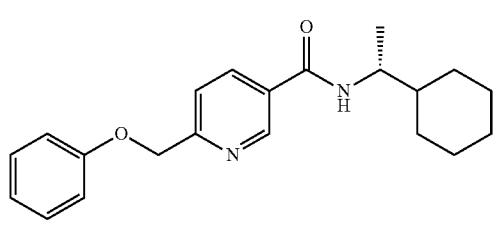 [SMILES: C[C@@H](NC(=O)c1ccc(COc2ccccc2)nc1)C1CCCCC1] | 1.46E-07 |
| 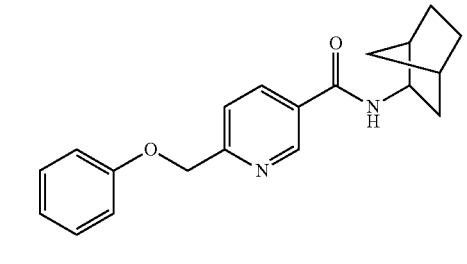 [SMILES: O=C(NC1CC2CCC1C2)c1ccc(COc2ccccc2)nc1] | 1.51E-07 |

TABLE 1-continued
| Structure | rmGlu5 PAM EC50 |
|---|---|
| 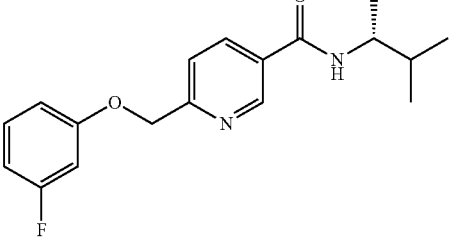 | 1.58E-07 |
| 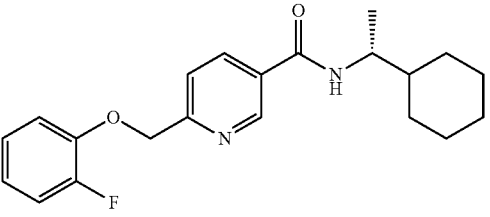 [SMILES: C[C@@H](NC(=O)c1ccc(COc2ccccc2F)nc1)C1CCCCC1] | 1.60E-07 |
| 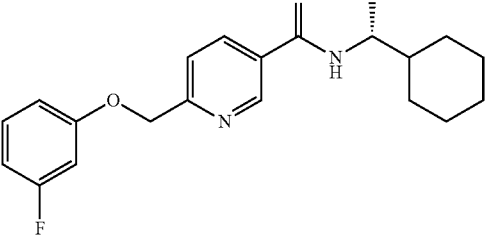 | 1.70E-07 |
| 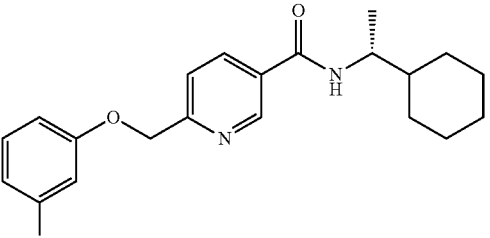 | 1.72E-07 |
| 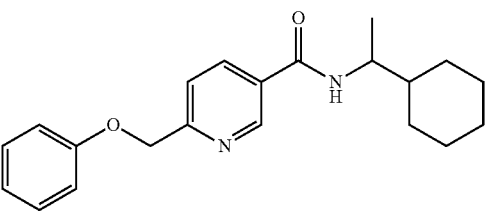 [SMILES: CC(NC(=O)c1ccc(COc2ccccc2)nc1)C1CCCCC1] | 1.88E-07 |
| 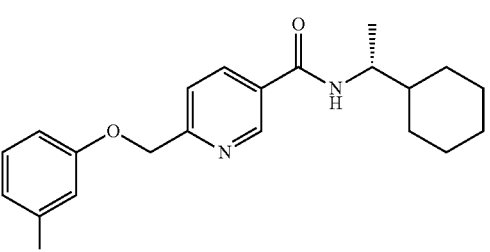 | 2.10E-07 |

TABLE 1-continued

| Structure | rmGlu5 PAM EC50 |
|---|---|
| 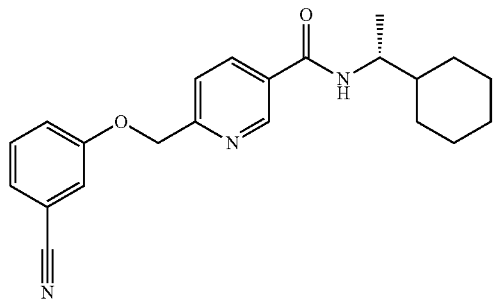 [SMILES: C[C@@H](NC(=O)c1ccc(COc2cccc(C#N)c2)nc1)C1CCCCC1] | 2.20E-07 |
| 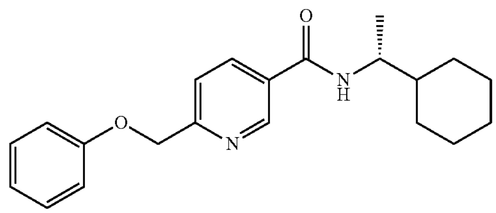 [SMILES: C[C@@H](NC(=O)c1ccc(COc2ccccc2)nc1)C1CCCCC1] | 2.57E-07 |
| 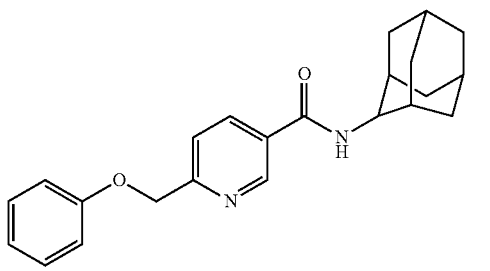 [SMILES: O=C(NC1C2CC3CC(C2)CC1C3)c1ccc(COc2ccccc2)nc1] | 2.88E-07 |
| 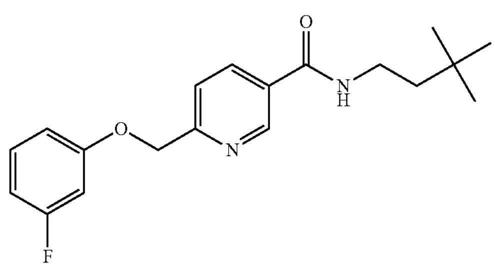 [SMILES: CC(C)(C)CCNC(=O)c1ccc(COc2cccc(F)c2)nc1] | 3.02E-07 |
| 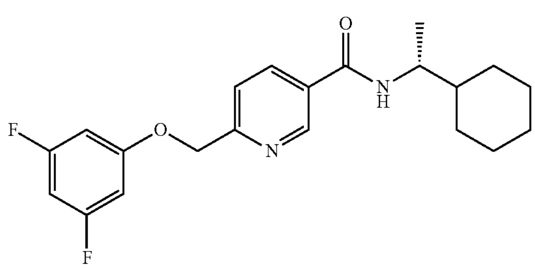 [SMILES: C[C@@H](NC(=O)c1ccc(COc2cc(F)cc(F)c2)nc1)C1CCCCC1] | 3.09E-07 |
| 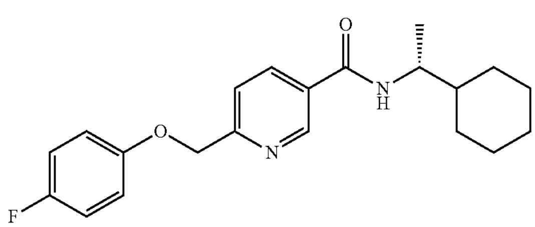 [SMILES: C[C@@H](NC(=O)c1ccc(COc2ccc(F)cc2)nc1)C1CCCCC1] | 3.60E-07 |

TABLE 1-continued

| Structure | rmGlu5 PAM EC50 |
|---|---|
| (3-fluorophenoxymethyl-pyridine-carboxamide, N-cyclohexyl) | 4.47E-07 |
| (phenoxymethyl-pyridine-carboxamide, N-(2-fluorophenyl)) | 5.01E-07 |
| (phenoxymethyl-pyridine-carboxamide, N-(2,4-difluorophenyl)) | 5.01E-07 |
| (phenoxymethyl-pyridine-carboxamide, N-cyclohexylmethyl) | 5.75E-07 |
| (phenoxymethyl-pyridine-carboxamide, N-adamantyl) | 6.03E-07 |
| (3-fluorophenoxymethyl-pyridine-carboxamide, N-(1-phenylcyclobutyl)) | 9.12E-07 |

TABLE 1-continued
| Structure | rmGlu5 PAM EC50 |
|---|---|
| 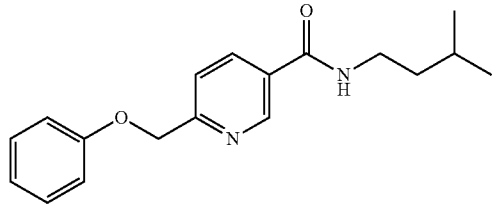 [SMILES: CC(C)CCNC(=O)c1ccc(COc2ccccc2)nc1] | 9.66E-07 |
| 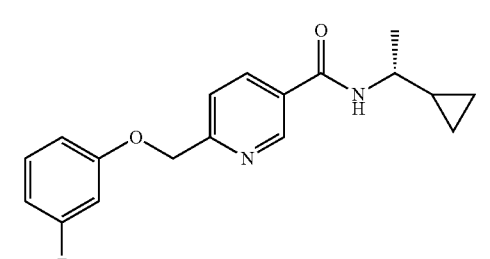 | 1.06E-06 |
| 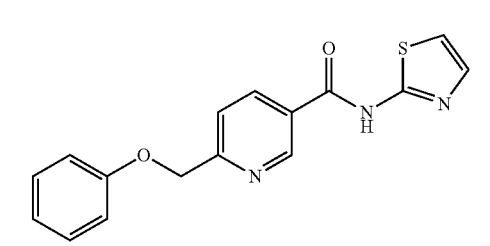 [SMILES: O=C(Nc1nccs1)c1ccc(COc2ccccc2)nc1] | 1.20E-06 |
| 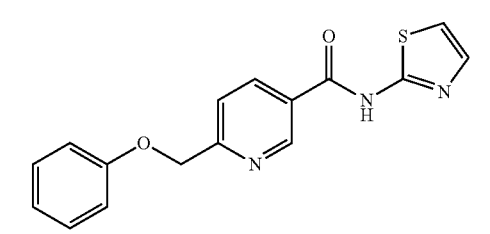 [SMILES: O=C(Nc1nccs1)c1ccc(COc2ccccc2)nc1] | 1.20E-06 |
| 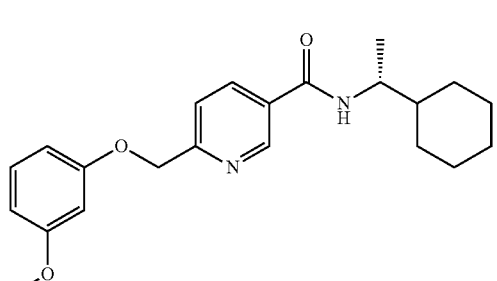 | 1.20E-06 |
| 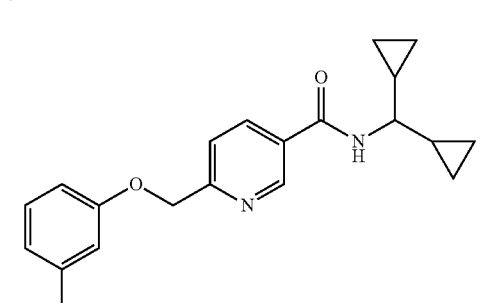 | 1.26E-06 |

TABLE 1-continued

| Structure | rmGlu5 PAM EC50 |
|---|---|
| 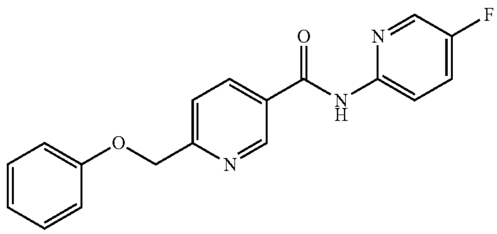 [SMILES: O=C(Nc1ccc(F)cn1)c1ccc(COc2ccccc2)nc1] | 1.51E-06 |
| 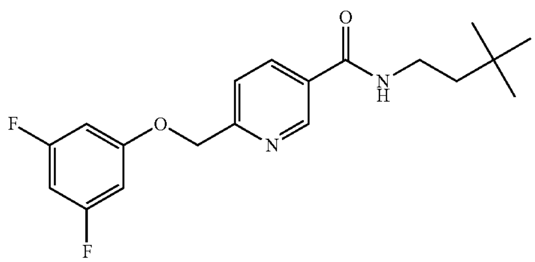 [SMILES: CC(C)(C)CCNC(=O)c1ccc(COc2cc(F)cc(F)c2)nc1] | 1.58E-06 |
| 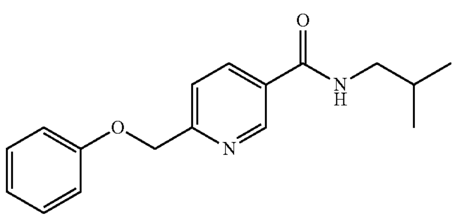 [SMILES: CC(C)CNC(=O)c1ccc(COc2ccccc2)nc1] | 1.70E-06 |
| 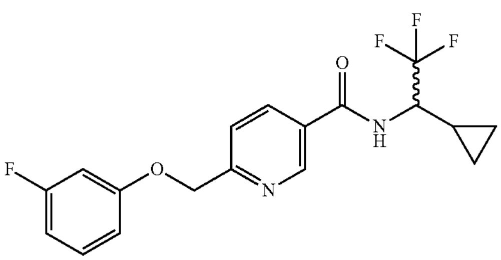 [SMILES: O=C(NC(C1CC1)C(F)(F)F)c1ccc(COc2cccc(F)c2)nc1] | 1.90E-06 |
| 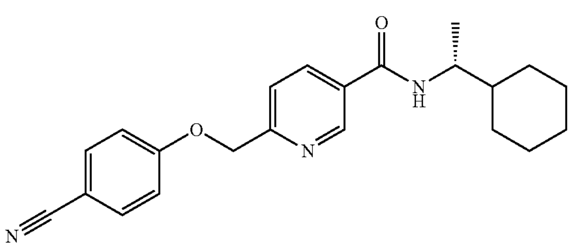 [SMILES: C[C@@H](NC(=O)c1ccc(COc2ccc(C#N)cc2)nc1)C1CCCCC1] | 2.50E-06 |
| 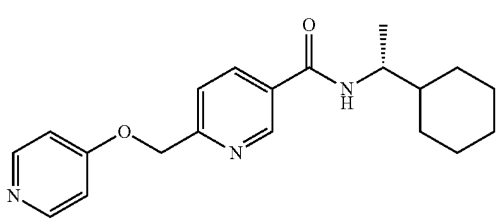 [SMILES: C[C@@H](NC(=O)c1ccc(COc2ccncc2)nc1)C1CCCCC1] | 2.60E-06 |

TABLE 1-continued

| Structure | rmGlu5 PAM EC50 |
|---|---|
| 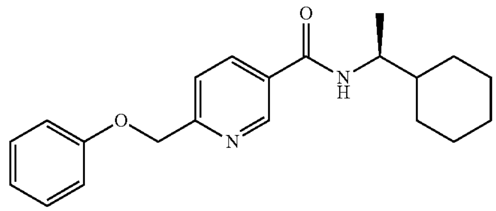 [SMILES: C[C@H](NC(=O)c1ccc(COc2ccccc2)nc1)C1CCCCC1] | 2.88E-06 |
| 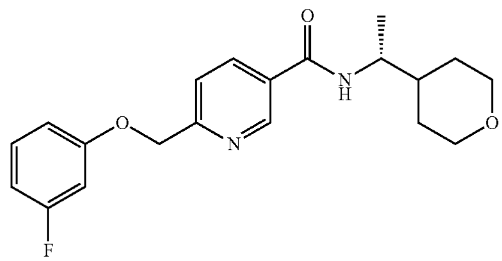 [SMILES: C[C@@H](NC(=O)c1ccc(COc2cccc(F)c2)nc1)C1CCOCC1] | 3.24E-06 |
| 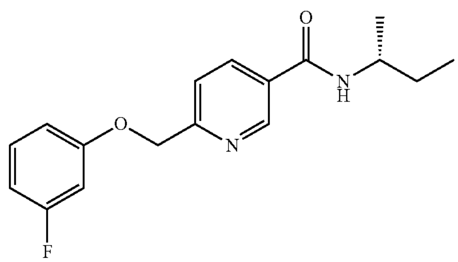 [SMILES: CC[C@@H](C)NC(=O)c1ccc(COc2cccc(F)c2)nc1] | 3.31E-06 |
| 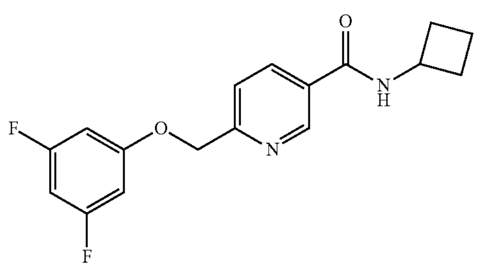 [SMILES: O=C(NC1CCC1)c1ccc(COc2cc(F)cc(F)c2)nc1] | 3.39E-06 |
| 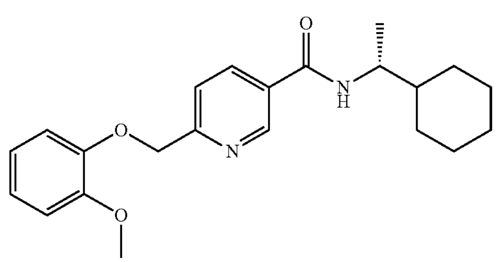 [SMILES: COc1ccccc1OCc1ccc(C(=O)N[C@H](C)C2CCCCC2)cn1] | 3.40E-06 |
| 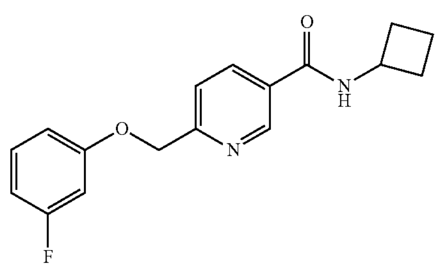 [SMILES: O=C(NC1CCC1)c1ccc(COc2cccc(F)c2)nc1] | 3.47E-06 |

TABLE 1-continued

| Structure | rmGlu5 PAM EC50 |
|---|---|
| 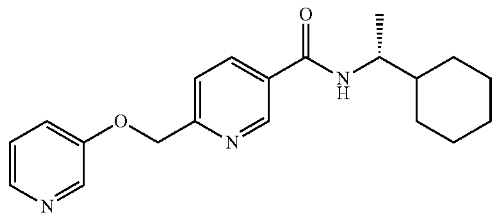 [SMILES: C[C@@H](NC(=O)c1ccc(COc2cccnc2)nc1)C1CCCCC1] | 4.50E-06 |
| 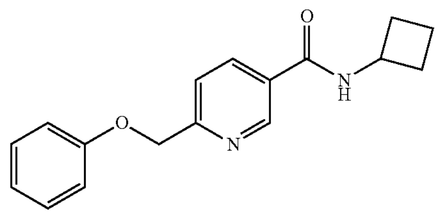 [SMILES: O=C(NC1CCC1)c1ccc(COc2ccccc2)nc1] | 4.68E-06 |
| 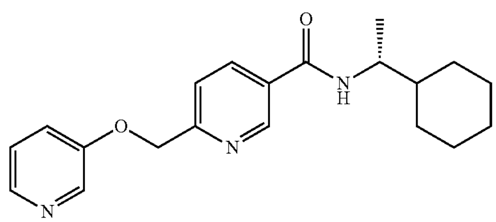 [SMILES: C[C@@H](NC(=O)c1ccc(COc2cccnc2)nc1)C1CCCCC1] | 4.90E-06 |
| 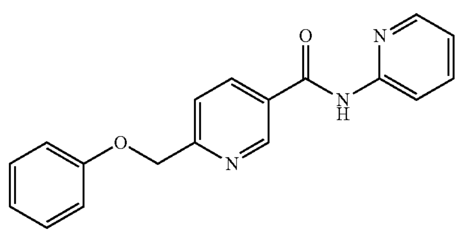 [SMILES: O=C(Nc1ccccn1)c1ccc(COc2ccccc2)nc1] | 5.25E-06 |
| | 1.00E-05 |
| | 1.00E-05 |

TABLE 1-continued

| Structure | rmGlu5 PAM EC50 |
|---|---|
| | >1.0E-05 |
| | >1.0E-05 |
| | >1.0E-05 |
| | >1.0E-05 |
| | >1.0E-05 |
| | >1.0E-05 |

TABLE 1-continued

| Structure | rmGlu5 PAM EC50 |
|---|---|
| (6-(phenoxymethyl)-N-(4-fluorophenyl)nicotinamide) | >1.0E-05 |
| (6-(phenoxymethyl)-N-(3,5-difluorophenyl)nicotinamide) | >1.0E-05 |
| (6-(phenoxymethyl)-N-(2,3-difluorophenyl)nicotinamide) | >1.0E-05 |
| (6-(phenoxymethyl)-N-(4-chloro-2-fluorophenyl)nicotinamide) | >1.0E-05 |
| (6-(phenoxymethyl)-N-(3-chlorophenyl)nicotinamide) | >1.0E-05 |
| (6-(phenoxymethyl)-N-(4-chlorophenyl)nicotinamide) | >1.0E-05 |

TABLE 1-continued

| Structure | rmGlu5 PAM EC50 |
|---|---|
| (6-phenoxymethyl-pyridin-3-yl)-N-(3-trifluoromethylphenyl)carboxamide | >1.0E-05 |
| (6-phenoxymethyl-pyridin-3-yl)-N-(3-fluoropyridin-2-yl)carboxamide | >1.0E-05 |
| (6-phenoxymethyl-pyridin-3-yl)-N-(1,3,4-thiadiazol-2-yl)carboxamide | >1.0E-05 |
| (6-phenoxymethyl-pyridin-3-yl)-N-[2-(4-chlorophenyl)ethyl]carboxamide | >1.0E-05 |
| (6-phenoxymethyl-pyridin-3-yl)-N-[3-(dimethylamino)propyl]carboxamide | >1.0E-05 |
| (6-phenoxymethyl-pyridin-3-yl)-N-(3-methoxypropyl)carboxamide | >1.0E-05 |

TABLE 1-continued
| Structure | rmGlu5 PAM EC50 |
|---|---|
| 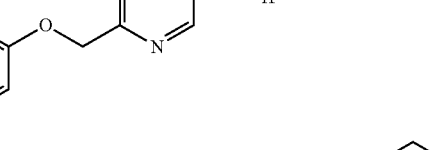 | >1.0E-05 |
| 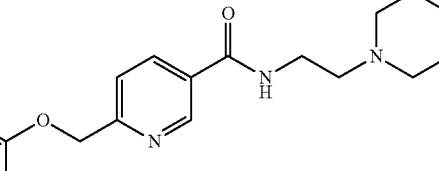 | >1.0E-05 |
| 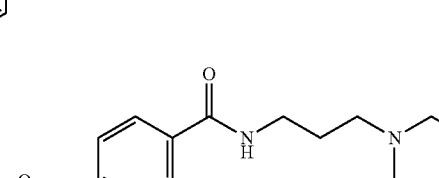 | >1.0E-05 |
| 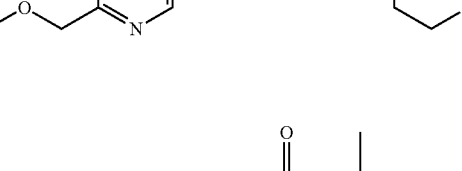 | >1.0E-05 |
| 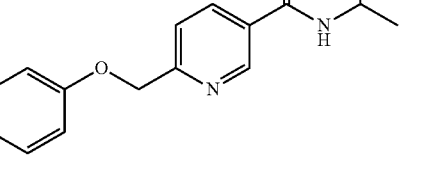 | >1.0E-05 |
| 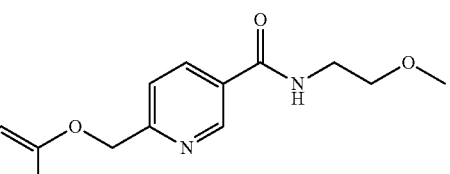 | >1.0E-05 |
| 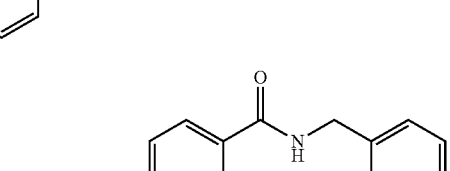 | >1.0E-05 |

TABLE 1-continued

| Structure | rmGlu5 PAM EC50 |
|---|---|
| | >1.0E-05 |
| | >1.0E-05 |
| | >1.0E-05 |
| | >1.0E-05 |
| | >1.0E-05 |

TABLE 1-continued

| Structure | rmGlu5 PAM EC50 |
|---|---|
| 5-fluoro-3-cyanophenyl-O-CH2-pyridine-C(O)NH-(R)-CH(CH3)-cyclohexyl | >1.0E-05 |
| 3-cyano-5-fluorophenyl-O-CH2-pyridine-C(O)NH-cyclobutyl | >1.0E-05 |
| 3,5-difluorophenyl-O-CH2-pyridine-C(O)NH-thiazol-2-yl | >1.0E-05 |
| 3,5-difluorophenyl-O-CH2-pyridine-C(O)NH-(1-phenylcyclobutyl) | >1.0E-05 |
| 3,5-difluorophenyl-O-CH2-pyridine-C(O)NH-iPr | >1.0E-05 |

TABLE 1-continued

| Structure | rmGlu5 PAM EC50 |
|---|---|
| | >1.0E-05 |
| | >1.0E-05 |
| | >1.0E-05 |
| | >1.0E-05 |
| | >1.0E-05 |
| | >1.0E-05 |

TABLE 1-continued

| Structure | rmGlu5 PAM EC50 |
|---|---|
| (6-(phenoxymethyl)-N-(cyclopropylmethyl)nicotinamide) | >1.0E-05 |
| (6-((3-fluorophenoxy)methyl)-N-((S)-2,2,2-trifluoro-1-cyclopropylethyl)nicotinamide) | >1.0E-05 |
| (6-(phenoxymethyl)-N-(1,3,4-thiadiazol-2-yl)nicotinamide) | >1.0E-05 |
| (6-((2-chlorophenoxy)methyl)-N-((S)-1-cyclohexylethyl)nicotinamide) | >1.0E-05 |
| (6-((2-cyanophenoxy)methyl)-N-((S)-1-cyclohexylethyl)nicotinamide) | >1.0E-05 |
| (6-((pyridin-2-yloxy)methyl)-N-((S)-1-cyclohexylethyl)nicotinamide) | >1.0E-05 |

TABLE 2

| Structure | hmGluR5 EC50 (H10H cell line) |
|---|---|
| (pyridine-carboxamide with norbornyl, 3-fluorophenoxymethyl) | NEW 1.70E-07 |
| (pyridine-carboxamide with tetrahydropyranyl-ethyl, 3-fluorophenoxymethyl) | 4.40E-07 |
| (pyridine-carboxamide with norbornyl, 3-fluorophenoxymethyl) | NEW 5.50E-07 |
| (pyridine-carboxamide with norbornyl, 3-fluorophenoxymethyl) | NEW 7.30E-07 |
| (pyridine-carboxamide with cyclohexyl-ethyl, chloropyridinyloxymethyl) | 1.50E-06 |
| (pyridine-carboxamide with tetrahydropyranyl-ethyl, 3-fluorophenoxymethyl) | 1.90E-06 |

TABLE 2-continued

| Structure | hmGluR5 EC50 (H10H cell line) |
|---|---|
| (pyridine-carboxamide with tert-butyl-ethyl, chloropyridinyloxymethyl) | 2.30E-06 |
| (pyridine-carboxamide with cyclohexyl-ethyl, fluoropyridinyloxymethyl) | 2.70E-06 |
| (pyridine-carboxamide with trifluoro-propyl, 3-fluorophenoxymethyl) | 3.20E-06 |
| (pyridine-carboxamide with thiazolyl-ethyl, 3-fluorophenoxymethyl) | >10E-06 |
| (pyridine-carboxamide with norbornyl, 3-fluorophenoxymethyl) | NEW >10E-06 |
| (pyridine-carboxamide with hydroxy-methyl-cyclobutyl, 3-fluorophenoxymethyl) | NEW >10E-06 |
| (pyridine-carboxamide with trifluoromethyl-hydroxy-cyclobutyl, 3-fluorophenoxymethyl) | NEW >10E-06 |

TABLE 2-continued

| Structure | hmGluR5 EC50 (H10H cell line) |
|---|---|
| (3-fluorophenoxymethyl-pyridine carboxamide with 1-hydroxy-1-trifluoromethyl cyclobutyl) | NEW >10E-06 |
| (3-fluorophenoxymethyl-pyridine carboxamide with 2,2,2-trifluoro-1-(pyridin-2-yl)ethyl) | >10E-06 |
| (3-fluorophenoxymethyl-pyridine carboxamide with 2,2,2-trifluoro-1-(4-fluorophenyl)ethyl) | >10E-06 |
| (3-fluorophenoxymethyl-pyridine carboxamide with 1-(pyridin-2-yl)cyclopropyl) | >10E-06 |
| (3-fluorophenoxymethyl-pyridine carboxamide with 2-(3-methyloxetan-3-yl)ethyl) | >10E-06 |
| (5-chloropyridin-3-yloxymethyl-pyridine carboxamide with (S)-1-cyclohexylethyl) | >10E-06 |
| (5-trifluoromethylpyridin-3-yloxymethyl-pyridine carboxamide with (S)-1-cyclohexylethyl) | >10E-06 |
| (2-methylpyridin-4-yloxymethyl-pyridine carboxamide with (S)-1-cyclohexylethyl) | >10E-06 |
| (5-chloropyridin-3-yloxymethyl-pyridine carboxamide with (S)-3,3-dimethylbutan-2-yl) | >10E-06 |
| (5-fluoropyridin-3-yloxymethyl-pyridine carboxamide with (S)-3,3-dimethylbutan-2-yl) | >10E-06 |
| (5-trifluoromethylpyridin-3-yloxymethyl-pyridine carboxamide with (S)-3,3-dimethylbutan-2-yl) | >10E-06 |
| (2-methylpyridin-4-yloxymethyl-pyridine carboxamide with (S)-3,3-dimethylbutan-2-yl) | >10E-06 |

TABLE 2-continued

| Structure | hmGluR5 EC50 (H10H cell line) |
|---|---|
| 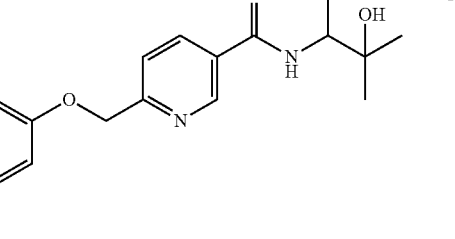 | >10E-06 |
| 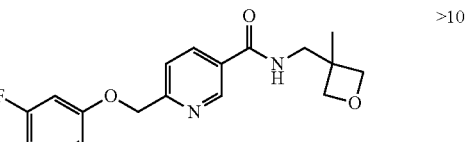 | >10E-06 |
| 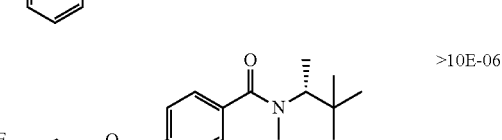 | >10E-06 |
| 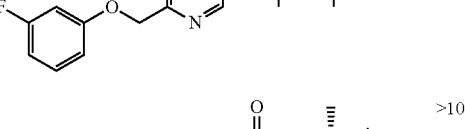 | >10E-06 |
| 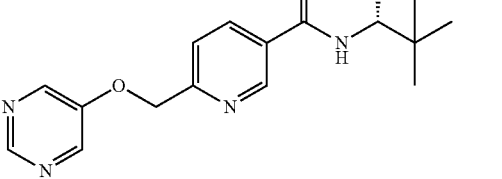 | >10E-06 |

4. Stereoisomer-Dependent Differential mGluR5 Activity

In particular embodiments where a stereogenic center is present alpha to the amide N, potentiation of mGluR5 can be highly selective for a specific enantiomer. For the compounds described herein, the stereochemical preference can be for the enantiomer having the below-indicated stereochemistry:

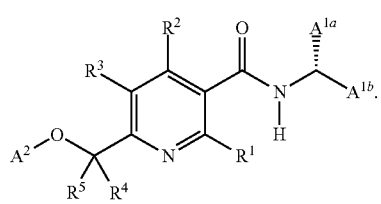

which chiral carbon may be assigned (R) or (S) configuration under the Cahn-Inglod-Prelog system.

In one aspect, one enantiomer of a disclosed compound modulates mGluR5 activity more potently than the opposite enantiomer. For example, a particular enantiomer of a disclosed compound can have an $EC_{50}$ of less than about 10 μM, of less than about 5 μM, of less than about 1 μM, of less than about 500 nM, of less than about 100 nM, or of less than about 50 nM, while the opposite enantiomer of the disclosed compound has an $EC_{50}$ of >10 μm.

In a further aspect, the enantiomer of a disclosed compound having the below-indicated stereochemistry:

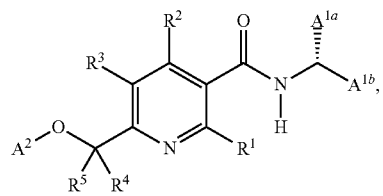

which usually represents the R-enantiomer under Cahn-Inglod-Prelog rules, modulates mGluR5 activity more potently than the opposite enantiomer, which has the below-indicated stereochemistry:

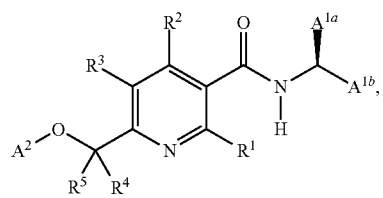

which usually represents the S-enantiomer. For example, that enantiomer (e.g., R-enantiomer) of a disclosed compound can have an $EC_{50}$ of less than about 10 μM, of less than about 5 μM, of less than about 1 μM, of less than about 500 nM, of less than about 100 nM, or of less than about 50 nM, while the opposite enantiomer (e.g., S-enantiomer) of the disclosed compound has an $EC_{50}$ of >10 μM.

In a further aspect, one enantiomer of a disclosed compound modulates mGluR5 activity more potently than the opposite enantiomer. For example, a particular enantiomer of a disclosed compound can have an $EC_{50}$ of less than about 10%, of less than about 20%, of less than about 30%, of less than about 40%, of less than about 50%, or of less than about 75% of the $EC_{50}$ of the opposite enantiomer.

In a further aspect, the enantiomer of a disclosed compound having the below-indicated stereochemistry:

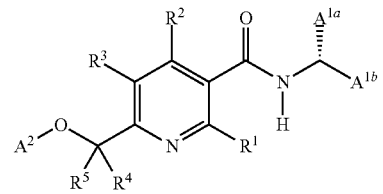

which usually represents the R-enantiomer under Cahn-Inglod-Prelog rules, modulates mGluR5 activity more potently than the opposite enantiomer, which has the below-indicated stereochemistry:

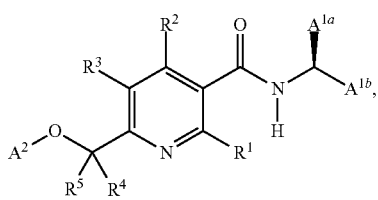

which usually represents the S-enantiomer. For example, that enantiomer (e.g., R-enantiomer) of a disclosed compound can have an $EC_{50}$ of less than about 10%, of less than about 20%, of less than about 30%, of less than about 40%, of less than about 50%, or of less than about 75% of the $EC_{50}$ of the opposite enantiomer (e.g., S-enantiomer).

As illustrated below (Table 3a and Table 3b), Example 11a, (R)-N-(1-cyclohexylethyl)-6-((3-fluorophenoxy)methyl) nicotinamide, displays excellent potency as an mGluR5 potentiator with $EC_{50}$ of 130 nM. In contrast, the opposite stereochemical enantiomer with the S configuration Example 1b, (S)—N-(1-cyclohexylethyl)-6-((3-fluorophenoxy)methyl)nicotinamide prepared in a similar manner starting from commercially available reagents displays an $EC_{50}$>10 µM.

Similarly, enantioselective mGluR5 potentiation can be found for the difluoro-substituted stereoisomers, Example 12a and 12b as well as the butane substituted amide stereoisomers, Example 13a and 13b. In the examples shown the enantioselective mGluR5 potentiation is >100-fold in each case.

TABLE 3A

| Example | (R) enantiomer | mGluR5 $EC_{50}$ (nM) |
|---|---|---|
| 11a | (R)-N-(1-cyclohexylethyl)-6-((3-fluorophenoxy)methyl)nicotinamide | 130 |
| 12a | (R)-N-(1-cyclohexylethyl)-6-((3,5-difluorophenoxy)methyl)nicotinamide | 309 |
| 13a | (R)-N-(3,3-dimethylbutan-2-yl)-6-((3-fluorophenoxy)methyl)nicotinamide | 81 |

TABLE 3B

| Example | (S) enantiomer | mGluR5 EC$_{50}$ (nM) |
|---|---|---|
| 11b | 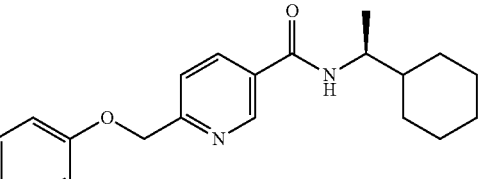 (S)-N-(1-cyclohexylethyl)-6-((3-fluorophenoxy)methyl)nicotinamide | >10,000 |
| 12b | 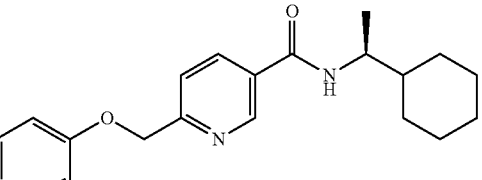 (S)-N-(1-cyclohexylethyl)-6-((3,5-difluorophenoxy)methyl)nicotinamide | >10,000 |
| 13b | 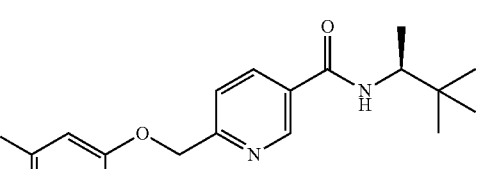 (S)-N-(3,3-dimethylbutan-2-yl)-6-((3-fluorophenoxy)methyl)nicotinamide | >10,000 |

While the disclosed compounds can be provided as a mixture of both the R-enantiomer and the S-enantiomer, it can be desired to provide the mixture of enantiomers of a disclosed compound enriched in the more potent compound. Such can be desired in order to, for example, increase the concentration of an active (or more active) enantiomer or in order to decrease the concentration of a less active (or inactive) enantiomer. Such can improve potency of a pharmaceutical preparation. Such also can minimize undesired side-effects present in a less active enantiomer and not present (or less present) in a more active enantiomer.

Thus, in various aspects, a disclosed compound can be provided in a form enriched in R-enantiomer of the compound. For example, a disclosed compound can be provided in an enantiomeric excess of greater than 50%, greater than 60%, greater than 70%, greater than 75%, greater than 80%, greater than 85%, greater than 90%, greater than 95%, greater than 98%, or greater than 99% of the R-enantiomer of the compound. In one aspect, the R-enantiomer is substantially free from the S-enantiomer. For example, the "R" forms of the compounds can be provided substantially free from the "S" forms of the compounds.

D. Metabotropic Glutamate Receptor Activity

The utility of the compounds in accordance with the present invention as potentiators of metabotropic glutamate receptor activity, in particular mGluR5 activity, can be demonstrated by methodology known in the art. Human embryonic kidney (HEK) cells transfected with rat mGluR5 were plated in clear bottom assay plates for assay in a Functional Drug Screening System (FDSS). In the alternative assay, HEK cells transfected with human mGluR5 (H10H cell line) were plated for assay in the FDSS. Rat assay results were found to correlate well with human assay results. The cells were loaded with a $Ca^{2+}$-sensitive fluorescent dye (e.g., Fluo-4), and the plates were washed and placed in the FDSS instrument. After establishment of a fluorescence baseline for twelve seconds, the compounds of the present invention were added to the cells, and the response in cells was measured. Five minutes later, an mGluR5 agonist (e.g., glutamate, 3,5-dihydroxyphenylglycine, or quisqualate) was added to the cells, and the response of the cells was measured. Potentiation of the agonist response of mGluR5 by the compounds in the present invention was observed as an increase in response to non-maximal concentrations of agonist (here, glutamate) in the presence of compound compared to the response to agonist in the absence of compound.

The above described assay operated in two modes. In the first mode, a range of concentrations of the present compounds were added to cells, followed by a single fixed concentration of agonist. If a compound acted as a potentiator, an EC$_{50}$ value for potentiation and a maximum extent of potentiation by the compound at this concentration of agonist was determined by non-linear curve fitting. In the second mode, several fixed concentrations of the present compounds were added to various wells on a plate, followed by a range of concentrations of agonist for each concentration of present compound; the $EC_{50}$ values for the agonist at each concentration of compound were determined by non-linear curve fitting. A decrease in the $EC_{50}$ value of the agonist with increasing concentrations of the present compounds (a leftward shift of the agonist concentration-response curve) is an indication of the degree of mGluR5 potentiation at a given concentration of the present compound. An increase in the $EC_{50}$ value of the agonist with increasing concentrations of the present compounds (a rightward shift of the agonist concentration-response curve) is an indication of the degree of mGluR5 antagonism at a given concentration of the present compound. The second mode also indicates whether the present compounds also affect the maximum response to mGluR5 to agonists.

In particular, the disclosed compounds had activity in potentiating the mGluR5 receptor in the aforementioned assays, generally with an $EC_{50}$ for potentiation of less than about 10 μM. Preferred compounds within the present invention had activity in potentiating the mGluR5 receptor with an $EC_{50}$ for potentiation of less than about 500 nM. Preferred compounds further caused a leftward shift of the agonist $EC_{50}$ by greater than 3-fold. These compounds did not cause mGluR5 to respond in the absence of agonist, and they did not elicit a significant increase in the maximal response of mGluR5 to agonists. These compounds are positive allosteric modulators (potentiators) of human and rat mGluR5 and were selective for mGluR5 compared to the other seven subtypes of metabotropic glutamate receptors.

In vivo efficacy for disclosed compounds can be measured in a number of preclinical rat behavioral model where known, clinically useful antipsychotics display similar positive responses. For example, disclosed compounds can reverse amphetamine-induced hyperlocomotion in male Sprague-Dawley rats at doses ranging from 1 to 100 mg/kg i.p.

E. Methods of Making the Compounds

In one aspect, the invention relates to methods of making compounds useful as positive allosteric modulators (potentiators) of the metabotropic glutamate receptor subtype 5 (mGluR5), which can be useful in the treatment neurological and psychiatric disorders associated with glutamate dysfunction and other diseases in which metabotropic glutamate receptors are involved. The compounds of this invention can be prepared by employing reactions as shown in the following schemes, in addition to other standard manipulations that are known in the literature, exemplified in the experimental sections or clear to one skilled in the art. Substituent numbering as shown in schemes does not necessarily correlate to that used in the claims and often, for clarity, a single substituent is shown to attach to the compound where multiple substituents are allowed under the definitions disclosed herein. Reactions used to generate the compounds of this invention are prepared by employing reactions as shown in the following Reaction Schemes, in addition to other standard manipulations known in the literature or to one skilled in the art. The following examples are provided so that the invention might be more fully understood, are illustrative only, and should not be construed as limiting.

In one aspect, the invention relates to a method of making a substituted 6-methylnicotinamide comprising the steps of substituting a leaving group with $A^2OH$, wherein $A^2$ is an optionally substituted organic residue selected from aryl and heteroaryl having 4-10 carbons; and forming an amide with $A^1NH_2$, wherein $A^1$ is an organic residue having 2-10 carbons and selected from optionally substituted alkyl, optionally substituted cycloalkyl, optionally substituted heterocycloalkyl, optionally substituted cycloalkenyl, optionally substituted heterocycloalkenyl; optionally substituted aryl, and heteroaryl optionally substituted with one or more of halogen, methyl, trifluoromethyl, ethyl, propyl, or butyl.

In a further aspect, the substituting step is performed before the forming an amide step. In a further aspect, the substituting step is displacement of a halogen. In a further aspect, the method further comprises a halogenation step prior to the substituting step. In a further aspect, the substituting step is a Mitsunobu reaction. In a further aspect, the method further comprises a hydroxylation step prior to the substituting step. In a further aspect, the forming an amide step is performed before the substituting step.

In a further aspect, the substituted 6-methylnicotinamide formed has a structure represented by a formula:

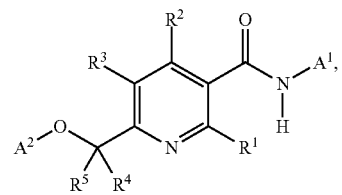

wherein $A^1$ is an organic residue having 2-10 carbons and selected from optionally substituted alkyl, optionally substituted cycloalkyl, optionally substituted heterocycloalkyl, optionally substituted cycloalkenyl, optionally substituted heterocycloalkenyl; optionally substituted aryl, and heteroaryl optionally substituted with one or more of halogen, methyl, trifluoromethyl, ethyl, propyl, or butyl; wherein $A^2$ is an optionally substituted organic residue selected from aryl and heteroaryl having 4-10 carbons; wherein $R^1$ and $R^2$ are independently selected from hydrogen, halogen, C1 to C6 alkyl, aryl, heteroaryl, cycloalkyl, heterocycloalkyl, cycloalkenyl, heterocycloalkenyl, OH, CN, $CO_2H$, $CF_3$, $OCF_3$, $OCH_3$, and $—CHRNH_2(OH)$, wherein $R^3$ is selected from hydrogen, hydroxyl, halogen, C1 to C6 alkyl, OH, CN, $CO_2H$, $CF_3$, $OCF_3$, $OCH_3$, and $—CHRNH_2(OH)$, wherein is R is $CF_3$; wherein $R^4$ and $R^5$ are independently selected from hydrogen, C1 to C6 alkyl, aryl, heteroaryl, cycloalkyl, heterocycloalkyl, cycloalkenyl, and heterocycloalkenyl, or wherein $R^4$ and $R^5$, together with the intermediate carbon, form a cyclic or heterocyclic ring having from 3 to 6 carbons; or a pharmaceutically acceptable salt or N-oxide thereof.

In a further aspect, the substituted 6-methylnicotinamide formed has a structure represented by a formula:

1. Reaction Scheme I

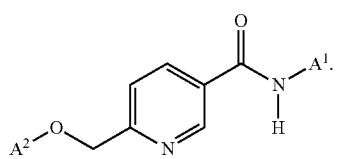

Examples of ethers of type 1.3 can be prepared as outlined in Scheme 1. Starting from 6-methyl nicotinates bromination followed by displacement with an appropriate alcohol nucleophile gives ester 1.2; subsequent saponification and amide coupling gives Examples 1.3.

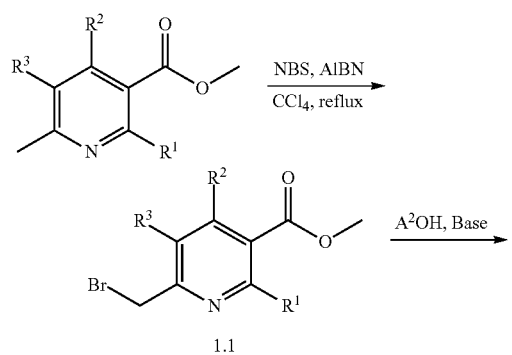

Scheme 1.

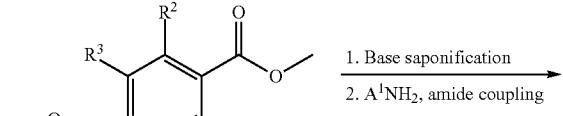

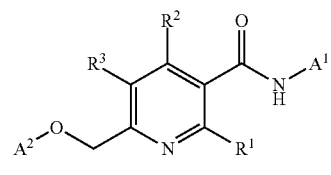

2. Reaction Scheme II

Alternatively, one can generate the N-oxide intermediate and through a Polonovski rearrangement access the primary alcohol 2.2. Intermediate 2.2 can either be subjected with various acidic alcohols under Mitsunobu conditions to generate the penultimate ethers which upon saponification and coupling gives final compounds 1.3 or 2.2, which can be brominated under Lee conditions and then converted to final examples in a manner similar to that described for Scheme 1.

In addition, as outlined in Scheme 3, one can generate an amide coupled intermediate such as 3.1 and then upon further oxidative manipulation generate intermediate 3.2 and 3.3 as penultimate precursors to generate final examples 1.3.

Scheme 2.

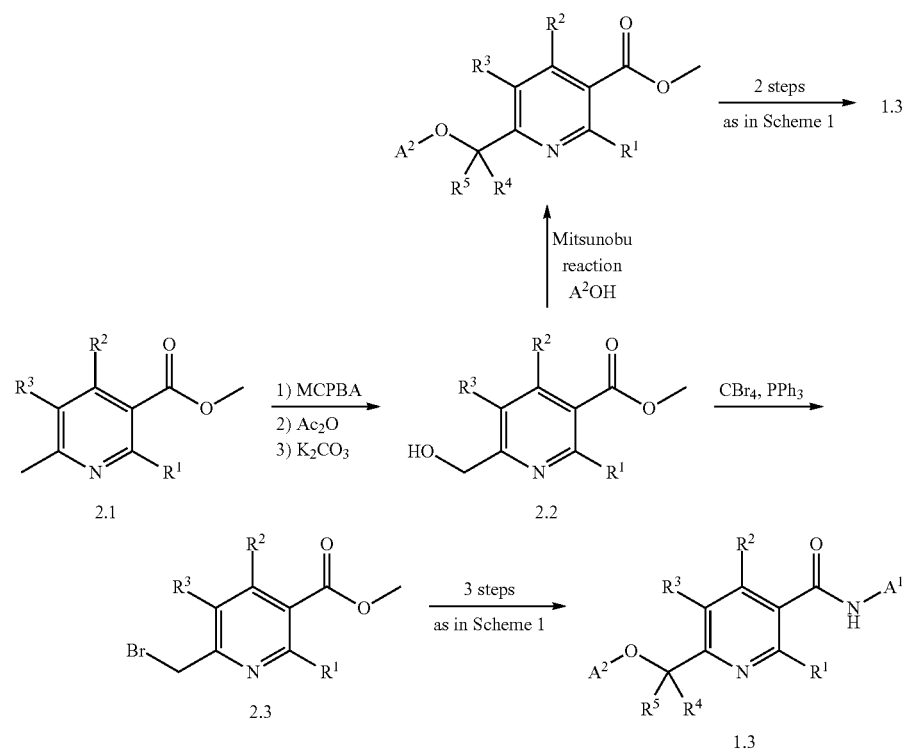

3. Reaction Scheme III

In a further aspect, disclosed compounds can be prepared as shown below.

Scheme 3.

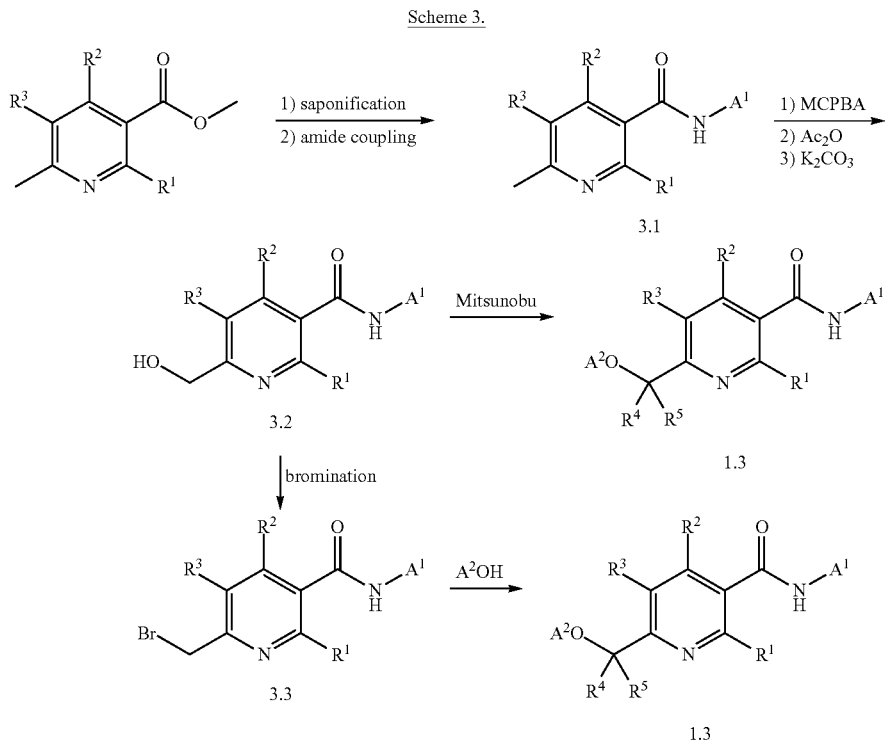

Compounds are represented in generic form, with substituents as noted in compound descriptions elsewhere herein.

In a further aspect, the method provides a disclosed compound, for example, a compound listed in Table 1 or Table 2. Compounds in Tables 1 and 2 were synthesized as disclosed herein. The requisite starting materials were commercially available, described in the literature or readily synthesized by one skilled in the art of organic synthesis.

Thus, it is understood that a disclosed methods can be used to provide the disclosed compounds.

F. Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

A potentiated amount of an mGluR agonist to be administered in combination with an effective amount of a compound of formula I is expected to vary from about 0.1 milligram per kilogram of body weight per day (mg/kg/day) to about 100 mg/kg/day and is expected to be less than the amount that is required to provide the same effect when administered without an effective amount of a compound of formula I. Preferred amounts of a co-administered mGluR agonist are able to be determined by one skilled in the art.

In the treatment conditions which require potentiation of metabotropic glutamate receptor activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The disclosed pharmaceutical compositions can further comprise other therapeutically active compounds, which are usually applied in the treatment of the above mentioned pathological conditions.

It is understood that the disclosed compositions can be employed in the disclosed methods of using.

G. Methods of Using the Compounds and Compositions

The amino acid L-glutamate (referred to herein simply as glutamate) is the principal excitatory neurotransmitter in the mammalian central nervous system (CNS). Within the CNS, glutamate plays a key role in synaptic plasticity (e.g., long term potentiation (the basis of learning and memory)), motor control and sensory perception. It is now well understood that a variety of neurological and psychiatric disorders, including, but not limited to, schizophrenia general psychosis and cognitive deficits, are associated with dysfunctions in the glutamatergic system. Thus, modulation of the glutamatergic system is an important therapeutic goal. Glutamate acts through two distinct receptors: ionotropic and metabotropic glutamate receptors. The first class, the ionotropic glutamate receptors, is comprised of multi-subunit ligand-gated ion channels that mediate excitatory post-synaptic currents. Three subtypes of ionotropic glutamate receptors have been identified, and despite glutamate serving as agonist for all three receptor subtypes, selective ligands have been discovered that activate each subtype. The ionotropic glutamate receptors are named after their respective selective ligands: kainite receptors, AMPA receptors and NMDA receptors.

The second class of glutamate receptor, termed metabotropic glutamate receptors, (mGluRs), are G-protein coupled receptors (GPCRs) that modulate neurotransmitter release or the strength of synaptic transmission, based on their location (pre- or post-synaptic). The mGluRs are family C GPCR, characterized by a large (~560 amino acid) "venus fly trap" agonist binding domain in the amino-terminal domain of the receptor. This unique agonist binding domain distinguishes family C GPCRs from family A and B GPCRs wherein the agonist binding domains are located within the 7-strand transmembrane spanning (7TM) region or within the extracellular loops that connect the strands to this region. To date, eight distinct mGluRs have been identified, cloned and sequenced. Based on structural similarity, primary coupling to intracellular signaling pathways and pharmacology, the mGluRs have been assigned to three groups: Group I (mGluR1 and mGluR5), Group II (mGluR2 and mGluR3) and Group III (mGluR4, mGluR6, mGluR7 and mGluR8). Group I mGluRs are coupled through $G\alpha q/11$ to increase inositol phosphate and metabolism and resultant increases in intracellular calcium. Group I mGluRs are primarily located post-synaptically and have a modualtory effect on ion channel activity and neuronal excitability. Group II (mGluR2 and mGluR3) and Group III (mGluR4, mGluR6, mGluR7 and mGluR8) mGluRs are primarily located pre-synaptically where they regulate the release of neurotransmitters, such as glutamate. Group II and Group III mGluRs are coupled to $G\alpha i$ and its associated effectors such as adenylate cyclase.

Post-synaptic mGluRs are known to functionally interact with post-synaptic ionotropic glutamate receptors, such as the NMDA receptor. For example, activation of mGluR5 by a selective agonist has been shown to increase post-synaptic NMDA currents (Mannaioni et. al. J. Neurosci. 21:5925-5934 (2001)). Therefore, modulation of mGluRs is an approach to modulating glutamatergic transmission. Numerous reports indicate that mGluR5 plays a role in a number of disease states including anxiety (Spooren et. al. J. Pharmacol. Exp. Therapeut. 295:1267-1275 (2000), Tatarczynska et al. Br. J. Pharmaol. 132:1423-1430 (2001)), schizophrenia (reviewed in Chavez-Noriega et al. Curr. Drug Targets: CNS & Neurological Disorders 1:261-281 (2002), Kinney, G. G. et al. J. Pharmacol. Exp. Therapeut. 313:199-206 (2005)), addiction to cocaine (Chiamulera et al. Nature Neurosci. 4:873-874 (2001), Parkinson's disease (Awad et al. J. Neurosci. 20:7871-7879 (2000), Ossowska et al. Neuropharmacol. 41: 413-420 (2001), and pain (Salt and Binns Neurosci. 100: 375-380 (2001).

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

In one aspect, the subject compounds can be coadministered with ant-Alzheimer's agents, beta-secretase inhibitors, gamma-secretase inhibitors, muscarinic agonists, muscarinic potentiators HMG-CoA reductase inhibitors, NSAIDs and anti-amyloid antibodies.

In another aspect, the subject compounds can be administered in combination with sedatives, hypnotics, anxiolytics, antipsychotics, selective serotonin reuptake inhibitors (SSRIs), monoamine oxidase inhibitors (MAOIs), 5-HT2 antagonists, GlyT1 inhibitors and the like such as, but not limited to: risperidone, clozapine, haloperidol, fluoxetine, prazepam, xanomeline, lithium, phenobarbitol, and salts thereof and combinations thereof.

In another aspect, the subject compound can be used in combination with levodopa (with or without a selective extracerebral decarboxylase inhibitor), anitcholinergics such as biperiden, COMT inhibitors such as entacapone, A2a adenosine antagonists, cholinergic agonists, NMDA receptor antagonists and dopamine agonists.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of neurological and psychiatric disorders associated with glutamate dysfunction.

Examples of disorders associated with glutamate dysfunction include: acute and chronic neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, addictive behavior, including addiction to substances (including opiates, nicotine, tobacco products, alcohol, benzodiazepines, cocaine, sedatives, hypnotics, etc.), withdrawal from such addictive substances (including substances such as opiates, nicotine, tobacco products, alcohol, benzodiazepines, cocaine, sedatives, hypnotics, etc.), obesity, psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), attention deficit/hyperactivity disorder, and conduct disorder.

Anxiety disorders that can be treated or prevented by the compositions disclosed herein include generalized anxiety disorder, panic disorder, and obsessive compulsive disorder. Addictive behaviors include addiction to substances (including opiates, nicotine, tobacco products, alcohol, benzodiazepines, cocaine, sedatives, hypnotics, etc.), withdrawal from such addictive substances (including substances such as opiates, nicotine, tobacco products, alcohol, benzodiazepines, cocaine, sedatives, hypnotics, etc.) and substance tolerance.

Thus, in some aspects of the disclosed method, the disorder is dementia, delirium, amnestic disorders, age-related cognitive decline, schizophrenia, psychosis including schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, psychotic depression.

Thus, provided is a method for treating or prevention schizophrenia, comprising: administering to a subject at least one disclosed compound; at least one disclosed pharmaceutical composition; and/or at least one disclosed product in a dosage and amount effective to treat the disorder in the subject. At present, the fourth edition of the Diagnostic and Statistical Manual of Mental Disorders (DSM-IV) (1994, American Psychiatric Association, Washington, D.C.), provides a diagnostic tool including schizophrenia and related disorders.

Also provided is a method for treating or prevention anxiety, comprising: administering to a subject at least one disclosed compound; at least one disclosed pharmaceutical composition; and/or at least one disclosed product in a dosage and amount effective to treat the disorder in the subject. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified.

a. Treatment of a Neurological and/or Psychiatric Disorder Associated with Glutamate Dysfunction In one aspect, the invention relates to a method for the treatment of a neurological and/or psychiatric disorder associated with glutamate dysfunction in a mammal comprising the step of administering to the mammal a therapeutically effective amount of least one compound having a structure represented by a formula:

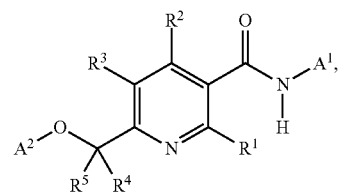

wherein $A^1$ is an organic residue having 2-10 carbons and selected from optionally substituted alkyl, optionally substituted cycloalkyl, optionally substituted heterocycloalkyl, optionally substituted cycloalkenyl, optionally substituted heterocycloalkenyl; optionally substituted aryl, and heteroaryl optionally substituted with one or more of halogen, methyl, trifluoromethyl, ethyl, propyl, or butyl; wherein $A^2$ is an optionally substituted organic residue selected from aryl and heteroaryl having 4-10 carbons; wherein $R^1$ and $R^2$ are independently selected from hydrogen, halogen, C1 to C6 alkyl, aryl, heteroaryl, cycloalkyl, heterocycloalkyl, cycloalkenyl, heterocycloalkenyl, OH, CN, CO$_2$H, CF$_3$, OCF$_3$, OCH$_3$, and —CHRNH$_2$(OH), wherein is R is CF$_3$; wherein R$^3$ is selected from hydrogen, hydroxyl, halogen, C1 to C6 alkyl, OH, CN, CO$_2$H, CF$_3$, OCF$_3$, OCH$_3$, and —CHRNH$_2$(OH), wherein is R is CF$_3$; wherein R$^4$ and R$^5$ are independently selected from hydrogen, C1 to C6 alkyl, aryl, heteroaryl, cycloalkyl, heterocycloalkyl, cycloalkenyl, and heterocycloalkenyl, or wherein R$^4$ and R$^5$, together with the intermediate carbon, form a cyclic or heterocyclic ring having from 3 to 6 carbons; or a pharmaceutically acceptable salt or N-oxide thereof.

In one aspect, the mammal is a human. In a further aspect, the mammal has been diagnosed with a need for treatment of the disorder prior to the administering step. In a further aspect, the method further comprises the step of identifying a mammal in need of treatment of the disorder.

In a further aspect, the disorder is a neurological and/or psychiatric disorder associated with mGluR5 dysfunction. In a further aspect, the disorder is selected from dementia, delirium, amnestic disorders, age-related cognitive decline, schizophrenia, psychosis including schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression.

In a further aspect, the disorder is a disease of uncontrolled cellular proliferation. In a further aspect, the disorder is cancer, for example, breast cancer, renal cancer, gastric cancer, or colorectal cancer. In a further aspect, the disorder is selected from lymphoma, cancers of the brain, genitourinary tract cancer, lymphatic system cancer, stomach cancer, larynx cancer, lung, pancreatic cancer, breast cancer, and malignant melanoma.

b. Potentiation of Metabotropic Glutamate Receptor Activity

In one aspect, the invention relates to a method for potentiation of metabotropic glutamate receptor activity in a mammal comprising the step of administering to the mammal a therapeutically effective amount of least one compound having a structure represented by a formula:

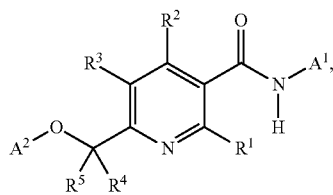

wherein A$^1$ is an organic residue having 2-10 carbons and selected from optionally substituted alkyl, optionally substituted cycloalkyl, optionally substituted heterocycloalkyl, optionally substituted cycloalkenyl, optionally substituted heterocycloalkenyl; optionally substituted aryl, and heteroaryl optionally substituted with one or more of halogen, methyl, trifluoromethyl, ethyl, propyl, or butyl; wherein A$^2$ is an optionally substituted organic residue selected from aryl and heteroaryl having 4-10 carbons; wherein R$^1$ and R$^2$ are independently selected from hydrogen, halogen, C1 to C6 alkyl, aryl, heteroaryl, cycloalkyl, heterocycloalkyl, cycloalkenyl, heterocycloalkenyl, OH, CN, CO$_2$H, CF$_3$, OCF$_3$, OCH$_3$, and —CHRNH$_2$(OH), wherein is R is CF$_3$; wherein R$^3$ is selected from hydrogen, hydroxyl, halogen, C1 to C6 alkyl, OH, CN, CO$_2$H, CF$_3$, OCF$_3$, OCH$_3$, and —CHRNH$_2$(OH), wherein is R is CF$_3$; wherein R$^4$ and R$^5$ are independently selected from hydrogen, C1 to C6 alkyl, aryl, heteroaryl, cycloalkyl, heterocycloalkyl, cycloalkenyl, and heterocycloalkenyl, or wherein R$^4$ and R$^5$, together with the intermediate carbon, form a cyclic or heterocyclic ring having from 3 to 6 carbons; or a pharmaceutically acceptable salt or N-oxide thereof.

In one aspect, the mammal is a human. In a further aspect, the mammal has been diagnosed with a need for treatment of the disorder prior to the administering step. In a further aspect, the method further comprises the step of identifying a mammal in need of treatment of the disorder. In a further aspect, the metabotropic glutamate receptor is mGluR5.

c. Partial Agonism of Metabotropic Glutamate Receptor Activity

In one aspect, the invention relates to a method for partial agonism of metabotropic glutamate receptor activity in a mammal comprising the step of administering to the mammal a therapeutically effective amount of least one compound having a structure represented by a formula:

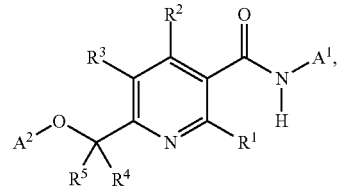

wherein A$^1$ is an organic residue having 2-10 carbons and selected from optionally substituted alkyl, optionally substituted cycloalkyl, optionally substituted heterocycloalkyl, optionally substituted cycloalkenyl, optionally substituted heterocycloalkenyl; optionally substituted aryl, and heteroaryl optionally substituted with one or more of halogen, methyl, trifluoromethyl, ethyl, propyl, or butyl; wherein A$^2$ is an optionally substituted organic residue selected from aryl and heteroaryl having 4-10 carbons; wherein R$^1$ and R$^2$ are independently selected from hydrogen, halogen, C1 to C6 alkyl, aryl, heteroaryl, cycloalkyl, heterocycloalkyl, cycloalkenyl, heterocycloalkenyl, OH, CN, CO$_2$H, CF$_3$, OCF$_3$, OCH$_3$, and —CHRNH$_2$(OH), wherein is R is CF$_3$; wherein R$^3$ is selected from hydrogen, hydroxyl, halogen, C1 to C6 alkyl, OH, CN, CO$_2$H, CF$_3$, OCF$_3$, OCH$_3$, and —CHRNH$_2$(OH), wherein is R is CF$_3$; wherein R$^4$ and R$^5$ are independently selected from hydrogen, C1 to C6 alkyl, aryl, heteroaryl, cycloalkyl, heterocycloalkyl, cycloalkenyl, and heterocycloalkenyl, or wherein R$^4$ and R$^5$, together with the intermediate carbon, form a cyclic or heterocyclic ring having from 3 to 6 carbons; or a pharmaceutically acceptable salt or N-oxide thereof.

In one aspect, the mammal is a human. In a further aspect, the mammal has been diagnosed with a need for treatment of the disorder prior to the administering step. In a further aspect, the method further comprises the step of identifying a mammal in need of treatment of the disorder. In a further aspect, the metabotropic glutamate receptor is mGluR5.

d. Enhancing Cognition

In one aspect, the invention relates to a method for enhancing cognition in a mammal comprising the step of administering to the mammal an effective amount of least one compound having a structure represented by a formula:

123

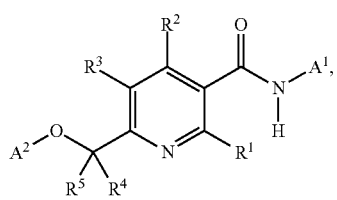

wherein $A^1$ is an organic residue having 2-10 carbons and selected from optionally substituted alkyl, optionally substituted cycloalkyl, optionally substituted heterocycloalkyl, optionally substituted cycloalkenyl, optionally substituted heterocycloalkenyl; optionally substituted aryl, and heteroaryl optionally substituted with one or more of halogen, methyl, trifluoromethyl, ethyl, propyl, or butyl; wherein $A^2$ is an optionally substituted organic residue selected from aryl and heteroaryl having 4-10 carbons; wherein $R^1$ and $R^2$ are independently selected from hydrogen, halogen, C1 to C6 alkyl, aryl, heteroaryl, cycloalkyl, heterocycloalkyl, cycloalkenyl, heterocycloalkenyl, OH, CN, $CO_2H$, $CF_3$, $OCF_3$, $OCH_3$, and —$CHRNH_2(OH)$, wherein is R is $CF_3$; wherein $R^3$ is selected from hydrogen, hydroxyl, halogen, C1 to C6 alkyl, OH, CN, $CO_2H$, $CF_3$, $OCF_3$, $OCH_3$, and —$CHRNH_2(OH)$, wherein is R is $CF_3$; wherein $R^4$ and $R^5$ are independently selected from hydrogen, C1 to C6 alkyl, aryl, heteroaryl, cycloalkyl, heterocycloalkyl, cycloalkenyl, and heterocycloalkenyl, or wherein $R^4$ and $R^5$, together with the intermediate carbon, form a cyclic or heterocyclic ring having from 3 to 6 carbons; or a pharmaceutically acceptable salt or N-oxide thereof.

In one aspect, the mammal is a human. In a further aspect, the cognition enhancement is a statistically significant increase in Novel Object Recognition. In a further aspect, the cognition enhancement is a statistically significant increase in performance of the Wisconsin Card Sorting Test.

e. Modulating mGluR5 Activity in Mammals

In one aspect, the invention relates to a method for modulating mGluR5 activity in a mammal comprising the step of administering to the mammal an effective amount of least one compound having a structure represented by a formula:

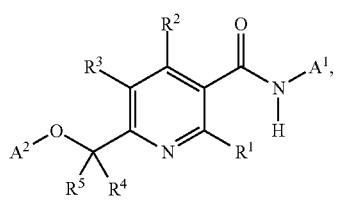

wherein $A^1$ is an organic residue having 2-10 carbons and selected from optionally substituted alkyl, optionally substituted cycloalkyl, optionally substituted heterocycloalkyl, optionally substituted cycloalkenyl, optionally substituted heterocycloalkenyl; optionally substituted aryl, and heteroaryl optionally substituted with one or more of halogen, methyl, trifluoromethyl, ethyl, propyl, or butyl; wherein $A^2$ is an optionally substituted organic residue selected from aryl and heteroaryl having 4-10 carbons; wherein $R^1$ and $R^2$ are independently selected from hydrogen, halogen, C1 to C6 alkyl, aryl, heteroaryl, cycloalkyl, heterocycloalkyl, cycloalkenyl, heterocycloalkenyl, OH, CN, $CO_2H$, $CF_3$, $OCF_3$, $OCH_3$, and —$CHRNH_2(OH)$, wherein is R is $CF_3$; wherein $R^3$ is selected from hydrogen, hydroxyl, halogen, C1 to C6 alkyl, OH, CN, $CO_2H$, $CF_3$, $OCF_3$, $OCH_3$, and —$CHRNH_2(OH)$, wherein is R is $CF_3$; wherein $R^4$ and $R^5$ are independently selected from hydrogen, C1 to C6 alkyl, aryl, heteroaryl, cycloalkyl, heterocycloalkyl, cycloalkenyl, and heterocycloalkenyl, or wherein $R^4$ and $R^5$, together with the intermediate carbon, form a cyclic or heterocyclic ring having from 3 to 6 carbons; or a pharmaceutically acceptable salt or N-oxide thereof.

In one aspect, the mammal is a human. In a further aspect, the mammal has been diagnosed with a need for modulating mGluR5 activity prior to the administering step. In a further aspect, the mammal has been diagnosed with a need for treatment of a disorder related to mGluR5 activity prior to the administering step. In a further aspect, the method further comprises the step of identifying a mammal in need of decreasing mGluR5 activity.

In one aspect, modulating is increasing. In a further aspect, modulating is potentiation. In a further aspect, modulating is partial agonism.

In one aspect, an effective amount is a therapeutically effective amount.

In one aspect, the disorder is a neurological and/or psychiatric disorder associated with mGluR5 dysfunction. In a further aspect, the disorder is selected from dementia, delirium, amnestic disorders, age-related cognitive decline, schizophrenia, psychosis including schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression.

In a further aspect, the disorder is a disease of uncontrolled cellular proliferation. In a further aspect, the disorder is cancer. In a further aspect, the disorder is selected from breast cancer, renal cancer, gastric cancer, and colorectal cancer. In a further aspect, the disorder is selected from lymphoma, cancers of the brain, genitourinary tract cancer, lymphatic system cancer, stomach cancer, larynx cancer, lung, pancreatic cancer, breast cancer, and malignant melanoma.

f. Modulating mGluR5 Activity in Cells

In one aspect, the invention relates to a method for modulating mGluR5 activity in at least one cell, comprising the step of contacting the at least one cell with an effective amount of least one compound having a structure represented by a formula:

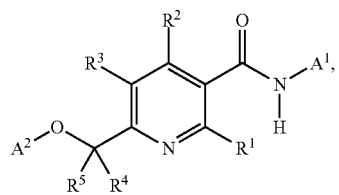

wherein $A^1$ is an organic residue having 2-10 carbons and selected from optionally substituted alkyl, optionally substituted cycloalkyl, optionally substituted heterocycloalkyl, optionally substituted cycloalkenyl, optionally substituted heterocycloalkenyl; optionally substituted aryl, and heteroaryl optionally substituted with one or more of halogen, methyl, trifluoromethyl, ethyl, propyl, or butyl; wherein $A^2$ is an optionally substituted organic residue selected from aryl and heteroaryl having 4-10 carbons; wherein $R^1$ and $R^2$ are independently selected from hydrogen, halogen, C1 to C6 alkyl, aryl, heteroaryl, cycloalkyl, heterocycloalkyl, cycloalkenyl, heterocycloalkenyl, OH, CN, $CO_2H$, $CF_3$, $OCF_3$, $OCH_3$, and —$CHRNH_2(OH)$, wherein $R^3$ is selected from hydrogen, hydroxyl, halogen, C1 to C6 alkyl, OH, CN, $CO_2H$, $CF_3$, $OCF_3$, $OCH_3$, and —$CHRNH_2(OH)$, wherein is R is $CF_3$; wherein $R^4$ and $R^5$ are independently selected from hydrogen, C1 to C6 alkyl, aryl, heteroaryl, cycloalkyl, heterocycloalkyl, cycloalkenyl, and heterocycloalkenyl, or wherein $R^4$ and $R^5$, together with the intermediate carbon, form a cyclic or heterocyclic ring having from 3 to 6 carbons; or a pharmaceutically acceptable salt or N-oxide thereof.

In one aspect, modulating is increasing. In a further aspect, modulating is potentiation. In a further aspect, modulating is partial agonism.

In one aspect, the cell is mammalian. In a further aspect, the cell is human. In a further aspect, the cell has been isolated from a mammal prior to the contacting step.

In a further aspect, contacting is via administration to a mammal. In a further aspect, the mammal has been diagnosed with a need for modulating mGluR5 activity prior to the administering step. In a further aspect, the mammal has been diagnosed with a need for treatment of a disorder related to mGluR5 activity prior to the administering step.

2. Manufacture of a Medicament

In one aspect, the invention relates to a method for the manufacture of a medicament for potentiation of metabotropic glutamate receptor activity in a mammal comprising combining a therapeutically effective amount of a disclosed compound or product of a disclosed method with a pharmaceutically acceptable carrier or diluent.

3. Use of Compounds

In one aspect, the invention relates to the use of a disclosed compound or a product of a disclosed method. In a further aspect, a use relates to the manufacture of a medicament for the treatment of a disorder associated with glutamate dysfunction in a mammal. In a further aspect, the disorder is a neurological and/or psychiatric disorder. In a further aspect, the disorder is a disease of uncontrolled cellular proliferation. In a further aspect, a use relates to treatment of a neurological and/or psychiatric disorder associated with glutamate dysfunction in a mammal.

In a further aspect, a use relates to potentiation of metabotropic glutamate receptor activity in a mammal. In a further aspect, a use relates to partial agonism of metabotropic glutamate receptor activity in a mammal. In a further aspect, a use relates to enhancing cognition in a mammal. In a further aspect, a use relates to modulating mGluR5 activity in a mammal. In a further aspect, a use relates to modulating mGluR5 activity in a cell.

4. Kits

In one aspect, the invention relates to a kit comprising a disclosed compound or a product of a disclosed method and one or more of at least one agent known to increase mGluR5 activity; at least one agent known to decrease mGluR5 activity; at least one agent known to treat a neurological and/or psychiatric disorder; at least one agent known to treat a disease of uncontrolled cellular proliferation; or instructions for treating a disorder associated with glutamate dysfunction.

In a further aspect, the at least one compound or the at least one product and the at least one agent are co-formulated. In a further aspect, the at least one compound or the at least one product and the at least one agent are co-packaged.

H. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein. All $^1$H NMR spectra were obtained on instrumentation at a field strength of 300 to 500 MHz.

The following exemplary compounds of the invention were synthesized. The Examples are provided herein to illustrate the invention, and should not be construed as limiting the invention in any way. The Examples are typically depicted in free base form, according to the IUPAC naming convention. However, some of the Examples were obtained or isolated in salt form.

As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

1. Methyl 6-(bromomethyl)nicotinate (1.1a)

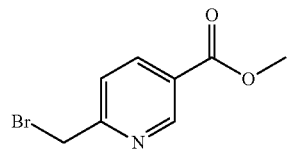

To a solution of methyl 6-methylnictinate (5.00 g, 33.1 mmol) in $CCl_4$ (120 mL) was added NBS (6.19 g, 34.7 mmol) and AIBN (150 mg). The reaction was heated to reflux and stirred for 1.5 h. The reaction was cooled to rt, filtered and the filtrate washed with water (120 mL). The organic layer was dried over $MgSO_4$, concentrated under reduced vacuum and purified by column chromatography (silica gel) using 0 to 30% EtOAc/hexanes to afford title compound (2.62 g): $^1$H-NMR (400 MHz, $CDCl_3$) δ 9.19 (d, J=2.0 Hz, 1H), 8.32

(dd, J=8.0, 2.0 Hz, 1H), 7.55 (d, J=8.0 Hz, 1H), 4.60 (s, 2H), 3.98 (s, 3H); LC-MS (214 nm) >98%, 230.2 and 232.0 [M+H].

2. Methyl 6-(phenoxymethyl)nicotinate (1.2a)

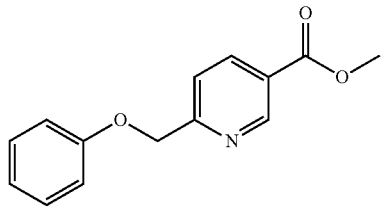 [SMILES: COC(=O)c1ccc(COc2ccccc2)nc1]

To a solution of phenol (489 mg, 5.21 mmol) and $K_2CO_3$ (1.44 g, 10.4 mmol) in DMF (15 mL) was added methyl 6-(bromomethyl)nicotinate (1.1a) (1.20 g, 5.21 mmol). The reaction was stirred at room temperature for 30 min and then diluted with water to give 1.2a after isolation by vacuum filtration and further drying in vacuo (810 mg): $^1$H-NMR (400 MHz, CDCl$_3$) δ 9.21 (d, J=2.0 Hz, 1H), 8.34 (dd, J=8.0, 2.0 Hz, 1H), 7.67 (d, J=8.0 Hz, 1H), 7.37-7.26 (m, 2H), 7.05-6.96 (m, 3H), 5.34 (s, 2H), 3.99 (s, 3H); LC-MS (220 nm) >98%, 244.2 [M+H].

3. Methyl 6-((3-fluorophenoxy)methyl)nicotinate (1.2b)

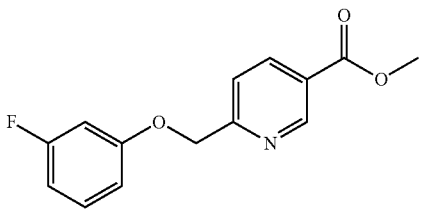 [SMILES: COC(=O)c1ccc(COc2cccc(F)c2)nc1]

Prepared in a similar manner to that described for intermediate 1.2a: $^1$H-NMR (400 MHz, CDCl$_3$) δ 9.22 (d, J=2.0 Hz, 1H), 8.35 (dd, J=8.0, 2.0 Hz, 1H), 7.67 (d, J=8.0 Hz, 1H), 7.27-7.22 (m, 1H), 6.80-6.69 (m, 3H), 5.27 (s, 2H), 3.99 (s, 3H); LC-MS (220 nm) >98%, 262.1 [M+H].

4. Methyl 6-((3,5-difluorophenoxy)methyl)nicotinate (1.2c)

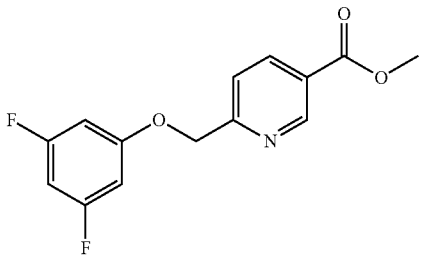 [SMILES: COC(=O)c1ccc(COc2cc(F)cc(F)c2)nc1]

Prepared in a similar manner to that described for intermediate 1.2a: $^1$H-NMR (400 MHz, CDCl$_3$) δ 9.22 (d, J=2.0 Hz, 1H), 8.36 (dd, J=8.0, 2.0 Hz, 1H), 7.60 (d, J=8.0 Hz, 1H), 6.56-6.39 (m, 3H), 5.25 (s, 2H), 3.99 (s, 3H); LC-MS (220 nm) >98%, 280.1 [M+H].

5. (R)-N-(1-cyclohexylethyl)-6-(hydroxymethyl)nicotinamide (3.2a)

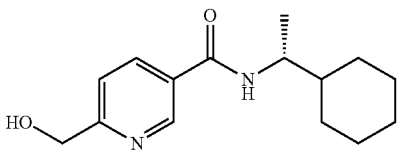 [SMILES: C[C@@H](NC(=O)c1ccc(CO)nc1)C1CCCCC1]

To a solution of (R)-N-(1-cyclohexylethyl)-6-methylnicotinamide (2.28 g, 9.3 mmol prepared from the starting 6-methylnicotinic acid) in CHCl$_3$ was added MCPBA (2.24 g, 1.4 eq) and stirred for 2 h at rt. Saturated aqueous NaHCO$_3$ was added and the organics extracted with CH$_2$Cl$_2$, dried over Na$_2$SO$_4$ and concentrated under reduced vacuum. The residue was dissolved in a minimal amount of acetic anhydride and heated to 125° C. for 40 min. The crude mixture was cooled to rt and aqueous NaHCO$_3$ added. The mixture was extracted with EtOAc, dried over Na$_2$SO$_4$, filtered and concentrated under vacuum. The resulting residue was stirred in MeOH (15 mL) and K$_2$CO$_3$ (1 g) for 2 h, concentrated under reduced pressure and partitioned between EtOAc and H$_2$O, Solvent removal and purification by column chromatography (silica gel) using 30-100% EtOAc/hexanes afforded 3.2a as a white solid (920 mg, 38%): $^1$H-NMR (400 MHz, CDCl$_3$) δ 8.91 (s, 1H), 8.13 (dd, J$_1$=8.0 Hz, J$_2$=2.0 Hz, 1H), 7.36 (d, J=8.0 Hz, 1H), 5.96 (d, J=8.0 Hz, 1H), 4.84 (s, 2H), 4.15-4.08 (m, 1 H), 1.85-1.04 (m, 14 H)); LC-MS (220 nm), >98%, 263.2 [M+H].

6. (R)-6-(bromomethyl)-N-(1-cyclohexylethyl)nicotinamide (3.3a)

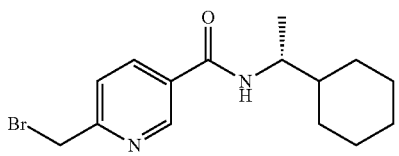 [SMILES: C[C@@H](NC(=O)c1ccc(CBr)nc1)C1CCCCC1]

A solution of (R)-N-(1-cyclohexylethyl)-6-(hydroxymethyl)nicotinamide (3.2a, 262 mg, 1 mmol) and Ph$_3$P (472 mg, 1.8 mmol) in CH$_2$Cl$_2$ (10 mL) was cooled to 0° C. and a solution of CBr$_4$ (463 mg, 1.4 mmol) in CH$_2$Cl$_2$ (2 mL) was added dropwise. The reaction was allowed to warm to rt and was stirred overnight. The reaction was concentrated under reduced pressure and the residue purified by column chromatography (silica gel) using 0-40% EtOAc/hexanes to afford 3.3a (156 mg): $^1$H-NMR (400 MHz, CDCl$_3$) δ 8.91 (s, 1H), 8.11 (dd, J$_1$=8.0 Hz, J$_2$=2.0 Hz, 1H), 7.53 (d, J=8.0 Hz, 1H), 5.98 (d, J=8.0 Hz, 1H), 4.59 (s, 2H), 4.15-4.07 (m, 1H), 1.84-1.68 (m, 5H), 1.49-1.43 (m, 1H), 1.29-1.03 (m, 8H); LC-MS (220 nm), >98%, 325.2 and 327.2 [M+H].

7. N-(3,3-dimethylbutyl)-6-(phenoxymethyl)nicotinamide (1.3a)

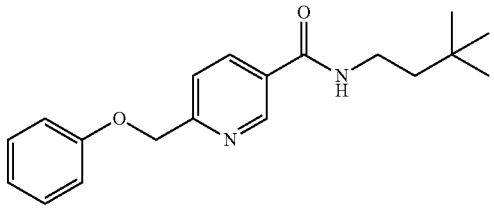 [SMILES: CC(C)(C)CCNC(=O)c1ccc(COc2ccccc2)nc1]

To a solution of ester 1.2a (800 mg, 3.29 mmol) in THF (16 ml) and MeOH (4 mL) was added a solution of LiOH (316 mg, 13.2 mmol) in water (4 mL) and stirred at room temperature for 4 h. The reaction was quenched upon addition of 1 N HCl (12 mL) and extracted with EtOAc (2×25 mL). The combined organic extracts were dried over MgSO$_4$ and concentrated under vacuum. The residue was dissolved in DMF (24 mL) and DIPEA (1.22 mL, 6.80 mmol) and HATU (1.29 g, 3.40) added sequentially. The solution was placed into multiple vials and reacted with 3,3-dimethylbutylamine (0.18 mmol) and allowed to stir at rt for 20 h. The reaction was diluted with water (5 mL) and extracted with EtOAc (2×3 mL). The combined organic extracts were dried, concentrated and purified by mass-directed prep reverse-phase HPLC: $^1$H-NMR (400 MHz, CDCl$_3$) δ 8.99 (s, 1H), 8.20 (d, J=8.0 Hz, 1H), 8.04 (s, 1H), 7.68 (d, J=8.0 Hz, 1H), 7.36-7.26 (m, 2H), 7.06-6.97 (m, 3H), 6.24 (s, 1H), 5.30 (s, 2H), 3.58-3.50 (m, 2H), 1.81-1.75 (m, 1H), 1.59-1.49 (m, 2H), 0.99 (d, J=7.0 Hz, 6H); LC-MS (214 nm) >98%, 313.2 [M+H].

8. (R)-N-(1-cyclohexylethyl)-6-(phenoxymethyl)nicotinamide (1.3b)

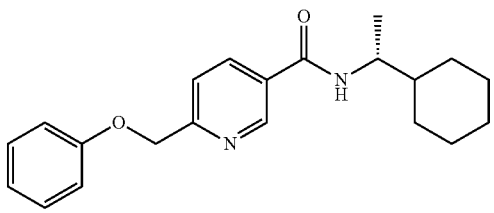 [SMILES: C[C@@H](NC(=O)c1ccc(COc2ccccc2)nc1)C1CCCCC1]

Prepared in a similar manner to that described for example 1.3a: $^1$H-NMR (400 MHz, CDCl$_3$) δ 8.95 (d, J=1.5 Hz, 1H), 8.12 (dd, J=8.0, 1.5 Hz, 1H), 7.63 (d, J=8.0 Hz, 1H), 7.36-7.28 (m, 2H), 7.05-6.96 (m, 3H), 5.90 (d, J=7.5 Hz, 1H), 5.28 (s, 2H), 4.16-4.08 (m, 1H), 1.98-1.65 (m, 5H), 1.49-1.42 (m, 1H), 1.23 (d, J=6.5 Hz, 3H), 1.36-0.98 (m, 5H); LC-MS (214 nm) >98%, 339.2 [M+H].

9. N-((1S/R,4R/S)-bicyclo[2.2.1]heptan-2-yl)-6-(phenoxymethyl)nicotinamide (1.3c)

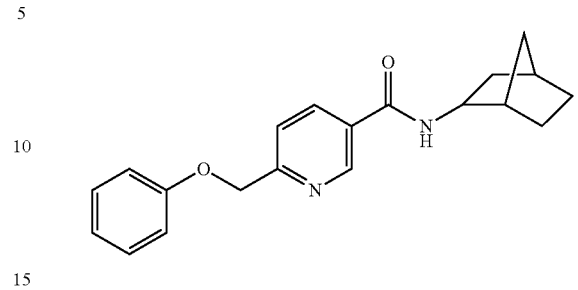

Prepared in a similar manner to that described for example 1.3a: $^1$H-NMR (400 MHz, CDCl$_3$) δ 10.16 (s, 1H), 8.99 (d, J=8.0 Hz, 1H), 8.59 (s, 1H), 8.18 (d, J=8.0 Hz, 1H), 7.35 (dd, J=8.0 Hz, 1H), 7.34 (d, J=8.0 Hz, 1H), 7.10-7.02 (m, 3H), 5.72 (s, 2H), 4.39-4.32 (m, 1H), 2.64 (s, 1H), 2.29 (s, 1H), 2.14-2.02 (m, 1H), 1.86-1.74 (m, 1H), 1.70-1.38 (m, 6H); LC-MS (214 nm) >95%, 323.1 [M+H].

10. 6-(phenoxymethyl)-N-(thiazol-2-yl)nicotinamide (1.3c)

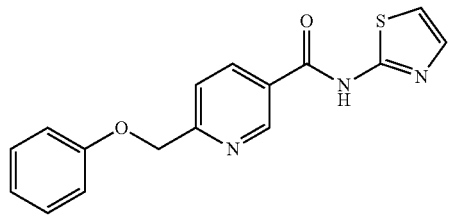 [SMILES: O=C(Nc1nccs1)c1ccc(COc2ccccc2)nc1]

Prepared in a similar manner to that described for example 1.3a: $^1$H-NMR (400 MHz, CDCl$_3$) δ 9.24 (d, J=1.5 Hz, 1H), 8.33 (dd, J=8.0, 1.5 Hz, 1H), 7.74 (d, J=8.0 Hz, 1H), 7.38-7.28 (m, 2H), 7.19 (d, J=4.0 Hz, 1H), 7.05-6.98 (m, 4H), 6.55 (d, J=4.0 Hz, 1H), 5.34 (s, 2H); LC-MS (214 nm) >98%, 312.1 [M+H].

11. N-(3,3-dimethylbutyl)-6-((3-fluorophenoxy)methyl)nicotinamide (1.3d)

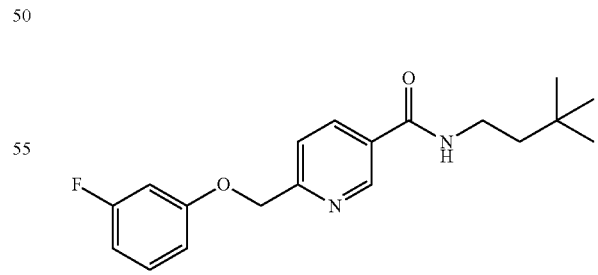

Prepared in a similar manner to that described for example 1.3a: $^1$H-NMR (400 MHz, CDCl$_3$) δ 8.95 (d, J=2.0 Hz, 1H), 8.16 (dd, J=8.0, 2.5 Hz, 1H), 7.59 (d, J=8.0 Hz, 1H), 6.53 (dd, J=9.0, 2.5 Hz, 2H), 6.48 (tt, J=9.0, 2.5 Hz, 1H), 6.04 (s, 1H), 5.24 (s, 2H), 3.56-3.50 (m, 2H), 1.61-1.54 (m, 2H), 1.01 (s, 9H); LC-MS (214 nM) 3.25 min; >98%; m/z 331.2.

12. (R)-N-(1-cyclohexylethyl)-6-(3-fluorophenoxy)methyl)nicotinamide (1.3e)

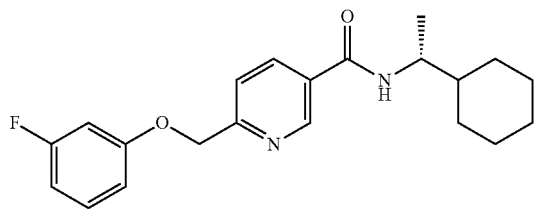 [SMILES: C[C@@H](NC(=O)c1ccc(COc2cccc(F)c2)nc1)C1CCCCC1]

Prepared according to Scheme 3. A THF solution of intermediate (R)-6-(bromomethyl)-N-(1-cyclohexylethyl)nicotinamide (3.3a) was treated with 3-fluorophenol (1.2 equiv) and $K_2CO_3$ (3 equiv). After stirring at rt for 2 h the mixture was diluted with water and EtOAc. The organic layer was successively washed with aq. $Na_2CO_3$ and brine and dried over $Na_2SO_4$. Solvent removal and purification via mass guided RP-HPLC gave title compound 1.3e: $^1$H-NMR (400 MHz, CDCl$_3$) δ 9.97 (s, 1H), 8.94 (d, J=8.0 Hz, 1H), 8.11 (s, 1H), 8.10 (d, J=8.0 Hz, 1H), 7.29-7.26 (m, 1H), 6.87-6.75 (m, 3H), 5.67 (s, 2H), 4.12 (q, J=6.5 Hz, 1H), 1.92-1.60 (m, 8H), 1.32 (d, J=6.5 Hz, 3H), 1.29-1.15 (m, 3H); LC-MS (214 nm) >98%, 357.2 [M+H].

13. N-cyclobutyl-6-((3-fluorophenoxy)methyl)nicotinamide (1.3f)

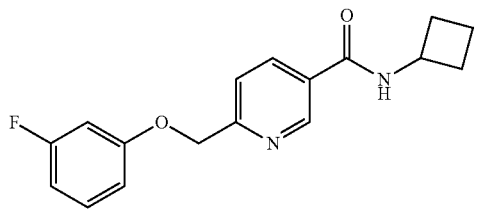 [SMILES: O=C(NC1CCC1)c1ccc(COc2cccc(F)c2)nc1]

Prepared in a similar manner to that described for example 1.3a: $^1$H-NMR (400 MHz, CDCl$_3$) δ 8.95 (d, J=2.0 Hz, 1H), 8.13 (dd, J=8.0, 2.5 Hz, 1H), 7.61 (d, J=8.0 Hz, 1H), 7.27-7.21 (m, 1H), 6.77 (dd, J=8.0, 2.0 Hz, 1H), 6.72-6.65 (m, 1H), 6.22 (s, 1H), 5.25 (s, 2H), 4.70-4.62 (m, 1H), 2.53-2.44 (m, 2H), 2.08-1.95 (m, 2H), 1.87-1.77 (m, 2H); LC-MS (214 nM) >98%; 301.2 [M+H].

14. (R)-N-(1-cyclopropylethyl)-6((3-fluorophenoxy)methyl)nicotinamide (1.3g)

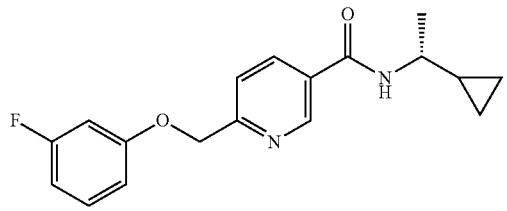 [SMILES: C[C@@H](NC(=O)c1ccc(COc2cccc(F)c2)nc1)C1CC1]

Prepared in a similar manner to that described for example 1.3a: $^1$H-NMR (400 MHz, CDCl$_3$) δ 10.02 (s, 1H), 8.94 (d, J=8.0 Hz, 1H), 8.44 (s, 1H), 8.10 (d, J=8.0 Hz, 1H), 7.29-7.24 (m, 1H), 6.85-6.73 (m, 3H), 5.67 (s, 2H), 3.62 (q, J=8.0 Hz, 1H), 1.44 (d, J=6.5 Hz, 3H), 1.25-1.15 (m, 1H), 0.62-0.44 (m, 3H), 0.33-0.28 (m, 1H); LC-MS (214 nm) >98%, 315.1 [M+H].

15. 6-((3,5-difluorophenoxy)methyl)-N-(3,3-dimethylbutyl)nicotinamide (1.3h)

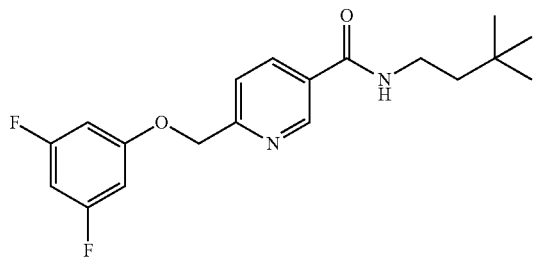 [SMILES: CC(C)(C)CCNC(=O)c1ccc(COc2cc(F)cc(F)c2)nc1]

Prepared in a similar manner to that described for example 1.3a: $^1$H-NMR (400 MHz, CDCl$_3$) δ 8.98 (d, J=2.0 Hz, 1H), 8.23 (dd, J=8.0, 2.5 Hz, 1H), 7.61 (d, J=8.0 Hz, 1H), 7.08 (d, J=2.0 Hz, 1H), 7.06-7.01 (m, 1H), 6.98 (dt, J=9.0, 2.5 Hz, 1H), 6.09 (s, 1H), 5.30 (s, 2H), 3.58-3.51 (m, 2H), 1.61-1.55 (m, 2H), 1.01 (s, 9H); LC-MS (214 nm) >98%, 349.2 [M+H].

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

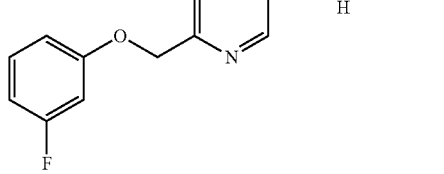

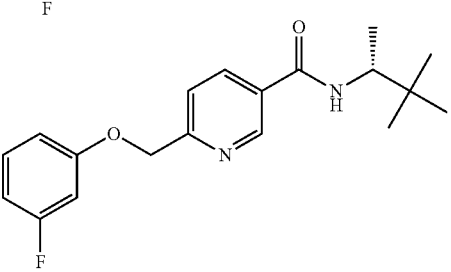

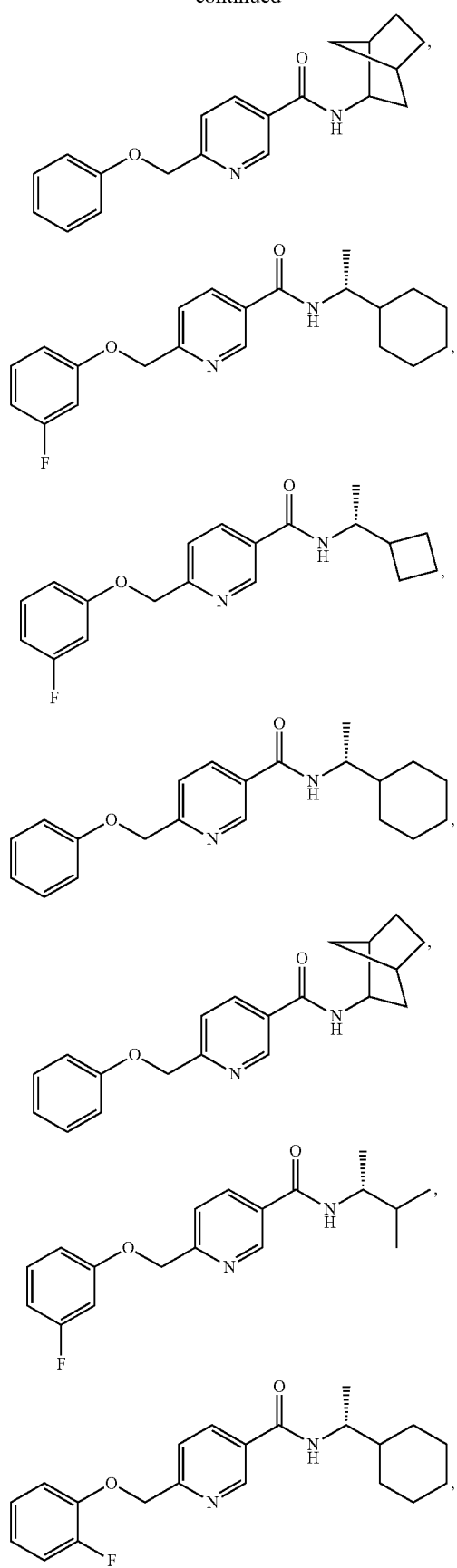
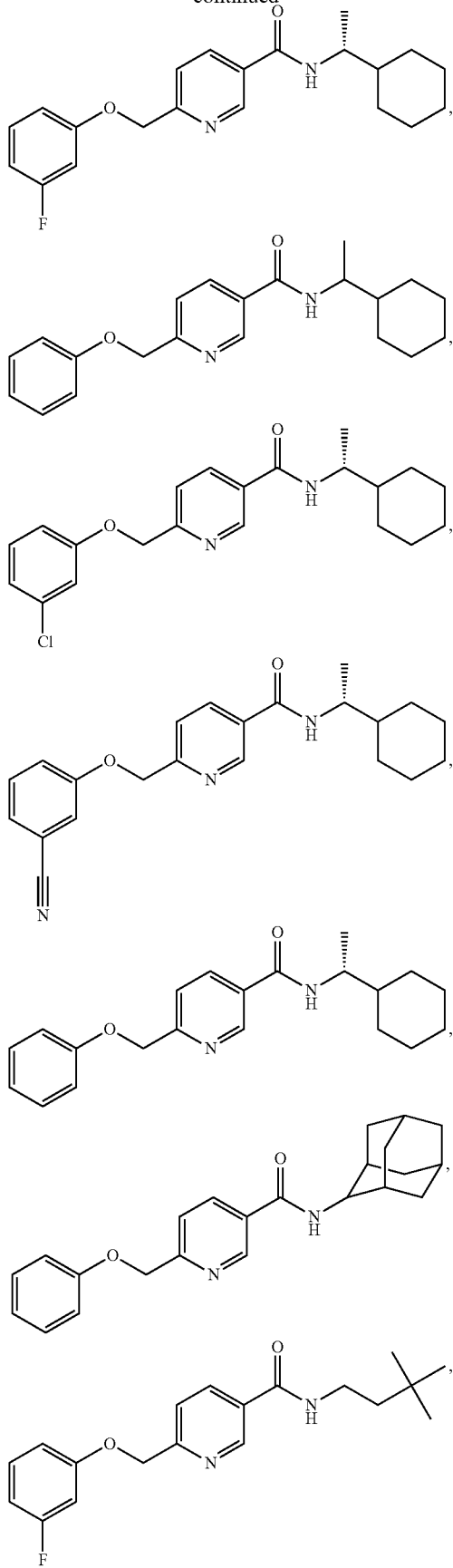

135
136

137
-continued
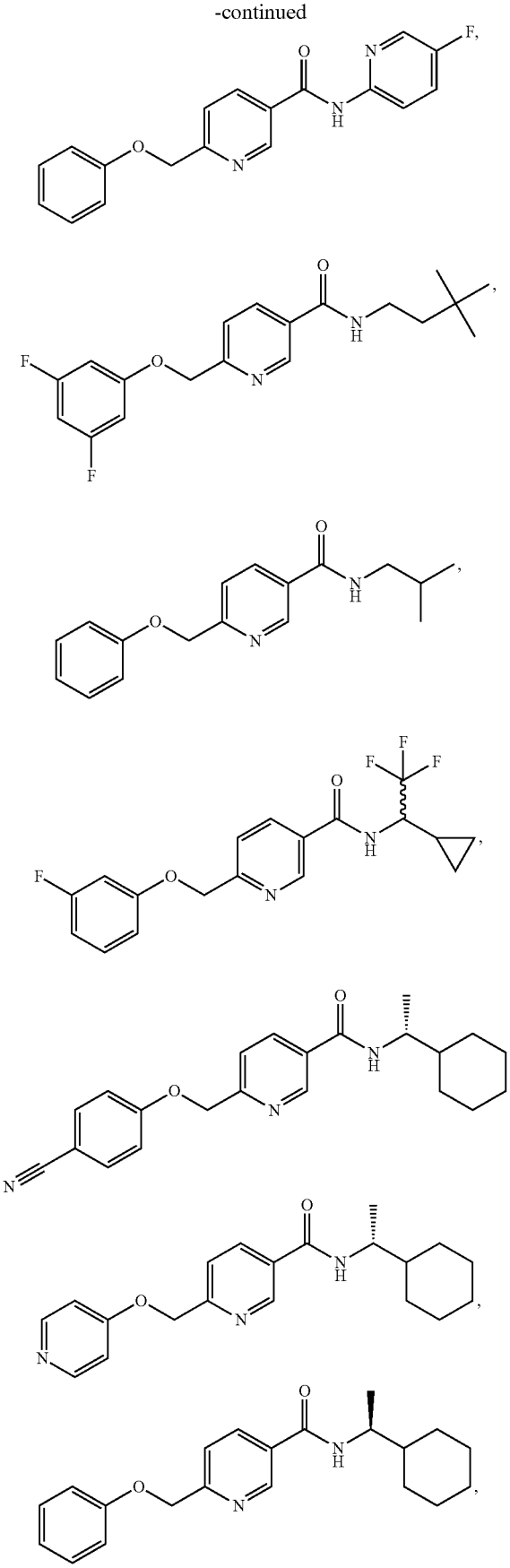
138
-continued
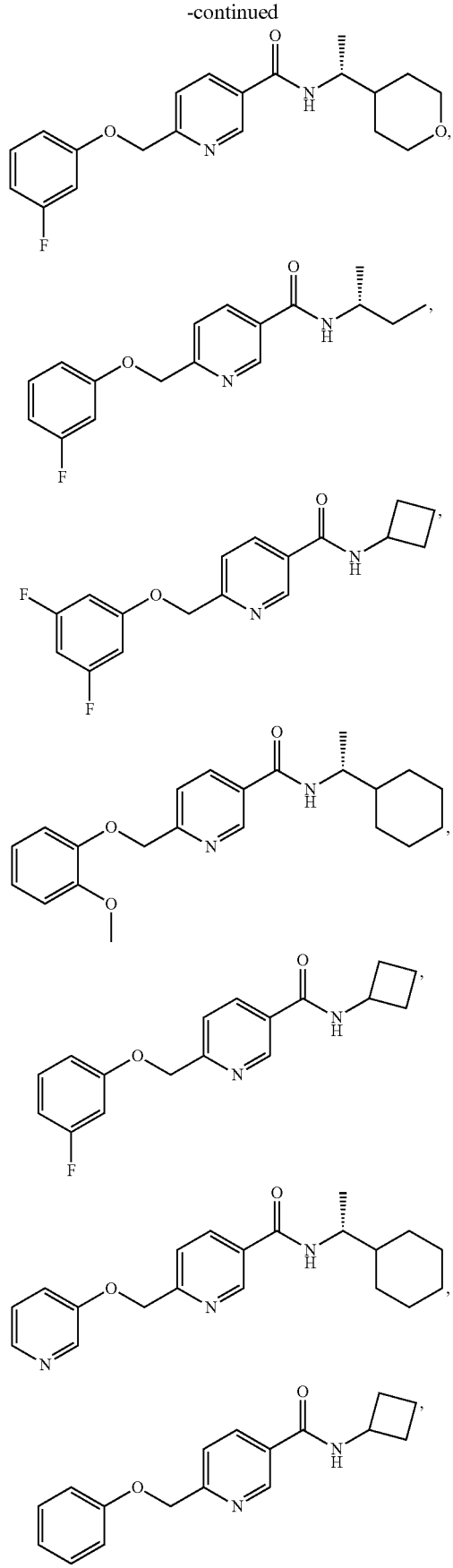

139
-continued
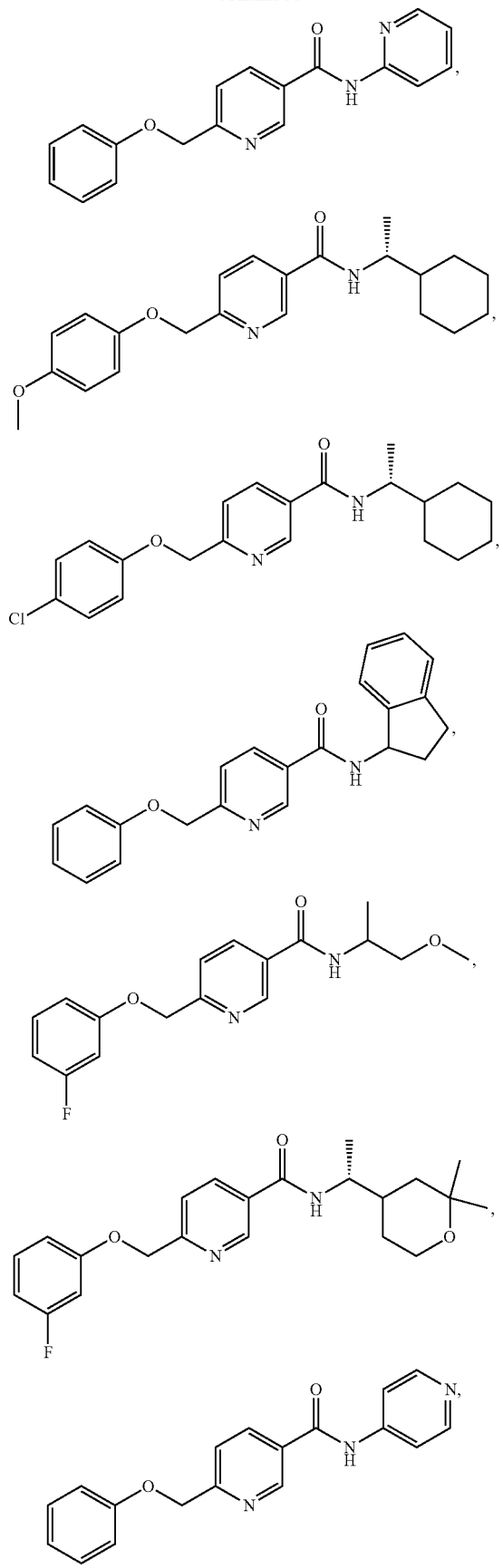
140
-continued
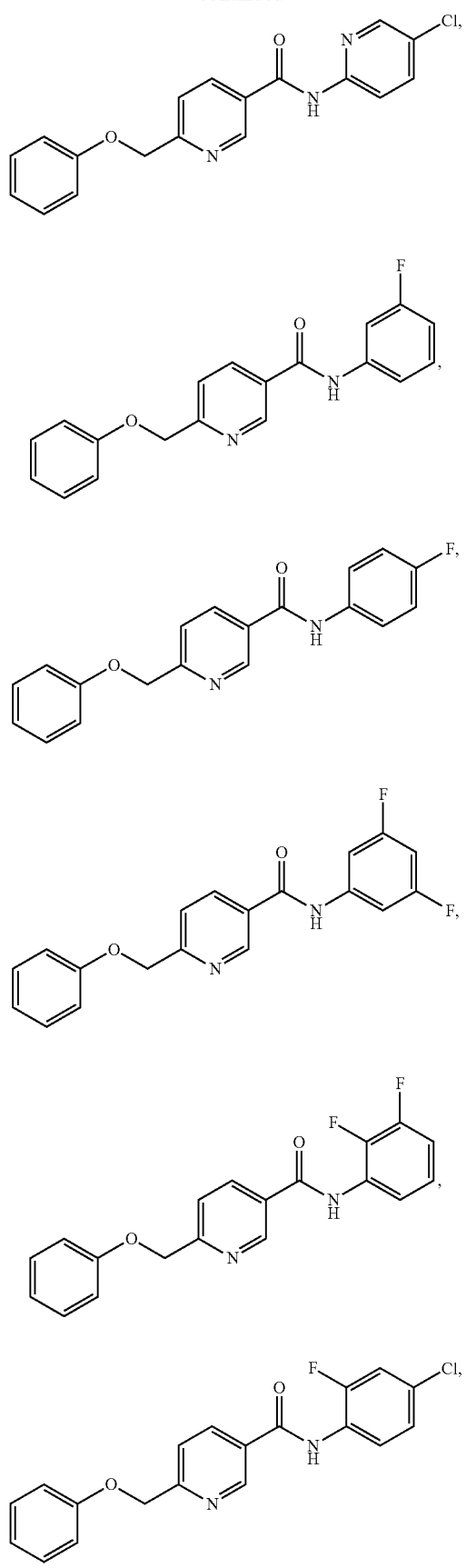

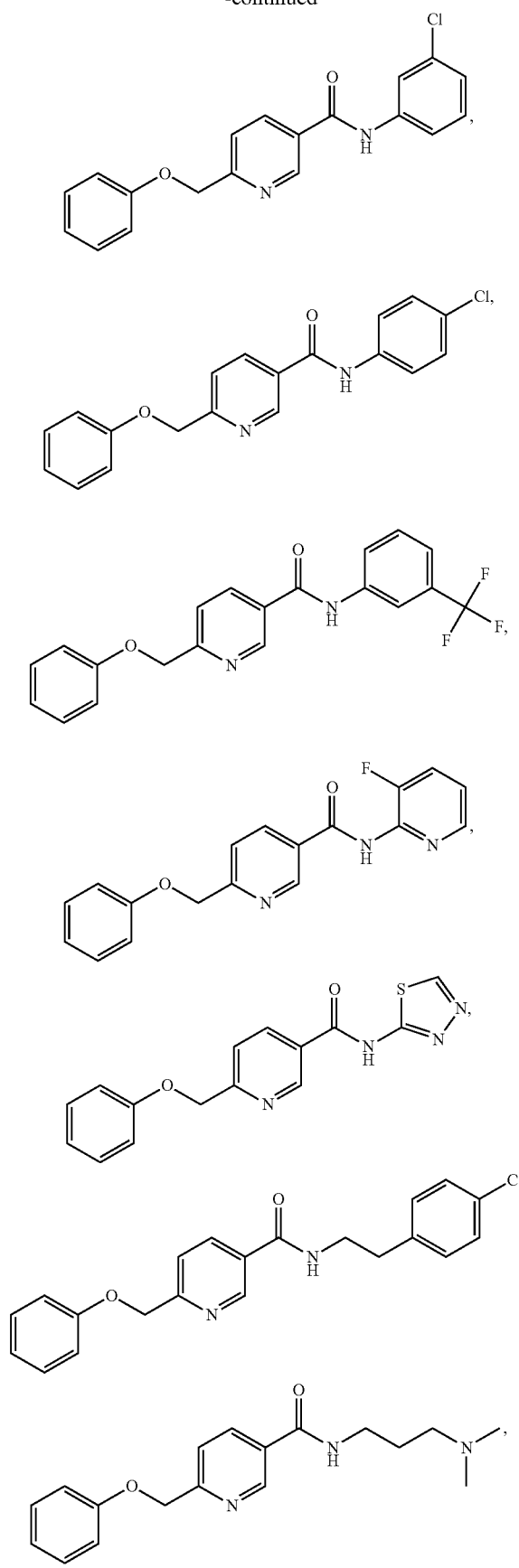
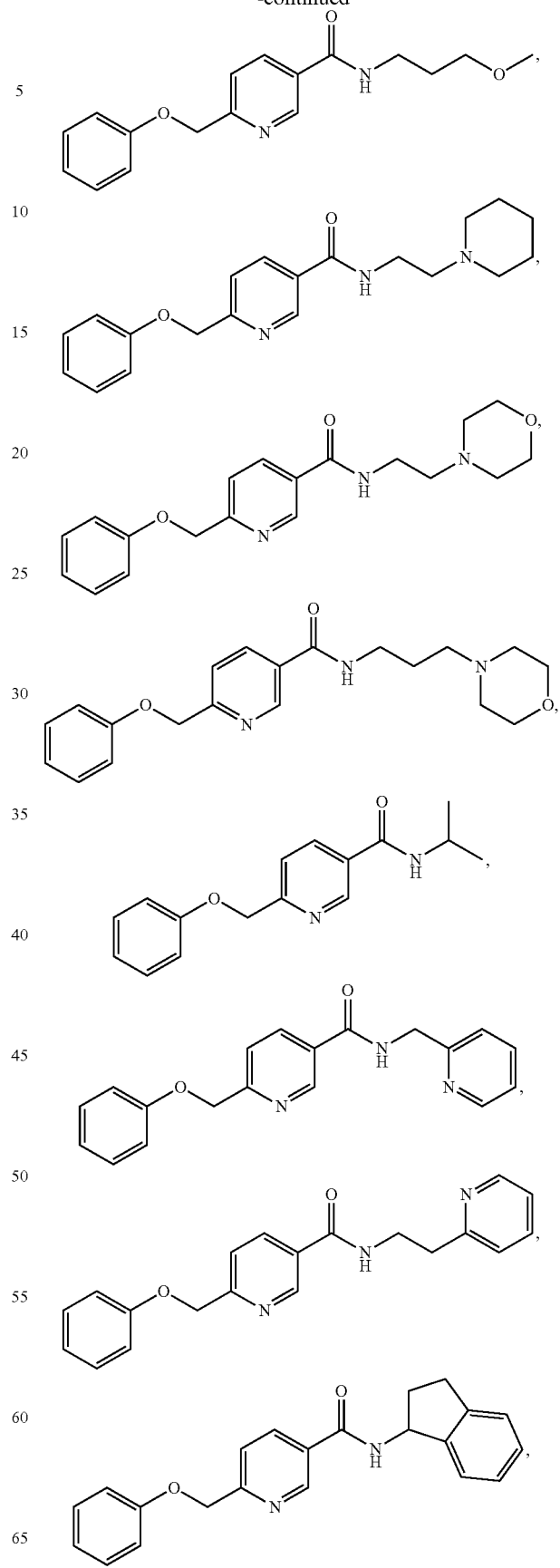

143
-continued
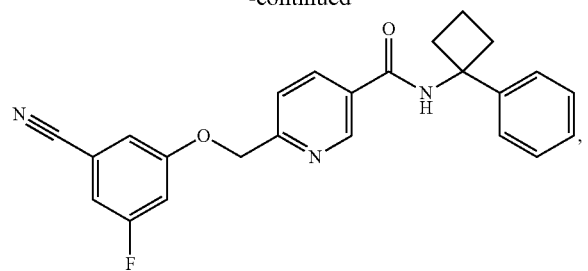
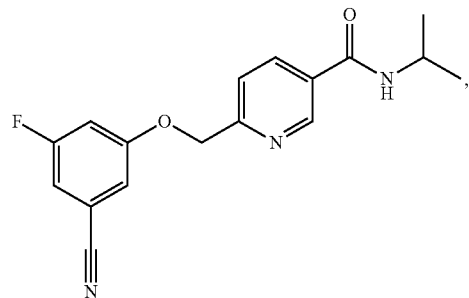
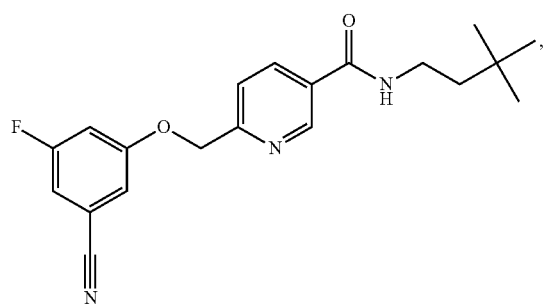
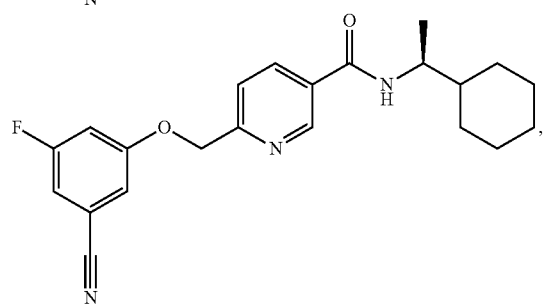
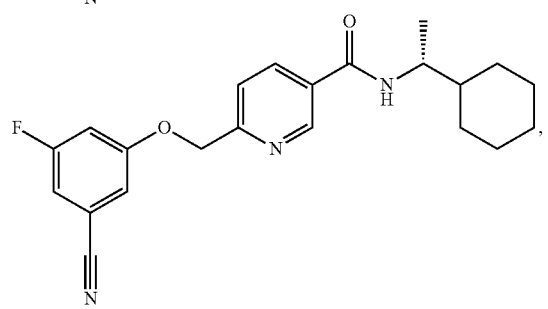
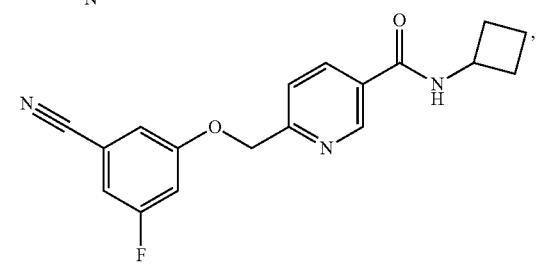
144
-continued
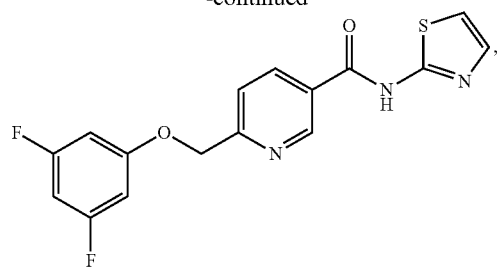
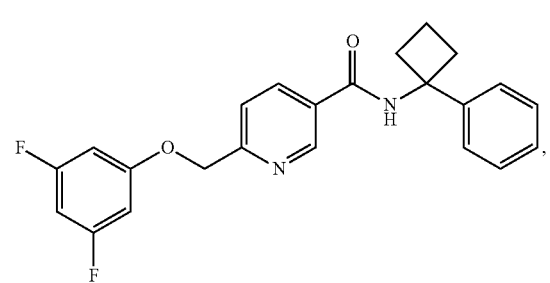
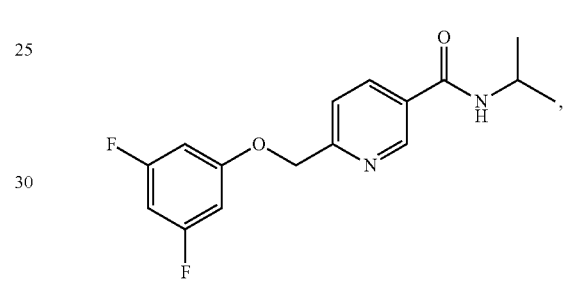
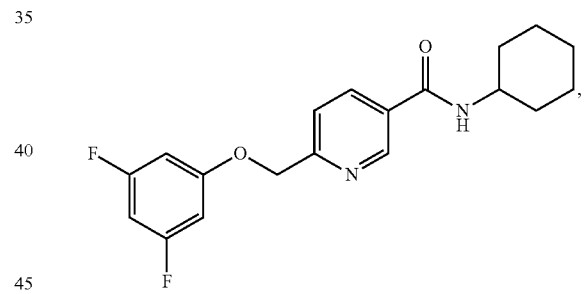
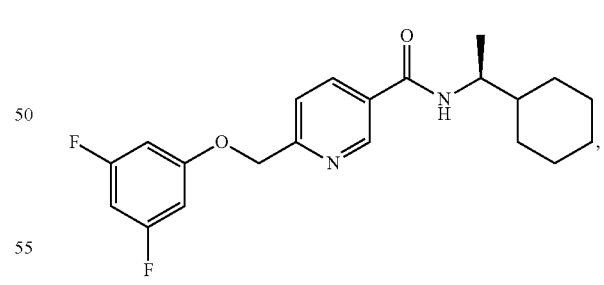
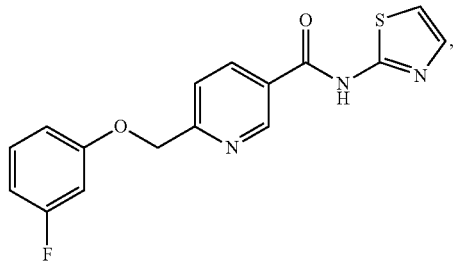

145
-continued

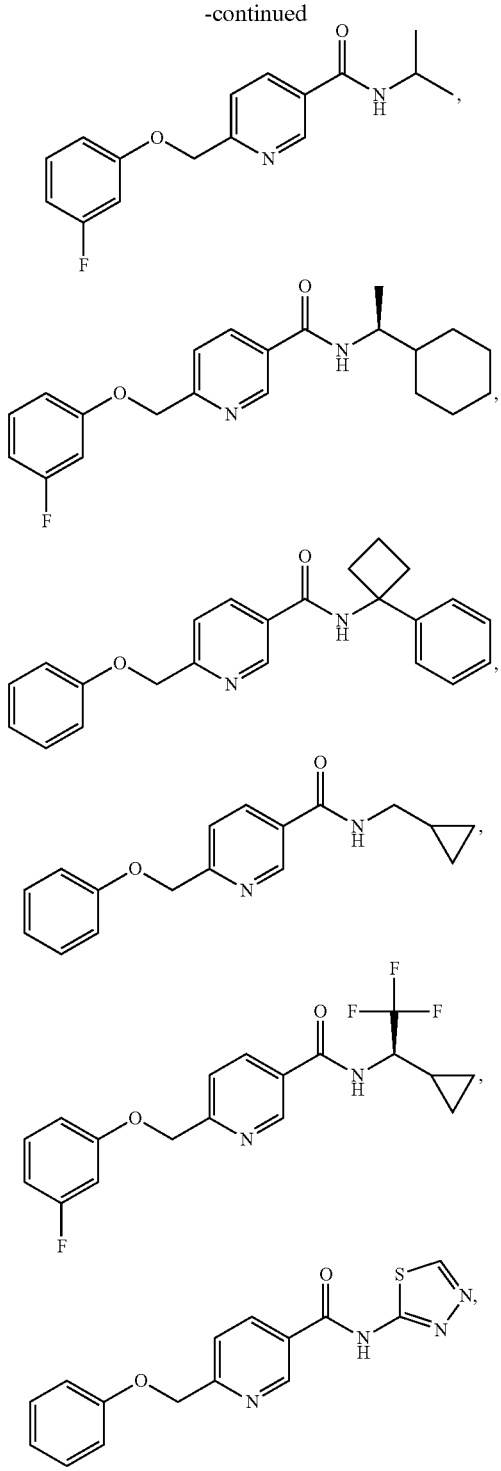

146
-continued

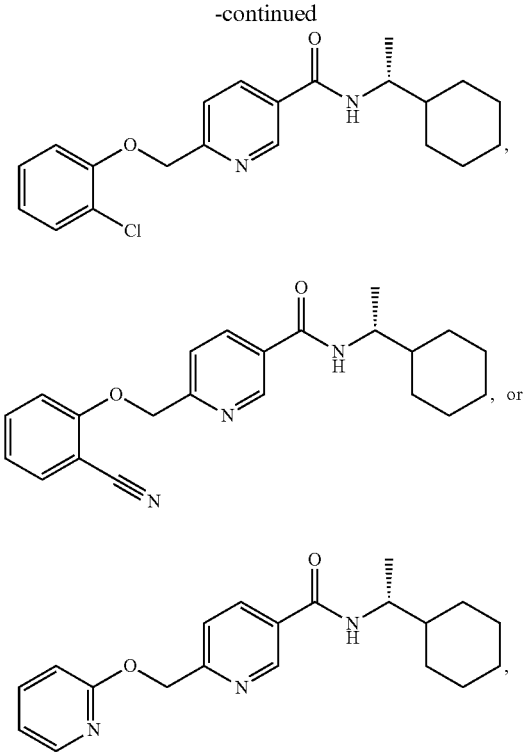

or a pharmaceutically acceptable salt or N-oxide thereof.

2. A method for the treatment of a neurological and/or psychiatric disorder associated with glutamate dysfunction in a mammal comprising the step of administering to the mammal a therapeutically effective amount of least one compound of claim 1 or a pharmaceutically acceptable salt or N-oxide thereof.

3. The method of claim 2, wherein the disorder is selected from dementia, delirium, amnestic disorders, age-related cognitive decline, schizophrenia, psychosis including schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression.

4. A pharmaceutical composition comprising a therapeutically effective amount of at least one disclosed compound of claim 1 and a pharmaceutically acceptable carrier.

\* \* \* \* \*